(12) United States Patent
Rofougaran et al.

(10) Patent No.: US 8,515,533 B2
(45) Date of Patent: Aug. 20, 2013

(54) BIO-MEDICAL UNIT SYSTEM FOR PHYSICAL THERAPY

(75) Inventors: Ahmadreza (Reza) Rofougaran, Newport Coast, CA (US); Jeyhan Karaoguz, Irvine, CA (US); Pieter Vorenkamp, Laguna Niguel, CA (US)

(73) Assignee: Broadcom Corporation, Irvine, CA (US)

( * ) Notice: Subject to any disclaimer, the term of this patent is extended or adjusted under 35 U.S.C. 154(b) by 67 days.

(21) Appl. No.: 13/029,435

(22) Filed: Feb. 17, 2011

(65) Prior Publication Data

US 2011/0160802 A1 Jun. 30, 2011

Related U.S. Application Data

(63) Continuation-in-part of application No. 12/649,030, filed on Dec. 29, 2009, and a continuation-in-part of application No. 12/783,649, filed on May 20, 2010, and a continuation-in-part of application No. 12/787,786, filed on May 26, 2010, and a continuation-in-part of application No. 12/829,279, filed on Jul. 1, 2010, and a continuation-in-part of application No. 12/848,830, filed on Aug. 2, 2010.

(60) Provisional application No. 61/247,060, filed on Sep. 30, 2009.

(51) Int. Cl.
*A61N 1/00* (2006.01)

(52) U.S. Cl.
USPC ........ 607/2; 607/32; 607/35; 607/59; 607/60; 607/61

(58) Field of Classification Search
USPC ................................. 607/2, 32, 35, 59, 60, 61
See application file for complete search history.

(56) References Cited

U.S. PATENT DOCUMENTS

| 7,729,776 B2* | 6/2010 | Von Arx et al. | 607/60 |
| 2005/0070982 A1* | 3/2005 | Heruth et al. | 607/119 |
| 2007/0233197 A1* | 10/2007 | Jung et al. | 607/5 |
| 2008/0021972 A1* | 1/2008 | Huelskamp et al. | 709/211 |

* cited by examiner

*Primary Examiner* — Niketa Patel
*Assistant Examiner* — Lindsey G Hankins
(74) *Attorney, Agent, or Firm* — Garlick & Markison; Kevin L. Smith

(57) ABSTRACT

A system includes bio-medical units and an electromagnetic signal generating unit. A bio-medical unit includes a power harvesting module, a wireless communication module, a processing module, and a functional module that performs physical therapy function and generates physical therapy data. The electromagnetic signal generating unit that includes at least one signal generating module and a plurality of near field communication (NFC) modules. The signal generating module generates one or more signals and an NFC module converts the one or more signals into a component of electromagnetic signal, which the power harvesting module converts into a supply voltage that powers the other modules of the bio-medical unit.

20 Claims, 53 Drawing Sheets

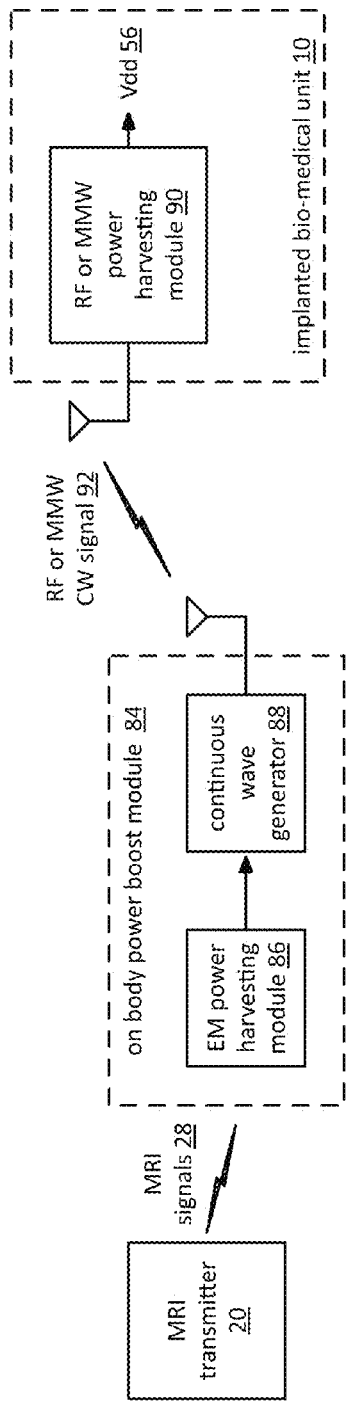
FIG. 13
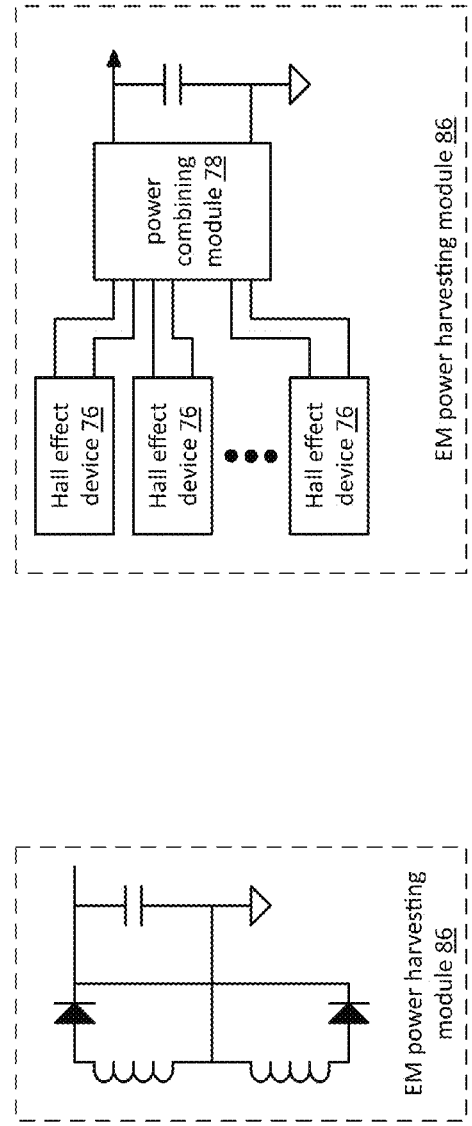
FIG. 15
FIG. 14

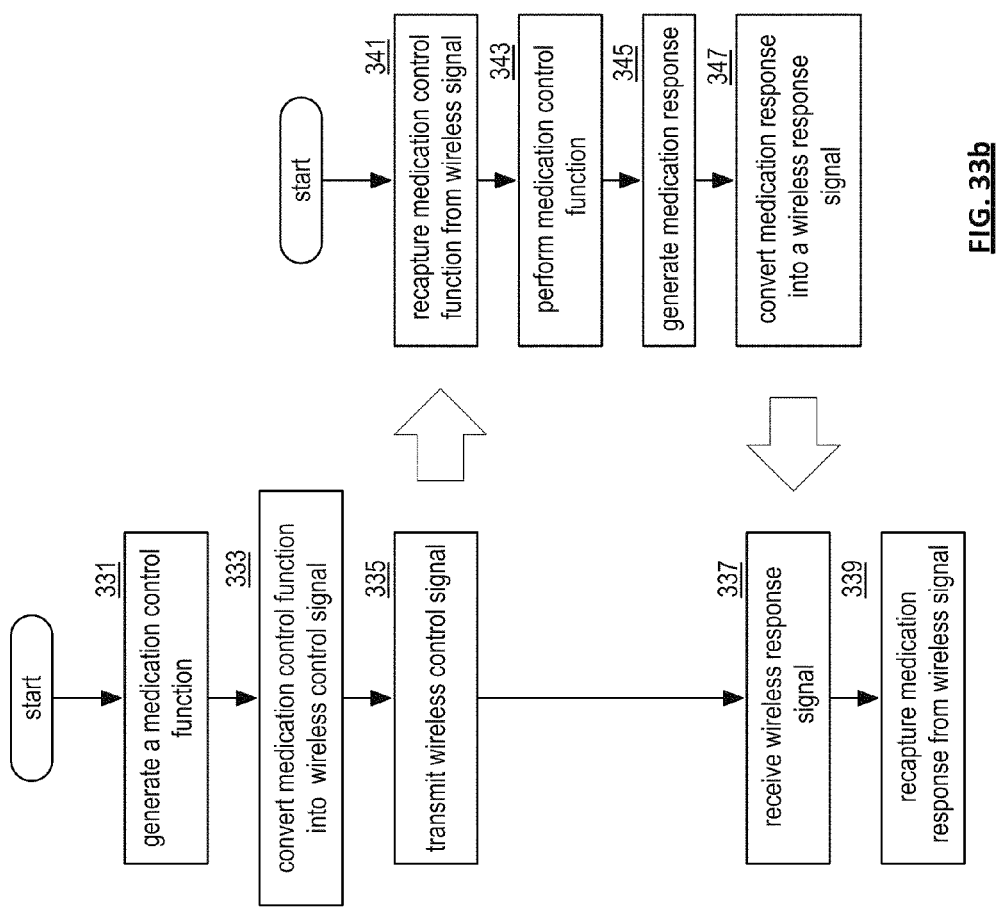

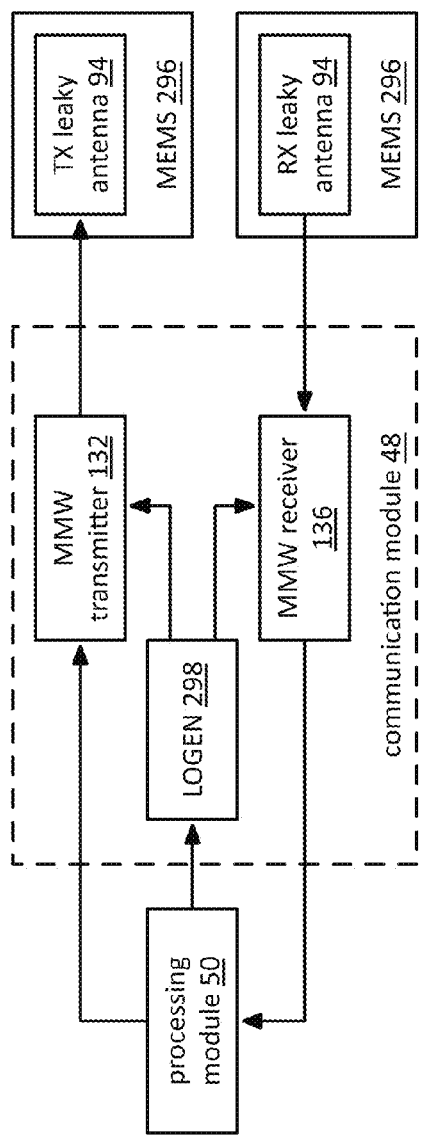
FIG. 47
FIG. 48
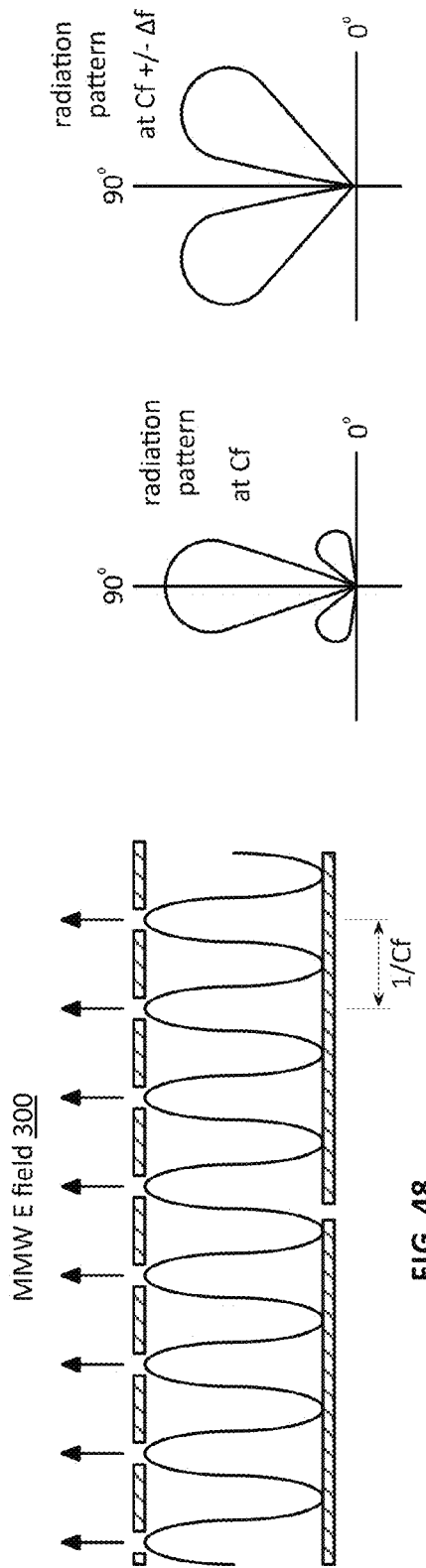
FIG. 49
FIG. 50

US 8,515,533 B2

BIO-MEDICAL UNIT SYSTEM FOR PHYSICAL THERAPY

CROSS REFERENCE TO RELATED PATENTS

This patent application is claiming priority under 35 USC §120 as a continuation-in-part to the following U.S. Utility Patent Applications which are hereby incorporated herein by reference in their entirety and made part of the present U.S. Utility Patent Application for all purposes:
1. entitled, "ARTIFICIAL BODY PART INCLUDING BIO-MEDICAL UNITS", having a filing date of Dec. 29, 2009, and a Ser. No. 12/649,030, pending;
2. entitled, "BIO-MEDICAL UNIT WITH IMAGE SENSOR FOR IN VIVO IMAGING, having a filing date of Jul. 1, 2010, and a Ser. No. 12/829,279, pending;
3. entitled, "COMMUNICATION DEVICE FOR COMMUNICATING WITH A BIOMEDICAL UNIT", having a filing date of May 26, 2010, and a Ser. No. 12/787,786, pending;
4. entitled, "BIO-MEDICAL UNIT WITH POWER HARVESTING MODULE AND RF COMMUNICATION", having a filing date of May 20, 2010, and a Ser. No. 12/783,649, pending;
5. entitled, "PAIN MANAGEMENT BIO-MEDICAL UNIT", having a filing date of Aug. 2, 2010, and a Ser. No. 12/848,830, pending;

all of which claim priority pursuant to 35 U.S.C. §119(e) to the following U.S. Provisional Patent Application which is hereby incorporated herein by reference in its entirety and made part of the present U.S. Utility Patent Application for all purposes:
a. U.S. Provisional Application No. 61/247,060, entitled "BIO-MEDICAL UNIT AND APPLICATIONS THEREOF, filed Sep. 30, 2009.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

1. Technical Field of the Invention

This invention relates generally to medical equipment and more particularly to wireless medical equipment.

2. Description of Related Art

As is known, there is a wide variety of medical equipment that aids in the diagnosis, monitoring, and/or treatment of patients' medical conditions. For instances, there are diagnostic medical devices, therapeutic medical devices, life support medical devices, medical monitoring devices, medical laboratory equipment, etc. As specific exampled magnetic resonance imaging (MRI) devices produce images that illustrate the internal structure and function of a body.

The advancement of medical equipment is in step with the advancements of other technologies (e.g., radio frequency identification (RFID), robotics, etc.). Recently, RFID technology has been used for in vitro use to store patient information for easy access. While such in vitro applications have begun, the technical advancement in this area is in its infancy.

Therefore, a need exists for a bio-medical unit that has applications within artificial body part implants.

BRIEF SUMMARY OF THE INVENTION

The present invention is directed to apparatus and methods of operation that are further described in the following Brief Description of the Drawings, the Detailed Description of the Invention, and the claims. Other features and advantages of the present invention will become apparent from the following detailed description of the invention made with reference to the accompanying drawings.

BRIEF DESCRIPTION OF THE SEVERAL VIEWS OF THE DRAWING(S)

FIG. 13 is a schematic block diagram of an embodiment of a power boost module in accordance with the present invention;

FIG. 14 is a schematic block diagram of an embodiment of an electromagnetic (EM) power harvesting module in accordance with the present invention;

FIG. 15 is a schematic block diagram of another embodiment of an EM power harvesting module in accordance with the present invention;

FIGS. 33a and 33b are logic diagrams of an embodiment of a method for controlling and/or monitoring medication administration in accordance with the present invention;

FIG. 47 is a schematic block diagram of another embodiment of a bio-medical unit in accordance with the present invention;

FIG. 48 is a schematic block diagram of an embodiment of a leaky antenna of the bio-medical unit of FIG. 47 in accordance with the present invention;

FIG. 49 is a diagram of an example of an antenna radiation pattern of the leaky antenna of FIG. 48 in accordance with the present invention; and FIG. 50 is a diagram of another example of an antenna radiation pattern of the leaky antenna of FIG. 48 in accordance with the present invention.

DETAILED DESCRIPTION OF THE INVENTION

Figure 1:
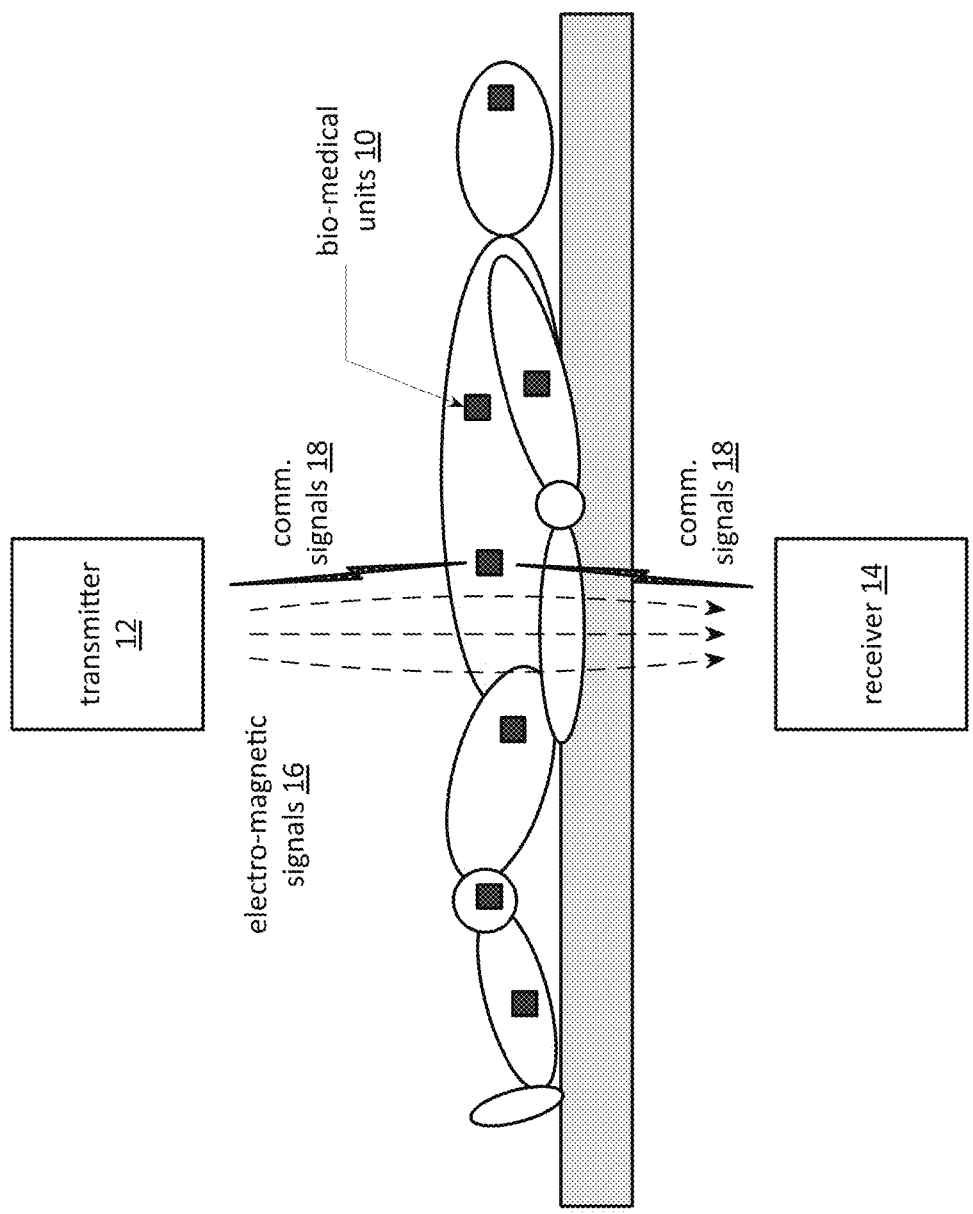
FIG. 1 is a diagram of an embodiment of a system in accordance with the present invention.

FIG. 1 is a diagram of an embodiment of a system that includes a plurality of bio-medical units 10 embedded within a body and/or placed on the surface of the body to facilitate diagnosis, treatment, and/or data collections. Each of the bio-medical units 10 is a passive device (e.g., it does not include a power source (e.g., a battery)) and, as such, includes a power harvesting module. The bio-medical units 10 may also include one or more of memory, a processing module, and functional modules. Alternatively, or in addition to, each of the bio-medical units 10 may include a rechargeable power source.

In operation, a transmitter 12 emits electromagnetic signals 16 that pass through the body and are received by a receiver 14. The transmitter 12 and receiver 14 may be part of a piece of medical diagnostic equipment (e.g., magnetic resonance imaging (MRI), X-ray, etc.) or independent components for stimulating and communicating with the network of bio-medical units in and/or on a body. One or more of the bio-medical units 10 receives the transmitted electromagnetic signals 16 and generates a supply voltage therefrom. Examples of this will be described in greater detail with reference to FIGS. 8-12.

Embedded within the electromagnetic signals 16 (e.g., radio frequency (RF) signals, millimeter wave (MMW) signals, MRI signals, etc.) or via separate signals, the transmitter 12 communicates with one or more of the bio-medical units 10. For example, the electromagnetic signals 16 may have a frequency in the range of a few MHz to 900 MHz and the communication with the bio-medical units 10 is modulated on the electromagnetic signals 16 at a much higher frequency (e.g., 5 GHz to 300 GHz). As another example, the communication with the bio-medical units 10 may occur during gaps (e.g., per protocol of medical equipment or injected for communication) of transmitting the electromagnetic signals 16. As another example, the communication with the bio-medical units 10 occurs in a different frequency band and/or using a different transmission medium (e.g., use RF or MMW signals when the magnetic field of the electromagnetic signals are dominate, use ultrasound signals when the electromagnetic signals 16 are RF and/or MMW signals, etc.).

One or more of the bio-medical units 10 receives the communication signals 18 and processes them accordingly. The communication signals 18 may be instructions to collect data, to transmit collected data, to move the unit's position in the body, to perform a function, to administer a treatment, etc. If the received communication signals 18 require a response, the bio-medical unit 10 prepares an appropriate response and transmits it to the receiver 14 using a similar communication convention used by the transmitter 12.

Figure 2:
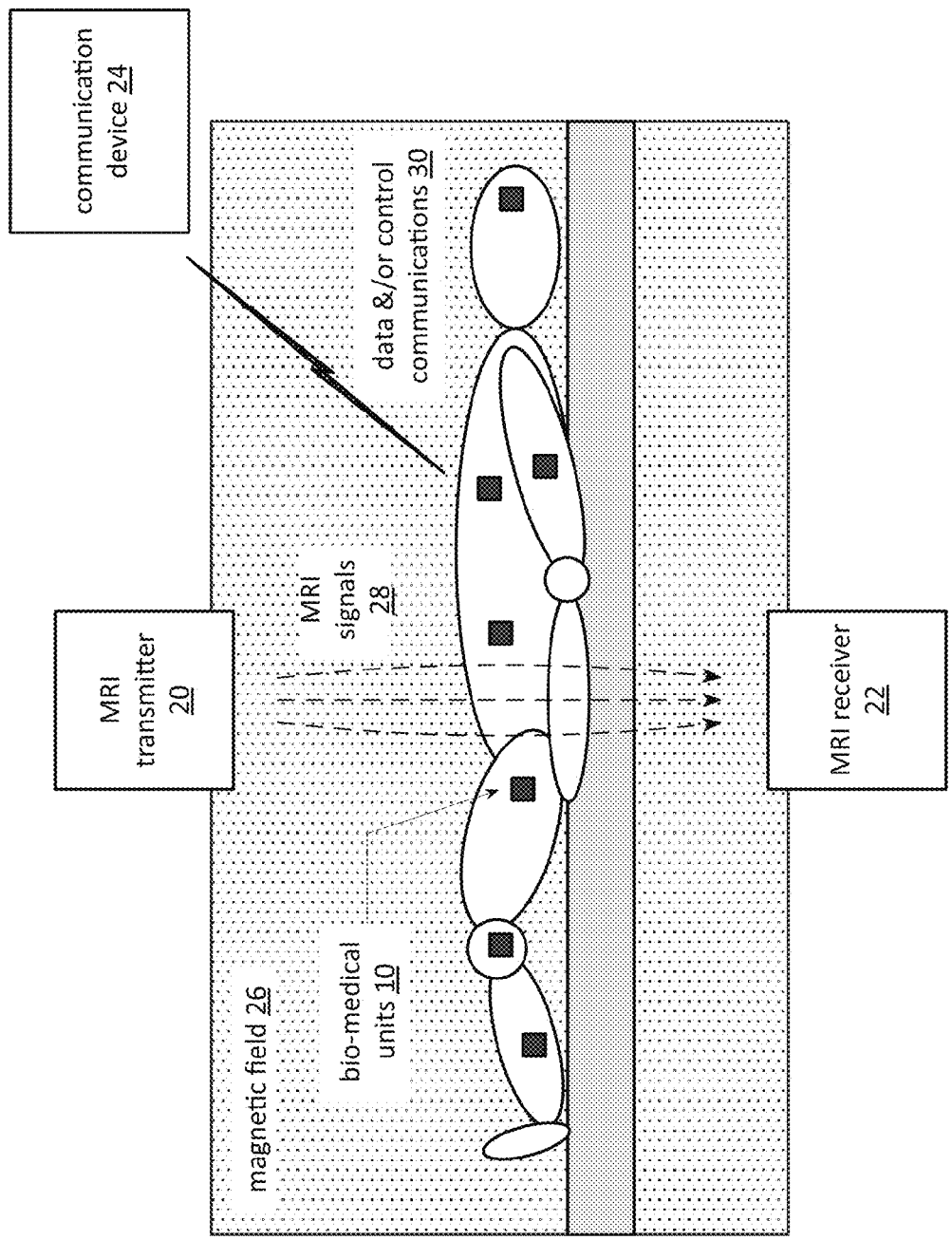
FIG. 2 is a diagram of another embodiment of a system in accordance with the present invention.

FIG. 2 is a diagram of another embodiment of a system that includes a plurality of bio-medical units 10 embedded within a body and/or placed on the surface of the body to facilitate diagnosis, treatment, and/or data collections. Each of the bio-medical units 10 is a passive device and, as such, includes a power harvesting module. The bio-medical units 10 may also include one or more of memory, a processing module, and functional modules. In this embodiment, the person is placed in an MRI machine (fixed or portable) that generates a magnetic field 26 through which the MRI transmitter 20 transmits MRI signals 28 to the MRI receiver 22.

One or more of the bio-medical units 10 powers itself by harvesting energy from the magnetic field 26 or changes thereof as produced by gradient coils, from the magnetic fields of the MRI signals 28, from the electrical fields of the MRI signals 28, and/or from the electromagnetic aspects of the MRI signals 28. A unit 10 converts the harvested energy into a supply voltage that supplies other components of the unit (e.g., a communication module, a processing module, memory, a functional module, etc.).

A communication device 24 communicates data and/or control communications 30 with one or more of the bio-medical units 10 over one or more wireless links. The communication device 24 may be a separate device from the MRI machine or integrated into the MRI machine. For example, the communication device 24, whether integrated or separate, may be a cellular telephone, a computer with a wireless interface (e.g., a WLAN station and/or access point, Bluetooth, a proprietary protocol, etc.). A wireless link may be one or more frequencies in the ISM band, in the 60 GHz frequency band, the ultrasound frequency band, and/or other frequency bands that supports one or more communication protocols (e.g., data modulation schemes, beamforming, RF or MMW modulation, encoding, error correction, etc.).

The composition of the bio-medical units 10 includes non-ferromagnetic materials (e.g., paramagnetic or diamagnetic) and/or metal alloys that are minimally affected by an external magnetic field 26. In this regard, the units harvest power from the MRI signals 28 and communicate using RF and/or MMW electromagnetic signals with negligible chance of encountering the projectile or missile effect of implants that include ferromagnetic materials.

Figure 3:
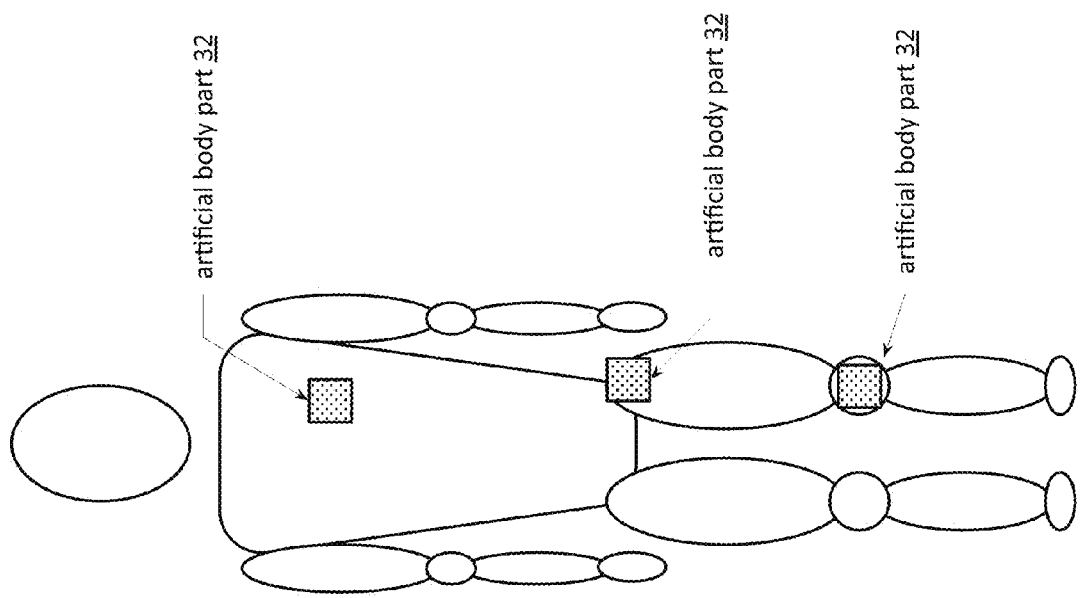
FIG. 3 is a diagram of an embodiment of an artificial body part including one or more bio-medical units in accordance with the present invention.

FIG. 3 is a diagram of an embodiment of an artificial body part 32 including one or more bio-medical units 10 that may be surgically implanted into a body. The artificial body part 32 may be a pace maker, a breast implant, a joint replacement, an artificial bone, splints, fastener devices (e.g., screws, plates, pins, sutures, etc.), artificial organ, etc. The artificial body part 32 may be permanently embedded in the body or temporarily embedded into the body.

Figure 4:
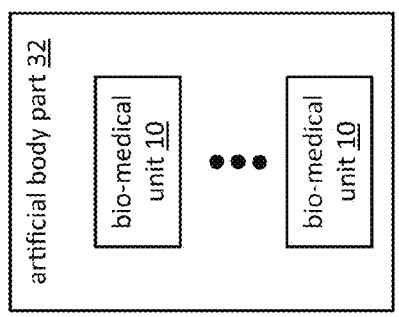
FIG. 4 is a schematic block diagram of an embodiment of an artificial body part in accordance with the present invention.

FIG. 4 is a schematic block diagram of an embodiment of an artificial body part 32 that includes one or more bio-medical units 10. For instance, one bio-medical unit 10 may be used to detect infections, the body's acceptance of the artificial body part 32, measure localized body temperature, monitor performance of the artificial body part 32, and/or data gathering for other diagnostics. Another bio-medical unit 10 may be used for deployment of treatment (e.g., disperse medication, apply electrical stimulus, apply RF radiation, apply laser stimulus, etc.). Yet another bio-medical unit 10 may be used to adjust the position of the artificial body part 32 and/or a setting of the artificial body part 32. For example, a bio-medical unit 10 may be used to mechanically adjust the tension of a splint, screws, etc. As another example, a bio-medical unit 10 may be used to adjust an electrical setting of the artificial body part 32.

Figure 5:
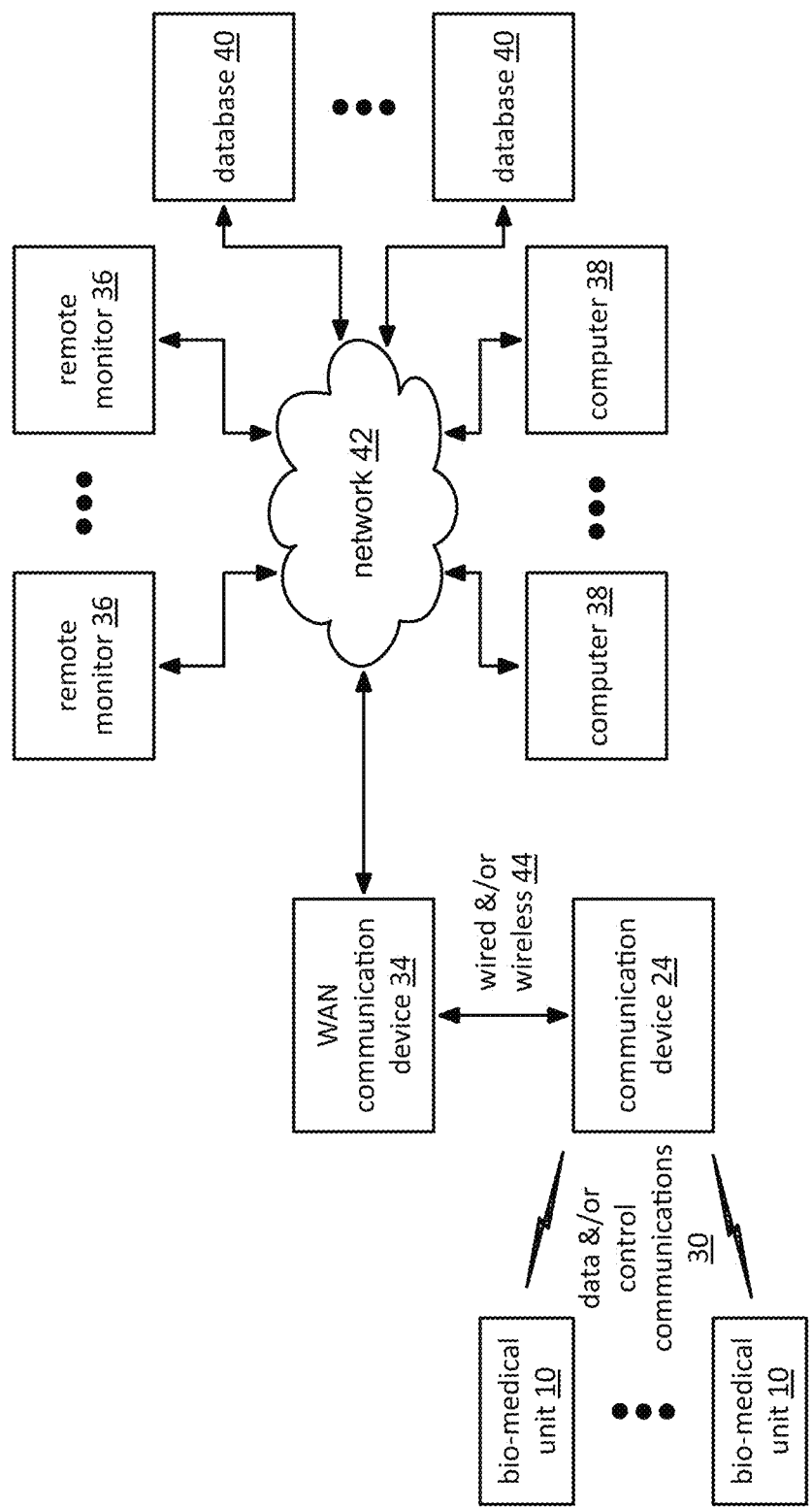
FIG. 5 is a diagram of another embodiment of a system in accordance with the present invention.

FIG. 5 is a diagram of another embodiment of a system that includes a plurality of bio-medical units 10 and one or more communication devices 24 coupled to a wide area network (WAN) communication device 34 (e.g., a cable modem, DSL modem, base station, access point, hot spot, etc.). The WAN communication device 34 is coupled to a network 42 (e.g., cellular telephone network, internet, etc.), which has coupled to it a plurality of remote monitors 36, a plurality of databases 40, and a plurality of computers 38. The communication device 24 includes a processing module and a wireless transceiver module (e.g., one or more transceivers) and may function similarly to communication module 48 as described in FIG. 8.

In this system, one or more bio-medical units 10 are implanted in, or affixed to, a host body (e.g., a person, an animal, genetically grown tissue, etc.). As previously discussed and will be discussed in greater detail with reference to one or more of the following figures, a bio-medical unit includes a power harvesting module, a communication module, and one or more functional modules. The power harvesting module operable to produce a supply voltage from a received electromagnetic power signal (e.g., the electromagnetic signal 16 of FIGS. 1 and 2, the MRI signals of one or more the subsequent figures). The communication module and the at least one functional module are powered by the supply voltage.

In an example of operation, the communication device 24 (e.g., integrated into an MRI machine, a cellular telephone, a computer with a wireless interface, etc.) receives a downstream WAN signal from the network 42 via the WAN communication device 34. The downstream WAN signal may be generated by a remote monitoring device 36, a remote diagnostic device (e.g., computer 38 performing a remote diagnostic function), a remote control device (e.g., computer 38 performing a remote control function), and/or a medical record storage device (e.g., database 40).

The communication device 24 converts the downstream WAN signal into a downstream data signal. For example, the communication device 24 may convert the downstream WAN signal into a symbol stream in accordance with one or more wireless communication protocols (e.g., GSM, CDMA, WCDMA, HSUPA, HSDPA, WiMAX, EDGE, GPRS, IEEE 802.11, Bluetooth, ZigBee, universal mobile telecommunications system (UMTS), long term evolution (LTE), IEEE 802.16, evolution data optimized (EV-DO), etc.). The communication device 24 may convert the symbol stream into the downstream data signal using the same or a different wireless communication protocol.

Alternatively, the communication device 24 may convert the symbol stream into data that it interprets to determine how to structure the communication with the bio-medical unit 10 and/or what data (e.g., instructions, commands, digital information, etc.) to include in the downstream data signal. Having determined how to structure and what to include in the downstream data signal, the communication device 24 generates the downstream data signal in accordance with one or more wireless communication protocols. As yet another alternative, the communication device 24 may function as a relay, which provides the downstream WAN signal as the downstream data signal to the one or more bio-medical units 10.

When the communication device 24 has (and/or is processing) the downstream data signal to send to the bio-medical unit, it sets up a communication with the bio-medical unit. The set up may include identifying the particular bio-medical unit(s), determining the communication protocol used by the identified bio-medical unit(s), sending a signal to an electromagnetic device (e.g., MRI device, etc.) to request that it generates the electromagnetic power signal to power the bio-medical unit, and/or initiate a communication in accordance with the identified communication protocol. As an alternative to requesting a separate electromagnetic device to create the electromagnetic power signal, the communication device may include an electromagnetic device to create the electromagnetic power signal.

Having set up the communication, the communication device 24 wirelessly communicates the downstream data signal to the communication module of the bio-medical unit 10. The functional module of the bio-medical unit 10 processes the downstream data contained in the downstream data signal to perform a bio-medical functional, to store digital information contained in the downstream data, to administer a treatment (e.g., administer a medication, apply laser stimulus, apply electrical stimulus, etc.), to collect a sample (e.g., blood, tissue, cell, etc.), to perform a micro electro-mechanical function, and/or to collect data. For example, the bio-medical function may include capturing a digital image, capturing a radio frequency (e.g., 300 MHz to 300 GHz) radar image, an ultrasound image, a tissue sample, and/or a measurement (e.g., blood pressure, temperature, pulse, blood-oxygen level, blood sugar level, etc.).

When the downstream data requires a response, the functional module performs a bio-medical function to produce upstream data. The communication module converts the upstream data into an upstream data signal in accordance with the one or more wireless protocols. The communication device 24 converts the upstream data signal into an upstream wide area network (WAN) signal and transmits it to a remote diagnostic device, a remote control device, and/or a medical record storage device. In this manner, a person(s) operating the remote monitors 36 may view images and/or the data 30 gathered by the bio-medical units 10. This enables a specialist to be consulted without requiring the patient to travel to the specialist's office.

In another example of operation, one or more of the computers 38 may communicate with the bio-medical units 10 via the communication device 24, the WAN communication device 34, and the network 42. In this example, the computer 36 may provide commands 30 to one or more of the bio-medical units 10 to gather data, to dispense a medication, to move to a new position in the body, to perform a mechanical function (e.g., cut, grasp, drill, puncture, stitch, patch, etc.), etc. As such, the bio-medical units 10 may be remotely controlled via one or more of the computers 36.

In another example of operation, one or more of the bio-medical units 10 may read and/or write data from or to one or more of the databases 40. For example, data (e.g., a blood sample analysis) generated by one or more of the bio-medical units 10 may be written to one of the databases 40. The communication device 24 and/or one of the computers 36 may control the writing of data to or the reading of data from the database(s) 40. The data may further include medical records, medical images, prescriptions, etc.

Figure 6:
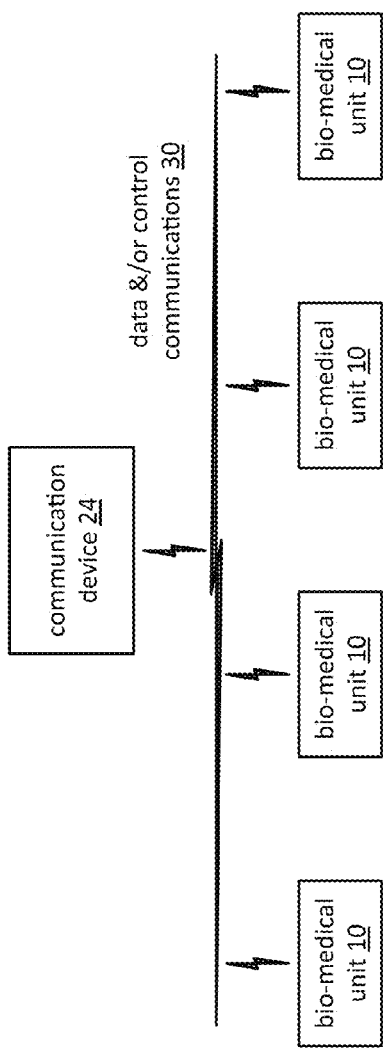
FIG. 6 is a diagram of another embodiment of a system in accordance with the present invention.

FIG. 6 is a diagram of another embodiment of a system that includes a plurality of bio-medical units 10. In this embodiment, the bio-medical units 10 can communicate with each other directly and/or communicate with the communication device 24 directly. The communication medium may be an infrared channel(s), an RF channel(s), a MMW channel(s), and/or ultrasound. The units may use a communication protocol such as token passing, carrier sense, time division multiplexing, code division multiplexing, frequency division multiplexing, etc.

Figure 7:
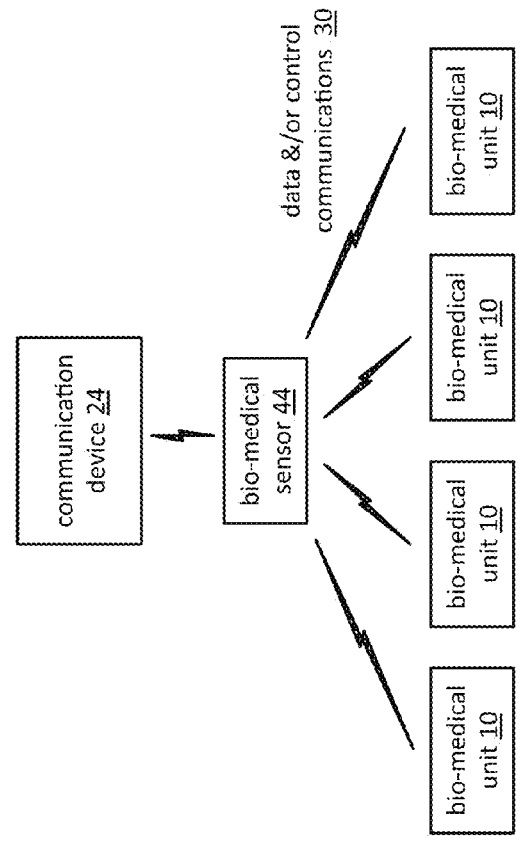
FIG. 7 is a diagram of another embodiment of a system in accordance with the present invention.

FIG. 7 is a diagram of another embodiment of a system that includes a plurality of bio-medical units 10. In this embodiment, one of the bio-medical units 44 functions as an access point for the other units. As such, the designated unit 44 routes communications between the units 10 and between one or more units 10 and the communication device 24. The communication medium may be an infrared channel(s), an RF channel(s), a MMW channel(s), and/or ultrasound. The units 10 may use a communication protocol such as token passing, carrier sense, time division multiplexing, code division multiplexing, frequency division multiplexing, etc.

Figure 8:
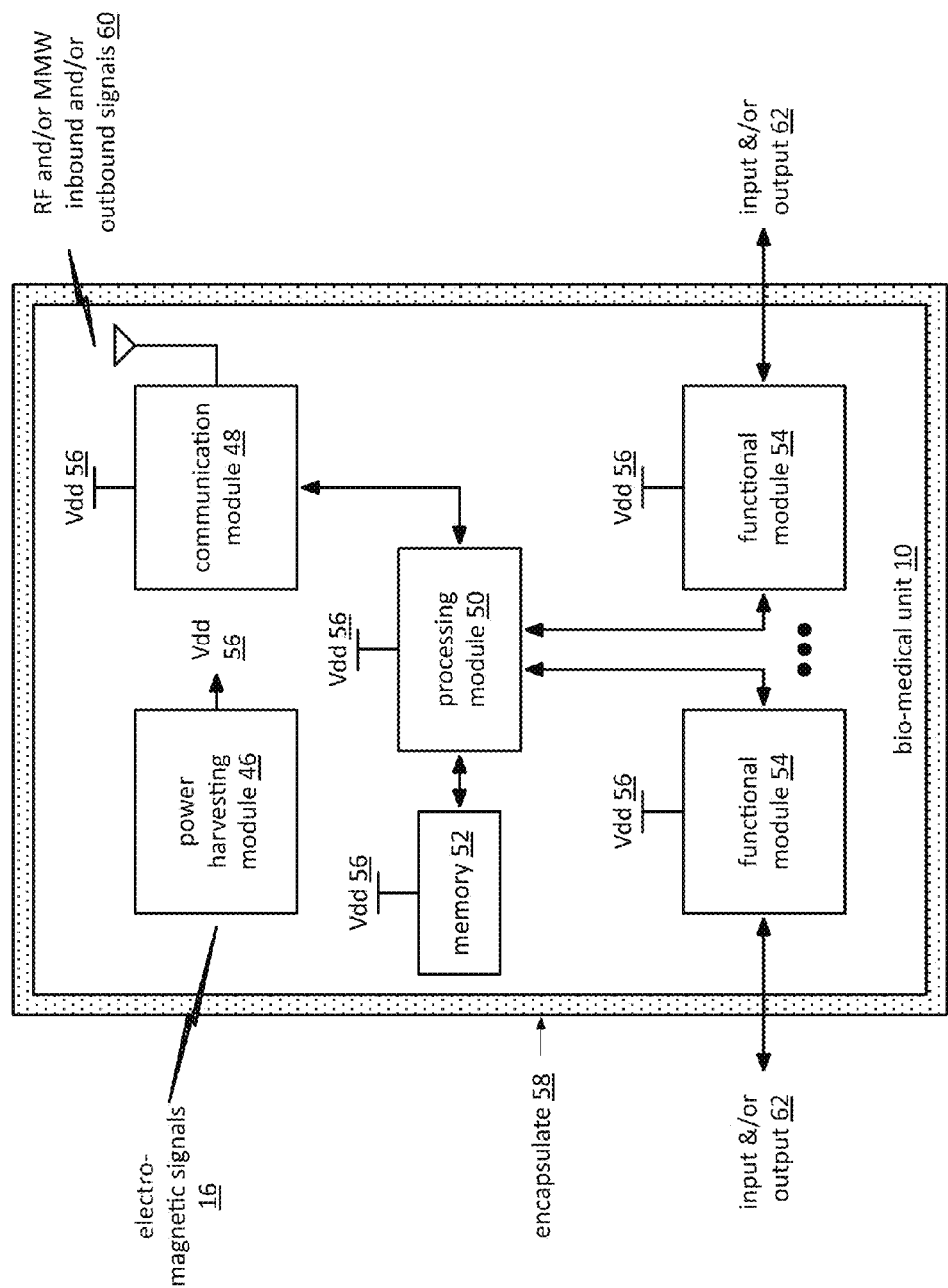
FIG. 8 is a schematic block diagram of an embodiment of a bio-medical unit in accordance with the present invention.

FIG. 8 is a schematic block diagram of an embodiment of a bio-medical unit 10 that includes a power harvesting module 46, a communication module 48, a processing module 50, memory 52, and one or more functional modules 54. The processing module 50 may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing module 50 may have an associated memory 52 and/or memory element, which may be a single memory device, a plurality of memory devices, and/or embedded circuitry of the processing module. Such a memory device 52 may be a read-only memory, random access memory, volatile memory, non-volatile memory, static memory, dynamic memory, flash memory, cache memory, and/or any device that stores digital information. Note that if the processing module 50 includes more than one processing device, the processing devices may be centrally located (e.g., directly coupled together via a wired and/or wireless bus structure) or may be distributedly located (e.g., cloud computing via indirect coupling via a local area network and/or a wide area network). Further note that when the processing module 50 implements one or more of its functions via a state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Still further note that, the memory element stores, and the processing module executes, hard coded and/or operational instructions corresponding to at least some of the steps and/or functions illustrated in FIGS. 1-29.

The power harvesting module 46 may generate one or more supply voltages 56 (Vdd) from a power source signal (e.g., one or more MRI electromagnetic signals 16, magnetic fields 26, RF signals, MMW signals, ultrasound signals, light signals, and body motion). The power harvesting module 46 may be implemented as disclosed in U.S. Pat. No. 7,595,732 to generate one or more supply voltages from an RF signal. The power harvesting module 46 may be implemented as shown in one or more FIGS. 9-11 to generate one or more supply voltages 56 from an MRI signal 28 and/or magnetic field 26. The power harvesting module 46 may be implemented as shown in FIG. 12 to generate one or more supply voltage 56 from body motion. Regardless of how the power harvesting module generates the supply voltage(s), the supply voltage(s) are used to power the communication module 48, the processing module 50, the memory 52, and/or the functional modules 54.

In an example of operation, a receiver section of the communication module 48 receives an inbound wireless communication signal 60 and converts it into an inbound symbol stream. For example, the receiver section amplifies an inbound wireless (e.g., RF or MMW) signal 60 to produce an amplified inbound RF or MMW signal. The receiver section may then mix in-phase (I) and quadrature (Q) components of the amplified inbound RF or MMW signal with in-phase and quadrature components of a local oscillation to produce a mixed I signal and a mixed Q signal. The mixed I and Q signals are combined to produce an inbound symbol stream. In this embodiment, the inbound symbol may include phase information (e.g., +/−Δθ [phase shift] and/or θ(t) [phase modulation]) and/or frequency information (e.g., +/−Δf [frequency shift] and/or f(t) [frequency modulation]). In another embodiment and/or in furtherance of the preceding embodiment, the inbound RF or MMW signal includes amplitude information (e.g., +/−ΔA [amplitude shift] and/or A(t) [amplitude modulation]). To recover the amplitude information, the receiver section includes an amplitude detector such as an envelope detector, a low pass filter, etc.

The processing module 50 converts the inbound symbol stream into inbound data and generates a command message based on the inbound data. The command message may instruction one or more of the functional modules to perform one or more electro-mechanical functions of gathering data, dispensing a medication, moving to a new position in the body, performing a mechanical function (e.g., cut, grasp, drill, puncture, stitch, patch, etc.), dispensing a treatment, collecting a biological sample, etc.

To convert the inbound symbol stream into the inbound data (e.g., voice, text, audio, video, graphics, etc.), the processing module 50 may perform one or more of: digital intermediate frequency to baseband conversion, time to frequency domain conversion, space-time-block decoding, space-frequency-block decoding, demodulation, frequency spread decoding, frequency hopping decoding, beamforming decoding, constellation demapping, deinterleaving, decoding, depuncturing, and/or descrambling. Such a conversion is typically prescribed by one or more wireless communication standards (e.g., GSM, CDMA, WCDMA, HSUPA, HSDPA, WiMAX, EDGE, GPRS, IEEE 802.11, Bluetooth, ZigBee, universal mobile telecommunications system (UMTS), long term evolution (LTE), IEEE 802.16, evolution data optimized (EV-DO), etc.).

The processing module 50 provides the command message to one or more of the micro-electromechanical functional modules 54. The functional module 54 performs an electro-mechanical function within a hosting body in accordance with the command message. Such an electro-mechanical function includes at least one of data gathering, motion, repairs, dispensing medication, biological sampling, diagnostics, applying laser treatment, applying ultrasound treatment, grasping, sawing, drilling, providing an electronic stimulus etc. Note that the functional modules 54 may be implemented using nanotechnology and/or microelectronic mechanical systems (MEMS) technology.

When requested per the command message (e.g. gather data and report the data), the micro electro-mechanical functional module 54 generates an electro-mechanical response based on the performing the electro-mechanical function. For example, the response may be data (e.g., heart rate, blood sugar levels, temperature, etc.), a biological sample (e.g., blood sample, tissue sample, etc.), acknowledgement of performing the function (e.g., acknowledge a software update, storing of data, etc.), and/or any appropriate response. The micro electro-mechanical functional module 54 provides the response to the processing module 50.

The processing module 50 converts the electro-mechanical response into an outbound symbol stream, which may be done in accordance with one or more wireless communication standards (e.g., GSM, CDMA, WCDMA, HSUPA, HSDPA, WiMAX, EDGE, GPRS, IEEE 802.11, Bluetooth, ZigBee, universal mobile telecommunications system (UMTS), long term evolution (LTE), IEEE 802.16, evolution data optimized (EV-DO), etc.). Such a conversion includes one or more of: scrambling, puncturing, encoding, interleaving, constellation mapping, modulation, frequency spreading, frequency hopping, beamforming, space-time-block encoding, space-frequency-block encoding, frequency to time domain conversion, and/or digital baseband to intermediate frequency conversion.

A transmitter section of the communication module 48 converts an outbound symbol stream into an outbound RF or MMW signal 60 that has a carrier frequency within a given frequency band (e.g., 900 MHz, 2.5 GHz, 5 GHz, 57-66 GHz, etc.). In an embodiment, this may be done by mixing the outbound symbol stream with a local oscillation to produce an up-converted signal. One or more power amplifiers and/or power amplifier drivers amplifies the up-converted signal, which may be RF or MMW bandpass filtered, to produce the outbound RF or MMW signal 60. In another embodiment, the transmitter section includes an oscillator that produces an oscillation. The outbound symbol stream provides phase information (e.g., +/−Δθ [phase shift] and/or θ(t) [phase modulation]) that adjusts the phase of the oscillation to produce a phase adjusted RF or MMW signal, which is transmitted as the outbound RF signal 60. In another embodiment, the outbound symbol stream includes amplitude information (e.g., A(t) [amplitude modulation]), which is used to adjust the amplitude of the phase adjusted RF or MMW signal to produce the outbound RF or MMW signal 60.

In yet another embodiment, the transmitter section includes an oscillator that produces an oscillation. The outbound symbol provides frequency information (e.g., +/−Δf [frequency shift] and/or f(t) [frequency modulation]) that adjusts the frequency of the oscillation to produce a frequency adjusted RF or MMW signal, which is transmitted as the outbound RF or MMW signal 60. In another embodiment, the outbound symbol stream includes amplitude information, which is used to adjust the amplitude of the frequency adjusted RF or MMW signal to produce the outbound RF or MMW signal 60. In a further embodiment, the transmitter section includes an oscillator that produces an oscillation. The outbound symbol provides amplitude information (e.g., +/−ΔA [amplitude shift] and/or A(t) [amplitude modulation]) that adjusts the amplitude of the oscillation to produce the outbound RF or MMW signal 60.

Note that the bio-medical unit 10 may be encapsulated by an encapsulate 58 that is non-toxic to the body. For example, the encapsulate 58 may be a silicon based product, a non-ferromagnetic metal alloy (e.g., stainless steel), etc. As another example, the encapsulate 58 may include a spherical shape and have a ferromagnetic liner that shields the unit from a magnetic field and to offset the forces of the magnetic field. Further note that the bio-medical unit 10 may be implemented on a single die that has an area of a few millimeters or less. The die may be fabricated in accordance with CMOS technology, Gallium-Arsenide technology, and/or any other integrated circuit die fabrication process.

Figure 9:
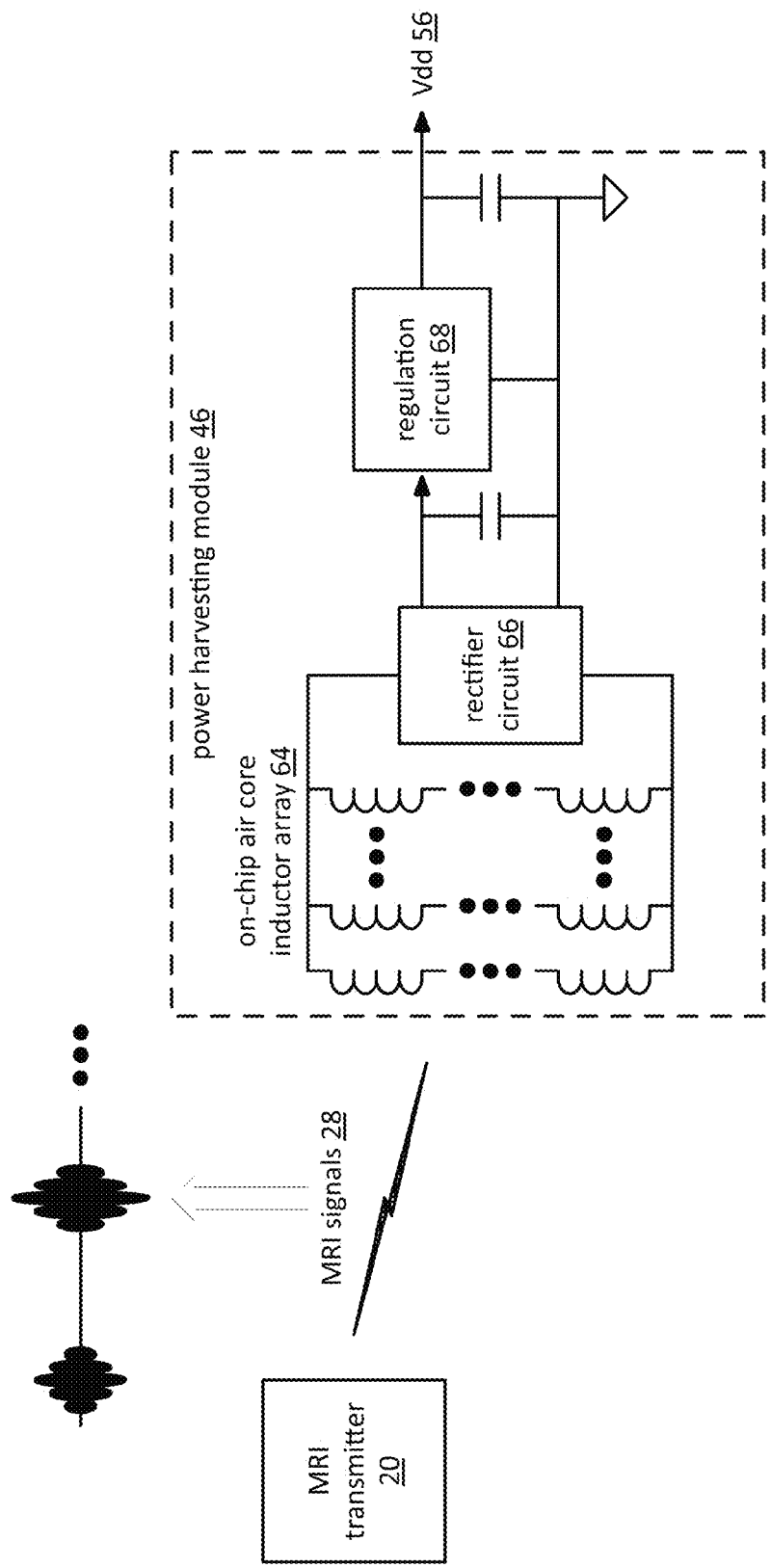
FIG. 9 is a schematic block diagram of an embodiment of a power harvesting module in accordance with the present invention.

FIG. 9 is a schematic block diagram of an embodiment of a power harvesting module 46 that includes an array of on-chip air core inductors 64, a rectifying circuit 66, capacitors, and a regulation circuit 68. The inductors 64 may each having an inductance of a few nano-Henries to a few micro-Henries and may be coupled in series, in parallel, or a series parallel combination.

In an example of operation, the MRI transmitter 20 transmits MRI signals 28 at a frequency of 3-45 MHz at a power level of up to 35 KWatts. The air core inductors 64 are electromagnetically coupled to generate a voltage from the magnetic and/or electric field generated by the MRI signals 28. Alternatively or in addition to, the air core inductors 64 may generate a voltage from the magnetic field 26 and changes thereof produced by the gradient coils. The rectifying circuit 66 rectifies the AC voltage produced by the inductors to produce a first DC voltage. The regulation circuit generates one or more desired supply voltages 56 from the first DC voltage.

The inductors 64 may be implemented on one more metal layers of the die and include one or more turns per layer. Note that trace thickness, trace length, and other physical properties affect the resulting inductance.

Figure 10:
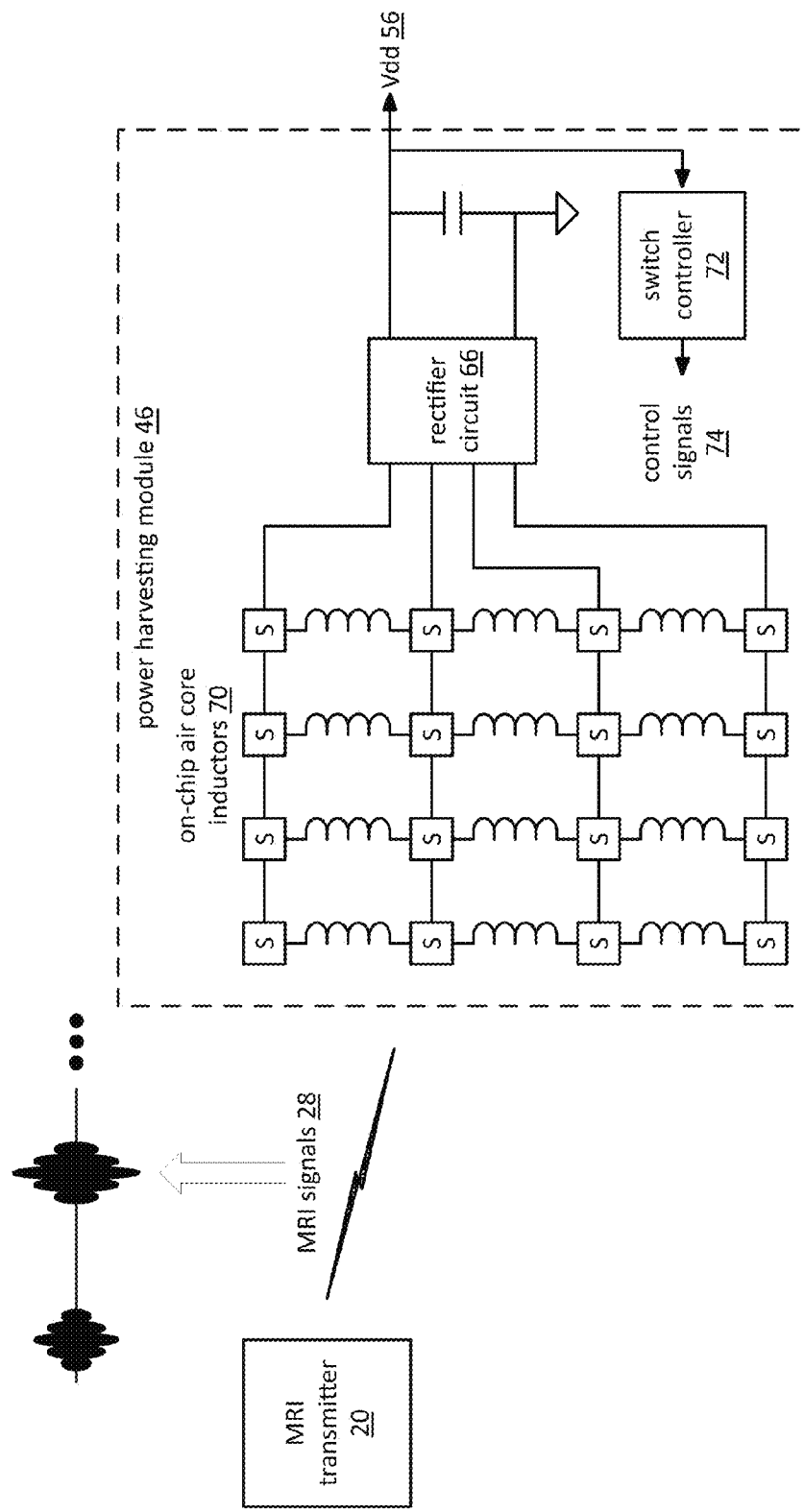
FIG. 10 is a schematic block diagram of another embodiment of a power harvesting module in accordance with the present invention.

FIG. 10 is a schematic block diagram of another embodiment of a power harvesting module 46 that includes a plurality of on-chip air core inductors 70, a plurality of switching units (S), a rectifying circuit 66, a capacitor, and a switch controller 72. The inductors 70 may each having an inductance of a few nano-Henries to a few micro-Henries and may be coupled in series, in parallel, or a series parallel combination.

In an example of operation, the MRI transmitter 20 transmits MRI signals 28 at a frequency of 3-45 MHz at a power level of up to 35 KWatts. The air core inductors 70 are electromagnetically coupled to generate a voltage from the magnetic and/or electric field generated by the MRI signals 28. The switching module 72 engages the switches via control signals 74 to couple the inductors 70 in series and/or parallel to generate a desired AC voltage. The rectifier circuit 66 and the capacitor(s) convert the desired AC voltage into the one or more supply voltages 56.

Figure 11:
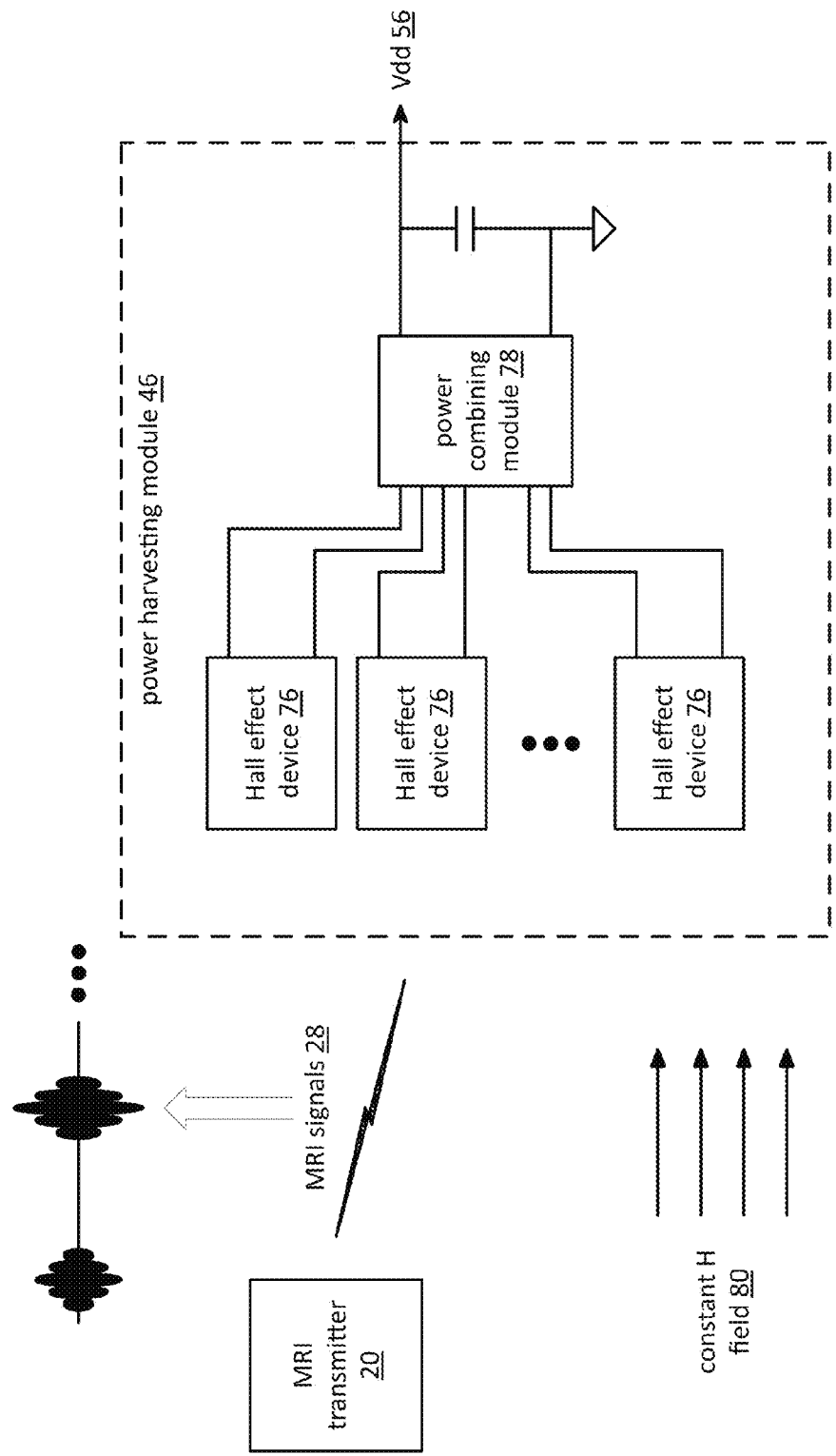
FIG. 11 is a schematic block diagram of another embodiment of a power harvesting module in accordance with the present invention.
Figure 12:
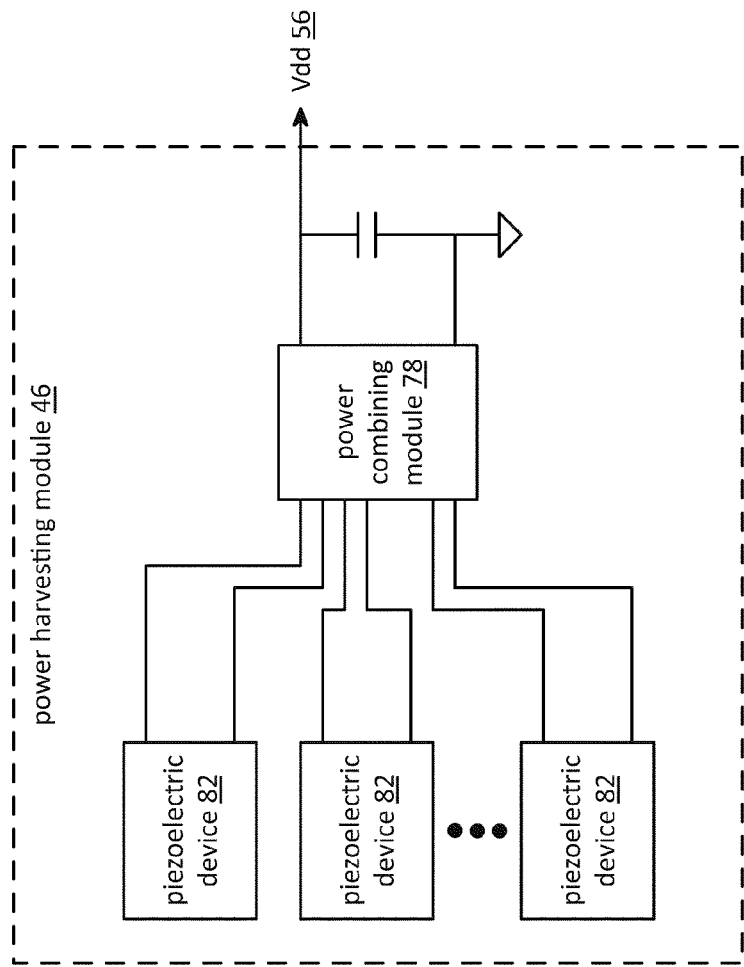
FIG. 12 is a schematic block diagram of another embodiment of a power harvesting module in accordance with the present invention.

FIG. 11 is a schematic block diagram of another embodiment of a power harvesting module 46 that includes a plurality of Hall effect devices 76, a power combining module 78, and a capacitor(s). In an example of operation, the Hall effect devices 76 generate a voltage based on the constant magnetic field (H) and/or a varying magnetic field. The power combining module 78 (e.g., a wire, a switch network, a transistor network, a diode network, etc.) combines the voltages of the Hall effect devices 76 to produce the one or more supply voltages 56.

FIG. 12 is a schematic block diagram of another embodiment of a power harvesting module 46 that includes a plurality of piezoelectric devices 82, a power combining module 78, and a capacitor(s). In an example of operation, the piezoelectric devices 82 generate a voltage based on body movement, ultrasound signals, movement of body fluids, etc. The power combining module 78 (e.g., a wire, a switch network, a transistor network, a diode network, etc.) combines the voltages of the Hall effect devices 82 to produce the one or more supply voltages 56. Note that the piezoelectric devices 82 may include one or more of a piezoelectric motor, a piezoelectric actuator, a piezoelectric sensor, and/or a piezoelectric high voltage device.

The various embodiments of the power harvesting module 46 may be combined to generate more power, more supply voltages, etc. For example, the embodiment of FIG. 9 may be combined with one or more of the embodiments of FIGS. 11 and 12.

FIG. 13 is a schematic block diagram of an embodiment of a power boost module 84 that harvests energy from MRI signals 28 and converts the energy into continuous wave (CW) RF (e.g., up to 3 GHz) and/or MMW (e.g., up to 300 GHz) signals 92 to provide power to the implanted bio-medical units 10. The power boost module 84 sits on the body of the person under test or treatment and includes an electromagnetic power harvesting module 86 and a continuous wave generator 88. In such an embodiment, the power boosting module 84 can recover significantly more energy than a bio-medical unit 10 since it can be significantly larger. For example, a bio-medical unit 10 may have an area of a few millimeters squared while the power boosting module 84 may have an area of a few to tens of centimeters squared.

FIG. 14 is a schematic block diagram of an embodiment of an electromagnetic (EM) power harvesting module 86 that includes inductors, diodes (or transistors) and a capacitor. The inductors may each be a few milli-Henries such that the power boost module can deliver up to 10's of milli-watts of power.

FIG. 15 is a schematic block diagram of another embodiment of an EM power harvesting module 86 that includes a plurality of Hall effect devices 76, a power combining module 78, and a capacitor. This functions as described with reference to FIG. 11, but the Hall effect devices 76 can be larger such that more power can be produced. Note that the EM power harvesting module 86 may include a combination of the embodiment of FIG. 14 and the embodiment of FIG. 15.

Figure 16:
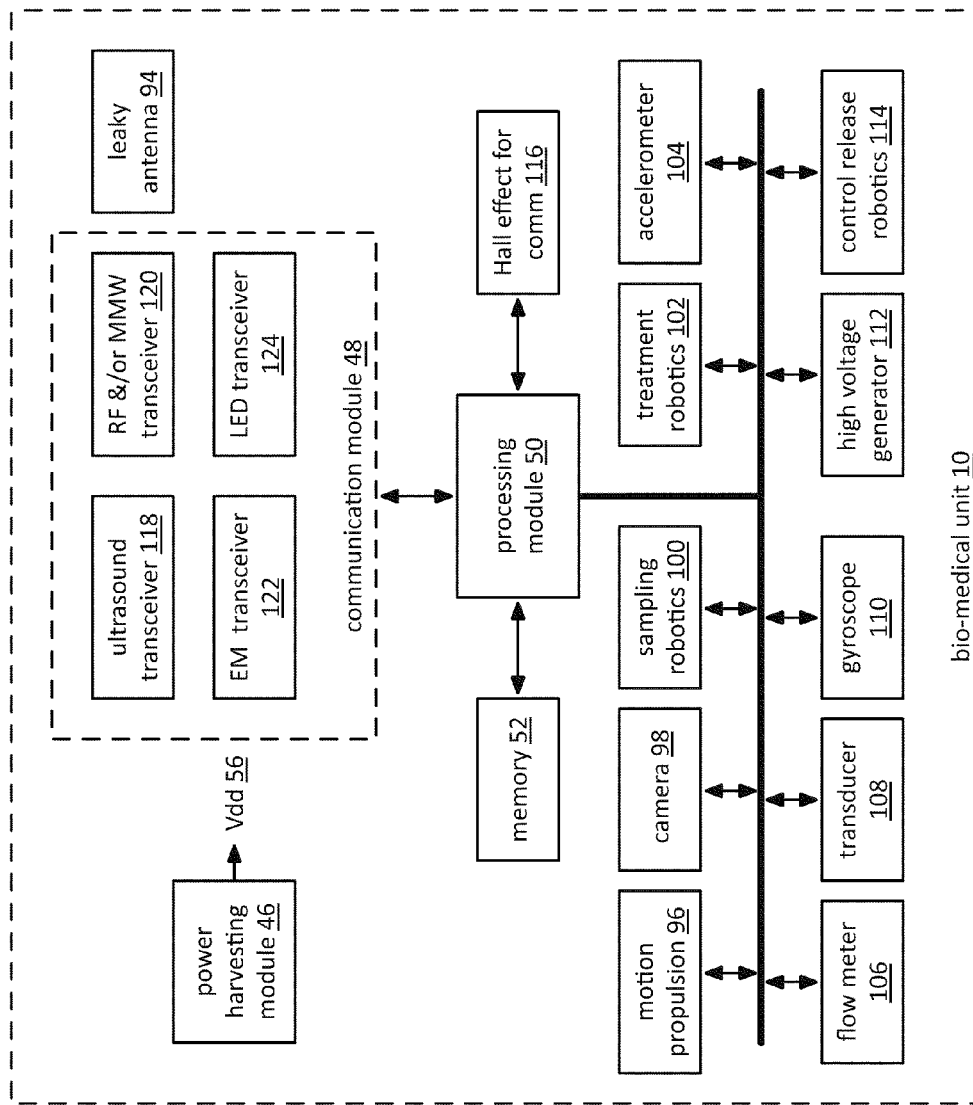
FIG. 16 is a schematic block diagram of another embodiment of a bio-medical unit in accordance with the present invention.

FIG. 16 is a schematic block diagram of another embodiment of a bio-medical unit 10 that includes a power harvesting module 46, a communication module 48, a processing module 50, memory 52, and may include one or more functional modules 54 and/or a Hall effect communication module 116. The communication module 48 may include one or more of an ultrasound transceiver 118, an electromagnetic transceiver 122, an RF and/or MMW transceiver 120, and a light source (LED) transceiver 124. Note that examples of the various types of communication modules 48 will be described in greater detail with reference to one or more of FIGS. 14-49.

The one or more functional modules 54 may perform a repair function, an imaging function, and/or a leakage detection function, which may utilize one or more of a motion propulsion module 96, a camera module 98, a sampling robotics module 100, a treatment robotics module 102, an accelerometer module 104, a flow meter module 106, a transducer module 108, a gyroscope module 110, a high voltage generator module 112, a control release robotics module 114, and/or other functional modules described with reference to one or more other figures. The functional modules 54 may be implemented using MEMS technology and/or nanotechnology. For example, the camera module 98 may be implemented as a digital image sensor in MEMS technology.

The Hall effect communication module 116 utilizes variations in the magnetic field and/or electrical field to produce a plus or minus voltage, which can be encoded to convey information. For example, the charge applied to one or more Hall effect devices 76 may be varied to produce the voltage change. As another example, an MRI transmitter 20 and/or gradient unit may modulate a signal on the magnetic field 26 it generates to produce variations in the magnetic field 26.

Figure 17:
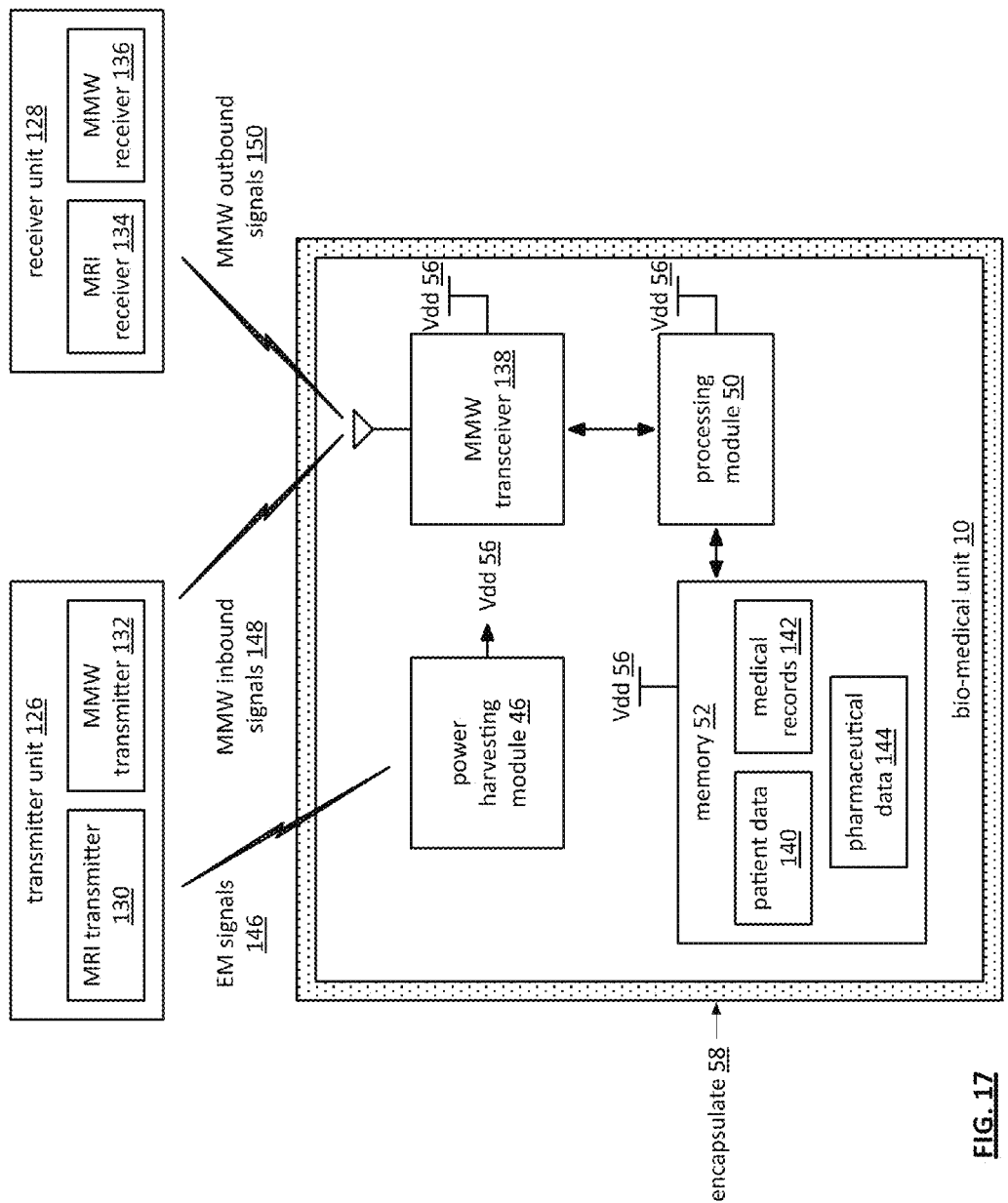
FIG. 17 is a diagram of another embodiment of a system in accordance with the present invention.

FIG. 17 is a diagram of another embodiment of a system that includes one or more bio-medical units 10, a transmitter unit 126, and a receiver unit 128. Each of the bio-medical units 10 includes a power harvesting module 46, a MMW transceiver 138, a processing module 50, and memory 52. The transmitter unit 126 includes a MRI transmitter 130 and a MMW transmitter 132. The receiver unit 128 includes a MRI receiver 134 and a MMW receiver 136. Note that the MMW transmitter 132 and MMW receiver 136 may be in the same unit (e.g., in the transmitter unit, in the receiver unit, or housed in a separate device).

In an example of operation, the bio-medical unit 10 recovers power from the electromagnetic (EM) signals 146 transmitted by the MRI transmitter 130 and communicates via MMW signals 148-150 with the MMW transmitter 132 and MMW receiver 136. The MRI transmitter 130 may be part of a portable MRI device, may be part of a full sized MRI machine, and/or part of a separate device for generating EM signals 146 for powering the bio-medical unit 10.

Figure 18:
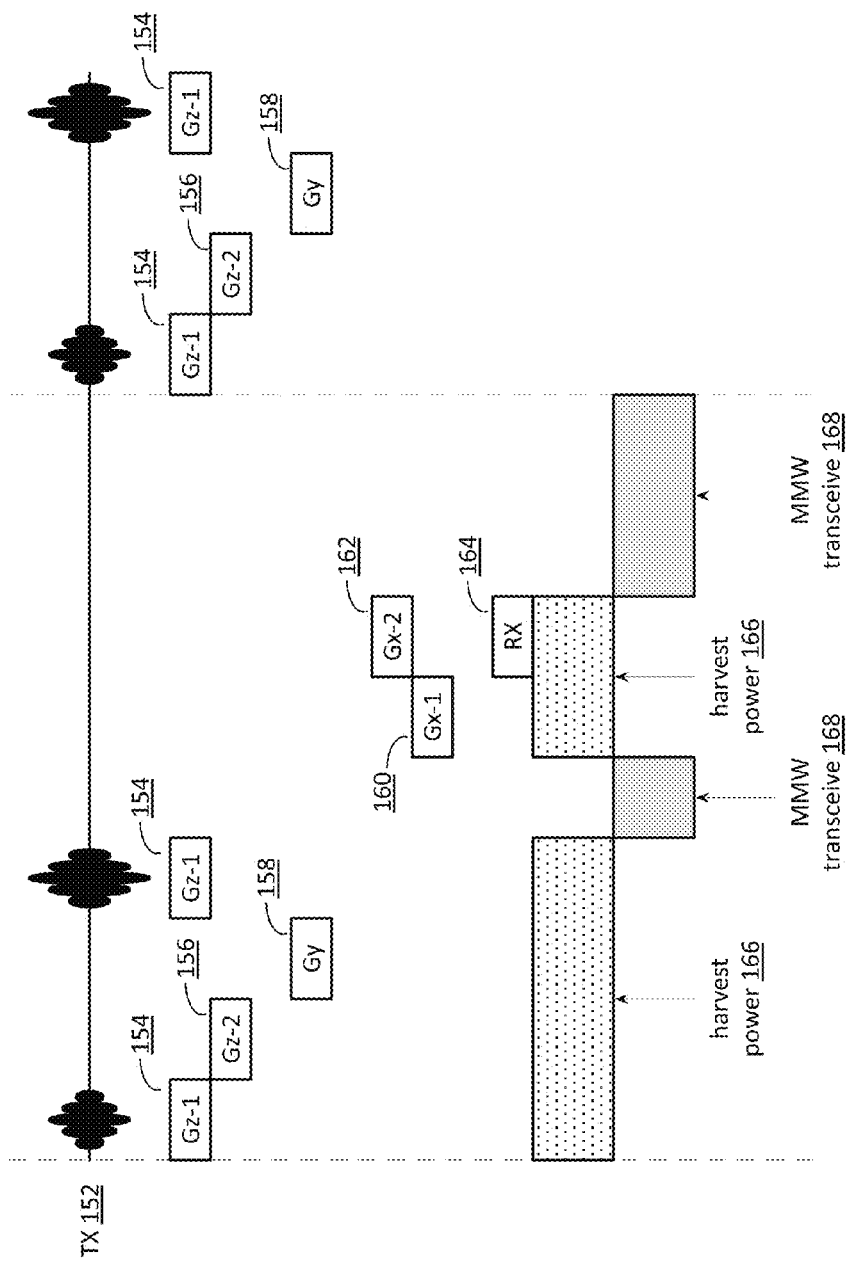
FIG. 18 is a diagram of an example of a communication protocol within a system in accordance with the present invention.

FIG. 18 is a diagram of an example of a communication protocol within the system of FIG. 17. In this diagram, the MRI transmitter 20 transmits RF signals 152, which have a frequency in the range of 3-45 MHz, at various intervals with varying signal strengths. The power harvesting module 46 of the bio-medical units 10 may use these signals to generate power for the bio-medical unit 10.

In addition to the MRI transmitter 20 transmitting its signal, a constant magnetic field and various gradient magnetic fields 154-164 are created (one or more in the x dimension Gx, one or more in the y dimension Gy, and one or more in the z direction Gz). The power harvesting module 46 of the bio-medical unit 10 may further use the constant magnetic field and/or the varying magnetic fields 154-164 to create power for the bio-medical unit 10.

During non-transmission periods of the cycle, the bio-medical unit 10 may communicate 168 with the MMW transmitter 132 and/or MMW receiver 136. In this regard, the bio-medical unit 10 alternates from generating power to MMW communication in accordance with the conventional transmission-magnetic field pattern of an MRI machine.

Figure 19:
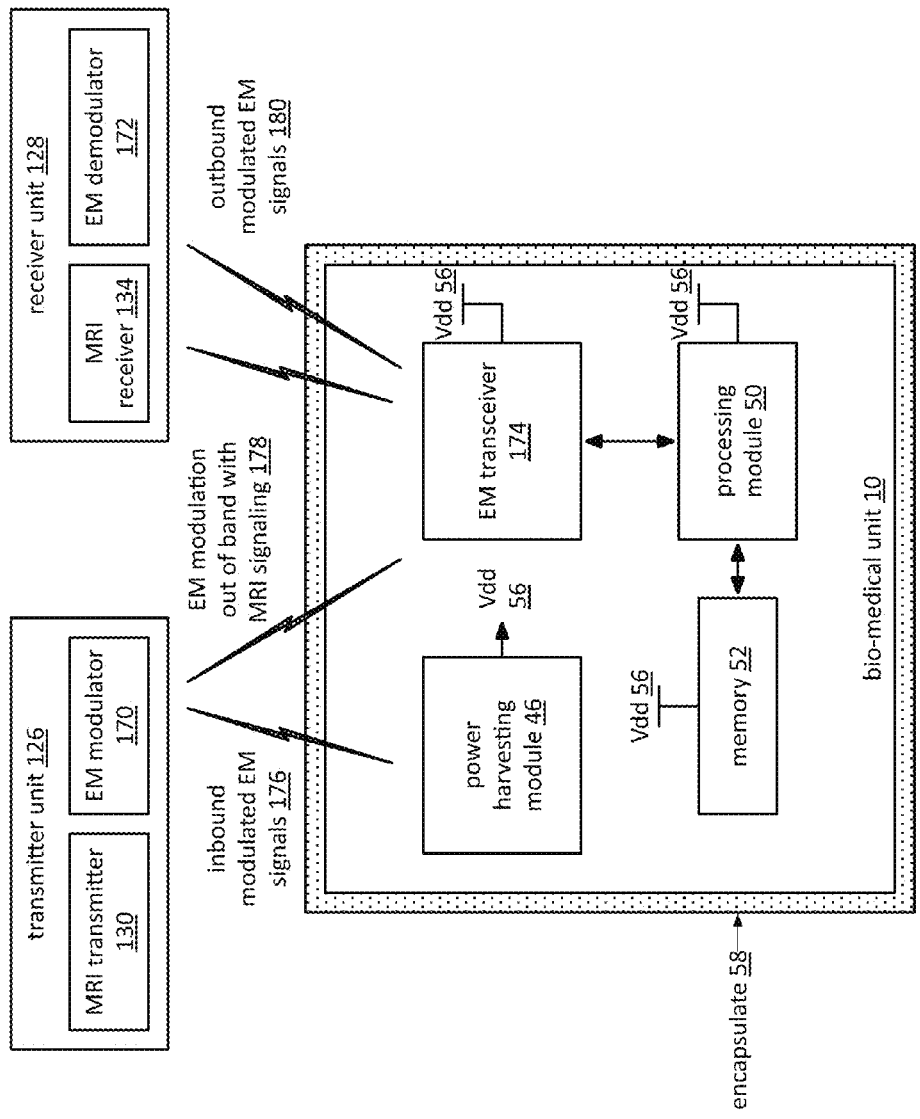
FIG. 19 is a diagram of another embodiment of a system in accordance with the present invention.

FIG. 19 is a diagram of another embodiment of a system includes one or more bio-medical units 10, a transmitter unit 126, and a receiver unit 128. Each of the bio-medical units 10 includes a power harvesting module 46, an EM transceiver 174, a processing module 50, and memory 52. The transmitter unit 126 includes a MRI transmitter 130 and electromagnetic (EM) modulator 170. The receiver unit 128 includes a MRI receiver 134 and a EM demodulator 172. The transmitter unit 126 and receiver unit 128 may be part of a portable MRI device, may be part of a full sized MRI machine, or part of a separate device for generating EM signals for powering the bio-medical unit 10.

In an example of operation, the MRI transmitter 130 generates an electromagnetic signal that is received by the EM modulator 170. The EM modulator 170 modulates a communication signal on the EM signal to produce an inbound modulated EM signal 176. The EM modulator 170 may modulate (e.g., amplitude modulation, frequency modulation, amplitude shift keying, frequency shift keying, etc.) the magnetic field and/or electric field of the EM signal. In another embodiment, the EM modulator 170 may modulate the magnetic fields produced by the gradient coils to produce the inbound modulated EM signals 176.

The bio-medical unit 10 recovers power from the modulated electromagnetic (EM) signals. In addition, the EM transceiver 174 demodulates the modulated EM signals 178 to recover the communication signal. For outbound signals, the EM transceiver 174 modulates an outbound communication signal to produce outbound modulated EM signals 180. In this instance, the EM transceiver 174 is generating an EM signal that, in air, is modulated on the EM signal transmitted by the transmitter unit 126. In one embodiment, the communication in this system is half duplex such that the modulation of the inbound and outbound communication signals is at the same frequency. In another embodiment, the modulation of the inbound and outbound communication signals are at different frequencies to enable full duplex communication.

Figure 20:
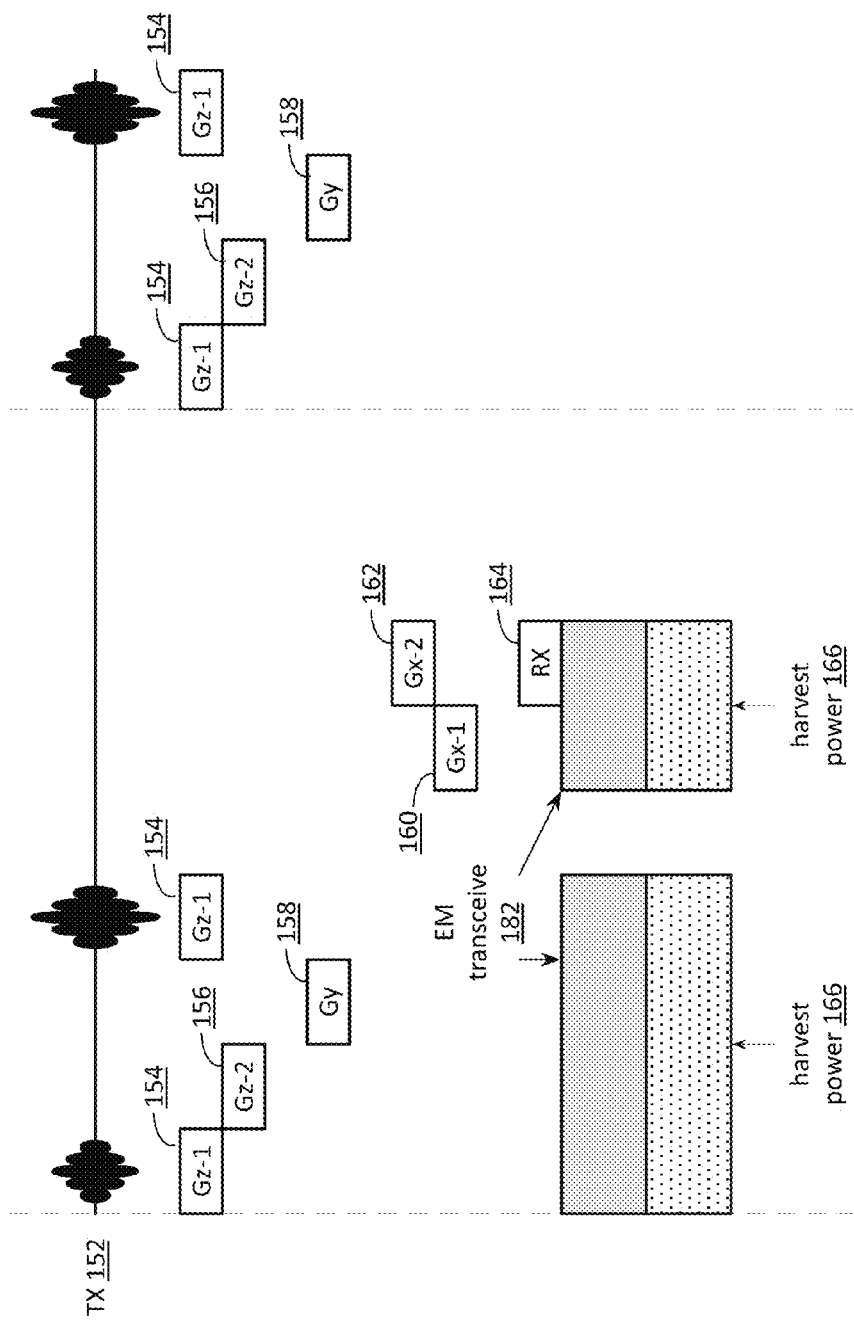
FIG. 20 is a diagram of another example of a communication protocol within a system in accordance with the present invention.

FIG. 20 is a diagram of another example of a communication protocol within the system of FIG. 19. In this diagram, the MRI transmitter 20 transmits RF signals 152, which have a frequency in the range of 3-45 MHz, at various intervals with varying signal strengths. The power harvesting module 46 of the bio-medical units 10 may use these signals to generate power for the bio-medical unit 10.

In addition to the MRI transmitter 20 transmitting its signal, a constant magnetic field and various gradient magnetic fields are created 154-164 (one or more in the x dimension Gx, one or more in the y dimension Gy, and one or more in the z direction Gz). The power harvesting module 46 of the bio-medical unit 10 may further use the constant magnetic field and/or the varying magnetic fields 154-164 to create power for the bio-medical unit 10.

During the transmission periods of the cycle, the bio-medical unit 10 may communicate via the modulated EM signals 182. In this regard, the bio-medical unit 10 generates power and communicates in accordance with the conventional transmission-magnetic field pattern of an MRI machine.

Figure 21:
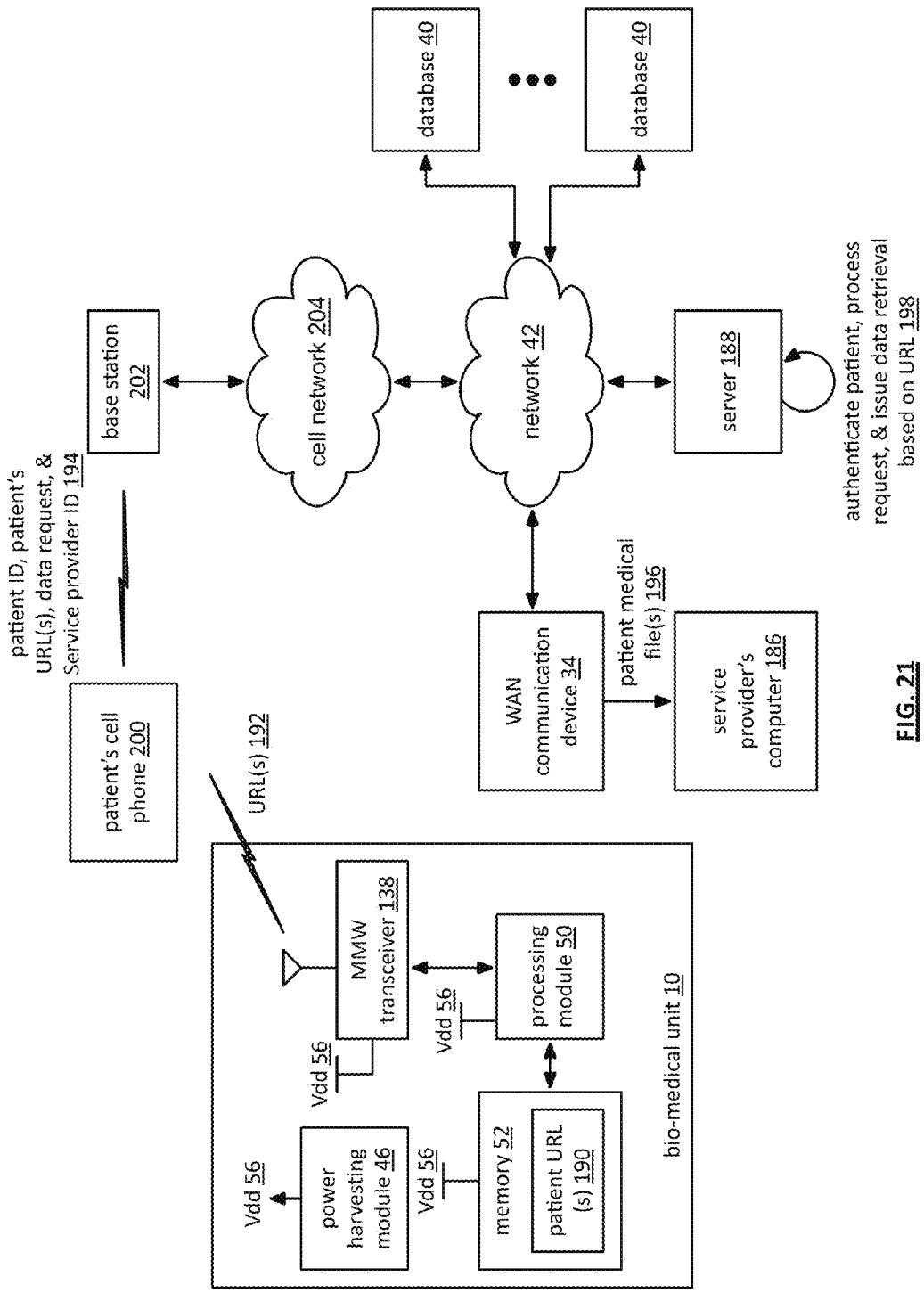
FIG. 21 is a diagram of an embodiment of a bio-medical unit collecting audio and/or ultrasound data in accordance with the present invention.

FIG. 21 is a diagram of another embodiment of a system that includes one or more bio-medical units 10, a service provider's communication device 184, a WAN communication device 34, a service provider's computer 186, a network 42, one or more databases 40, and a server 188. The bio-medical unit 10 includes a power harvesting module 46, a processing module 50, memory 52, and a MMW transceiver 138. The memory is storing URL data for the patient 190. Note that the bio-medical unit 10 may be implanted in the patient, on the patient's body, or on the patient's person (e.g., in a medical tag, a key chain, etc.).

The URL data 192 includes one or more URLs that identify locations of the patient's medical records. For example, one URL may be for the patient's prescription records, another may be for hospitalizations, another for general office visits, etc. In this regard, the bio-medical unit is an index to easily access the patient's medical history.

For a service provider to access the patient's medical records, or a portion thereof, the service provider's communication device 184 retrieves the URL(s) 192 from the bio-medical unit. This may be done as previously discussed. The communication device 184 generates a request to access the patient's information, where the request includes the URL(s) 192, the service provider's ID, and a data request. The request is provided, via the WAN device 34 and the network 42, to the server 188.

The server 188 processes 198 the request. If the service provider is authenticated and the request is valid, the server issues a data retrieval message to the one or more databases identified by the URL(s) 192. The addressed database(s) 40 retrieves the data and provides it via the network 42 and the WAN device 34 to the service provider's computer 184.

Figure 22:
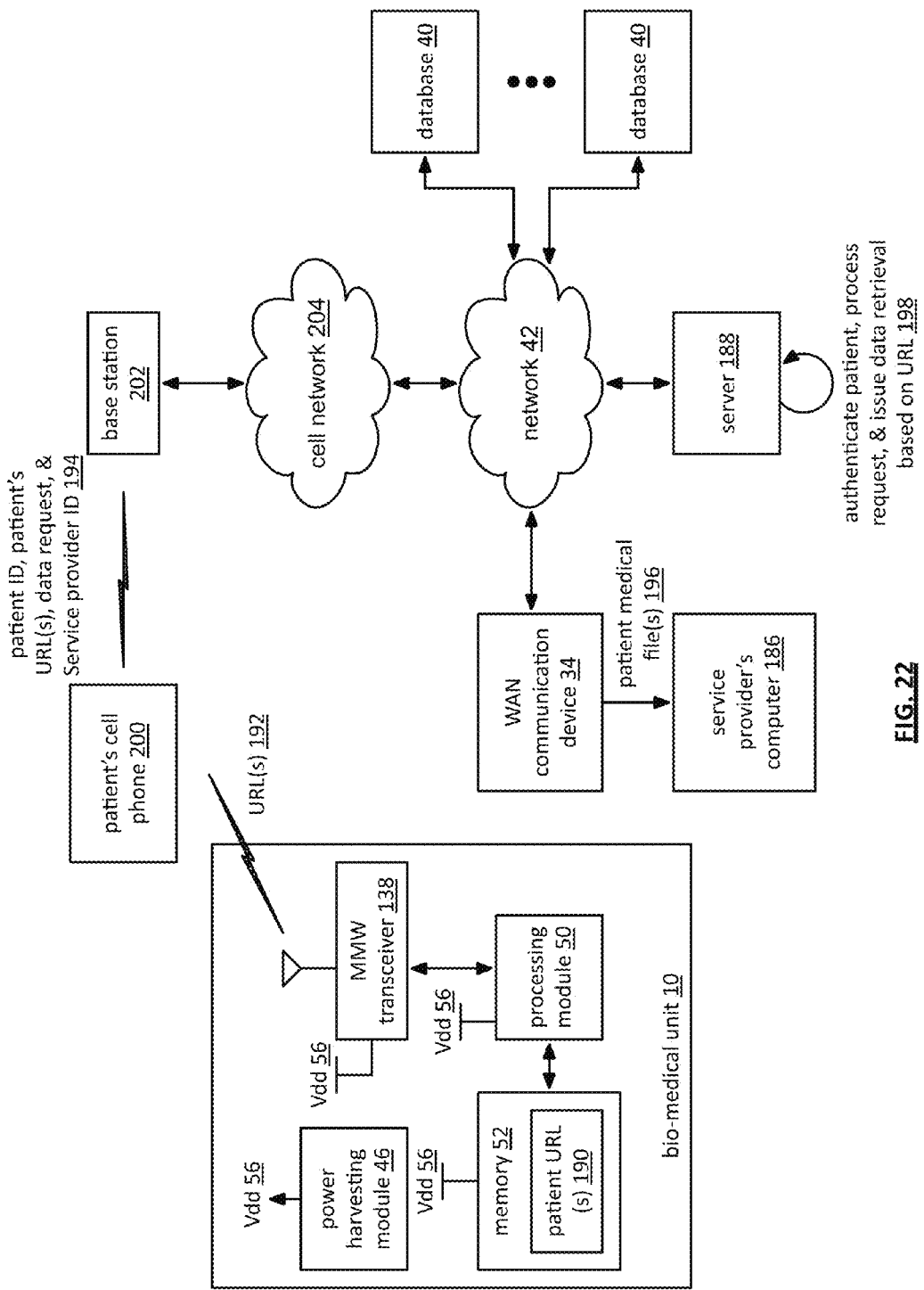
FIG. 22 is a diagram of another embodiment of a system in accordance with the present invention.

FIG. 22 is a diagram of another embodiment of a system that includes one or more bio-medical units 10, the patient's cell phone 200, a WAN communication device 34, a service provider's computer 186, a network 42, one or more databases 40, and a server 188. The bio-medical unit 10 includes a power harvesting module 46, a processing module 50, memory 52, and a MMW transceiver 138. The memory 52 is storing URL data for the patient 190. Note that the bio-medical unit 10 may be implanted in the patient, on the patient's body, or on the patient's person (e.g., in a medical tag, a key chain, etc.).

The URL data 190 includes one or more URLs 192 that identify locations of the patient's medical records. For example, one URL may be for the patient's prescription records, another may be for hospitalizations, another for general office visits, etc. In this regard, the bio-medical unit 10 is an index to easily access the patient's medical history.

For a service provider to access the patient's medical records, or a portion thereof, the patient's cell phone retrieves 200 the URL(s) 192 from the bio-medical unit 10. The cell phone 200 generates a request to access the patient's information, where the request includes the URL(s) 192, the service provider's ID, the patient's ID, and a data request. The request is provided, via the WAN device 34 and the network 42, to the server 188.

The server 188 processes 198 the request. If the service provider is authenticated and the request is valid, the server issues a data retrieval message to the one or more databases 40 identified by the URL(s) 192. The addressed database(s) 40 retrieves the data and provides it via the network 42 and the WAN device 34 to the service provider's computer 186.

Figure 23:
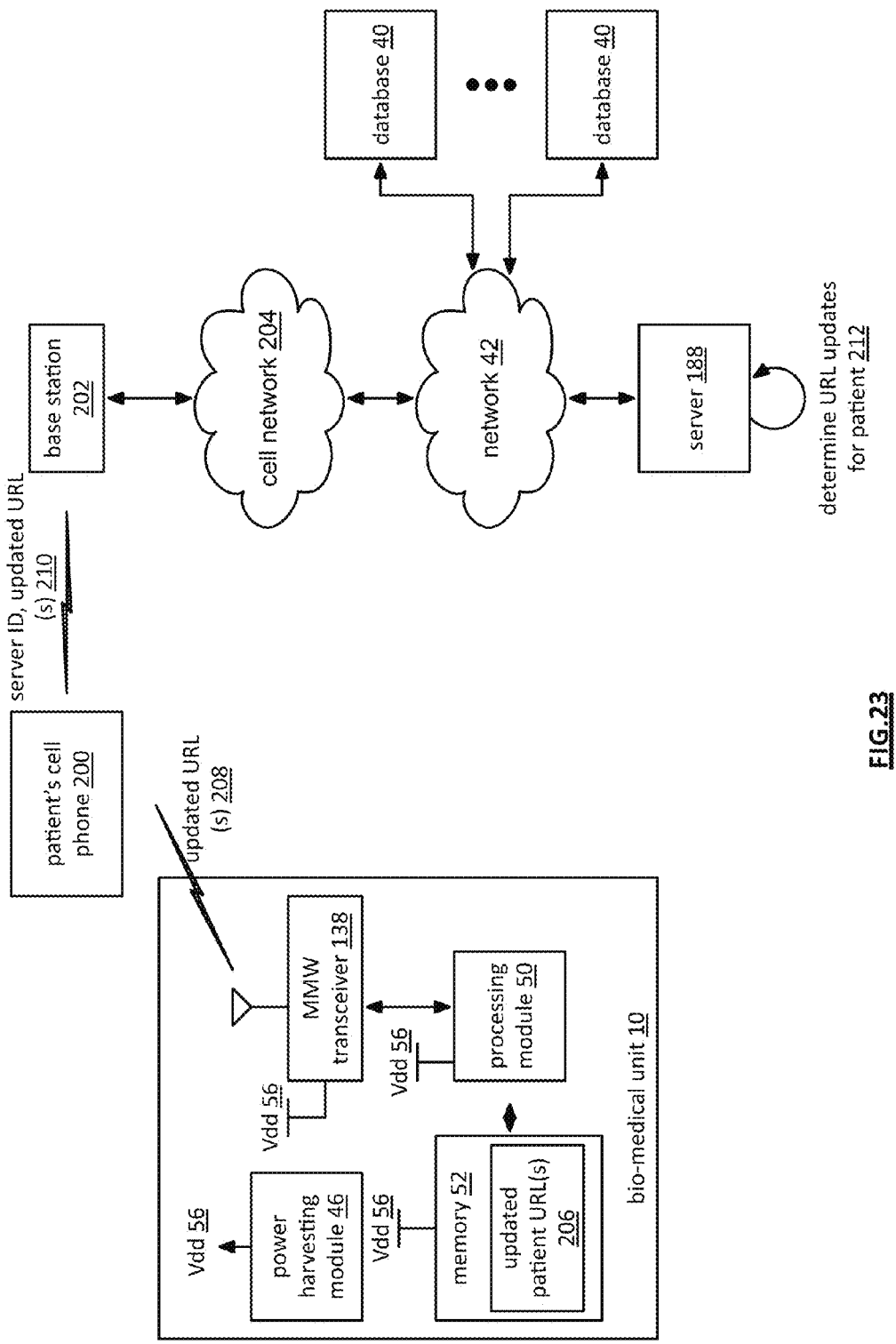
FIG. 23 is a diagram of another embodiment of a system in accordance with the present invention.

FIG. 23 is a diagram of another embodiment of a system that includes one or more bio-medical units 10, the patient's cell phone 200, a WAN communication device 34, a service provider's computer 186, a network 42, one or more databases 40, and a server 188. The bio-medical unit 10 includes a power harvesting module 46, a processing module 50, memory 52, and a MMW transceiver 138. The memory 52 is storing URL data for the patient. Note that the bio-medical unit 10 may be implanted in the patient, on the patient's body, or on the patient's person (e.g., in a medical tag, a key chain, etc.).

The URL data includes one or more URLs that identify locations of the patient's medical records. For example, one URL may be for the patient's prescription records, another may be for hospitalizations, another for general office visits, etc. In this regard, the bio-medical unit is an index to easily access the patient's medical history.

To update the URL(s) in the bio-medical unit 10, the server 188 determines when an update is needed 212. When an update is needed, the server 188 generates an update message that includes the identity of the patient's cell phone 200, the updated URL data 208, and the identity of the bio-medical unit 10. The server 188 provides the update message to the patient's cell phone 200 via the network 42 and a base station 202. The patient's cell phone 200 processes the update message and, when validated, provides the updated URL data 208 to the bio-medical unit 10 for storage in memory 52 as stored updated patient URL(s) 206.

Figure 24:
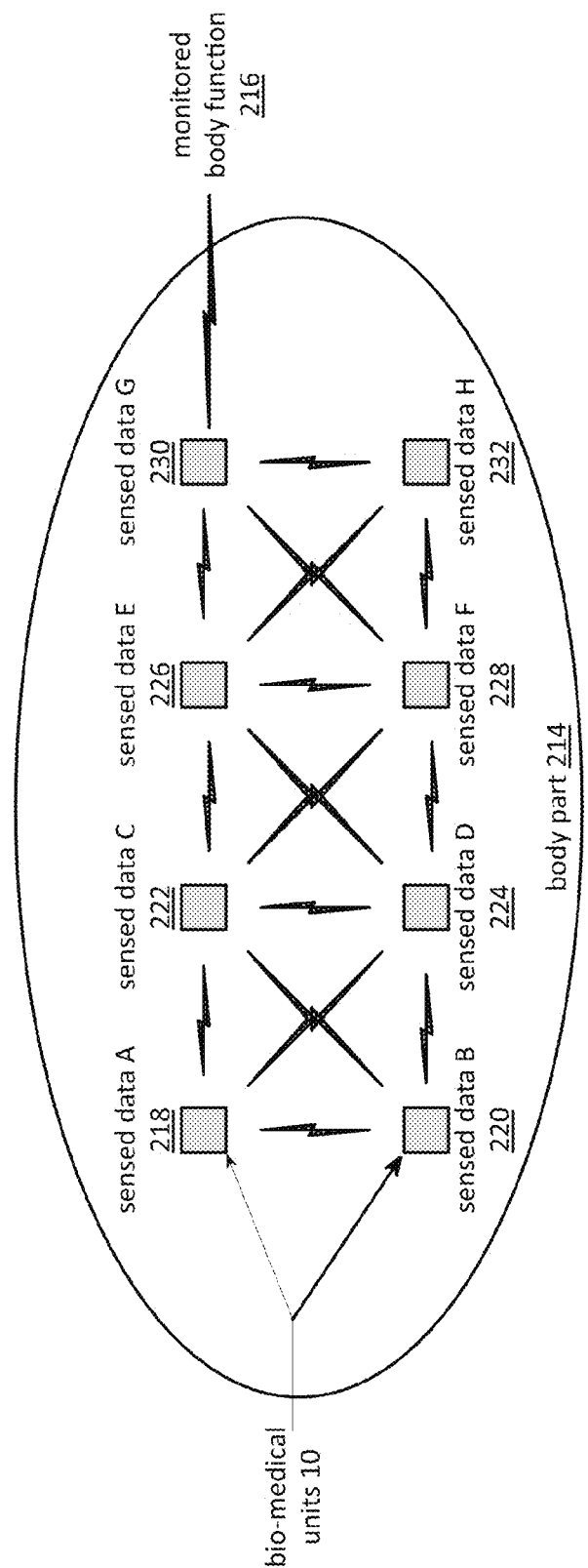
FIG. 24 is a diagram of an embodiment of a network of bio-medical units in accordance with the present invention.

FIG. 24 is a schematic block diagram of an embodiment of networked bio-medical units 10 that communicate with each other, perform sensing functions to produce sensed data 218-232, process the sensed data to produce processed data, and transmit the processed data 216. The bio-medical units 10 may be positioned in a body part to sense data across the body part and to transmit data to an external communication device. The transmitted data may be further processed or aggregated from sensed data.

The bio-medical units 10 may monitor various types of biological functions over a short term or a long term to produce the sensed data 218-232. Note that the sensed data 218-232 may include blood flow rate, blood pressure, temperature, air flow, blood oxygen level, density, white cell count, red cell count, position information, etc.

The bio-medical unit 10 establishes communications with one or more other bio-medical units 10 to facilitate the communication of sensed data 218-232 and processed data 216. The communication may include EM signals, MMW signals, optical signals, sound signals, and/or RF signals.

The bio-medical unit 10 may determine position information based on the sensed data 218-232 and include the position information in the communication. The bio-medical unit 10 may also determine a mode of operation based on one or more of a command, a list, a predetermination, sensed data, and/or processed data. For example, a bio-medical unit 10 at the center of the body part may be in a mode to sense temperature and a bio-medical unit 10 at the outside edge of the body part may sense blood flow.

The bio-medical unit 10 may receive processed data 218-232 from another bio-medical unit and re-send the same processed data 218-232 to yet another bio-medical unit 10. The bio-medical unit 10 may produce processed data based on sensed data 218-232 from the bio-medical unit 10 and/or received processed data from another bio-medical unit 10.

Figure 25:
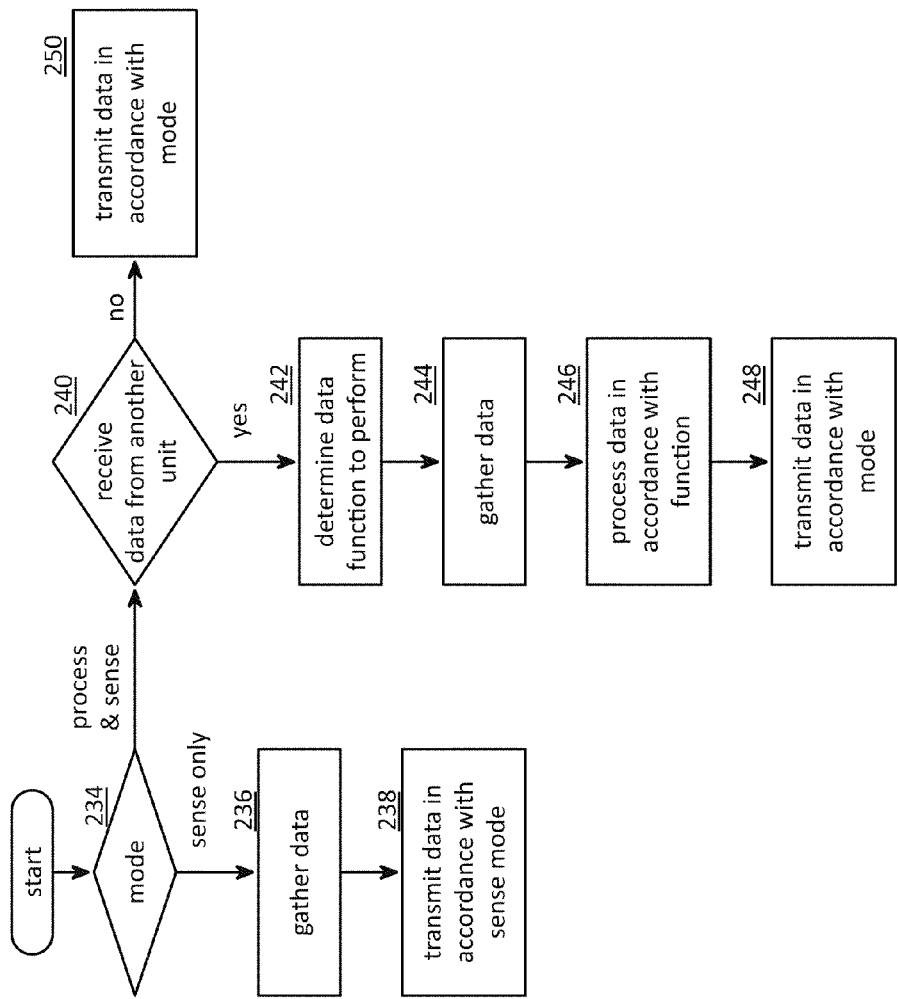
FIG. 25 is a logic diagram of an embodiment of a method for bio-medical unit communications in accordance with the present invention.

FIG. 25 is a flowchart illustrating the processing of networked bio-medical unit data where the bio-medical unit determines the sense mode based on one or more of a predetermination, a stored mode indicator in memory, a command, and/or a dynamic sensed data condition. The method begins at step 234 where the bio-medical unit 10 determines the mode. The method branches to step 240 when the bio-medical unit 10 determines that the mode is process and sense. The method continues to step 236 when the bio-medical unit 10 determines that the mode is sense only.

At step 236, the bio-medical unit 10 gathers data from one or more of the functional modules 54 to produce sensed data. The bio-medical unit 10 may transmit the sensed data 238 to another bio-medical unit 10 and/or an external communication device in accordance with the sense mode. For example, the bio-medical unit 10 may transmit the sensed data at a specific time, to a specific bio-medical unit 10, to a specific external communication device, after a certain time period, when the data is sensed, and/or when the sensed data compares favorably to a threshold (e.g., a temperature trip point).

The method continues at step 240 where the bio-medical unit 10 determines whether it has received data from another unit 10. If not, the method continues to step 250, where the bio-medical unit 10 transmits its sensed data to another bio-medical unit 10 and/or an external communication device in accordance with the sense mode.

When the bio-medical unit 10 has received data from another unit, the method continues at step 242, where the bio-medical unit 10 determines a data function to perform based on one or more of the content of the received data, the sensed data, a command, and/or a predetermination. The data function may one or more of initialization, comparing, compiling, and/or performing a data analysis algorithm.

The method continues at step 244, where the bio-medical unit 10 gathers data from the functional modules 54, and/or the received data from one or more other bio-medical units 10. The method continues at step 246, where the bio-medical unit 10 processes the data in accordance with a function to produce processed data. In addition to the example provided above, the function may also include the functional assignment of the bio-medical unit 10 as determined by a predetermination, a command, sensed data, and/or processed data (e.g., measure blood pressure from the plurality of bio-medical units and summarize the high, low, and average).

The method continues at step 248, where the bio-medical unit 10 transmits the processed data to another bio-medical unit 10 and/or to an external communication device in accordance with the sense mode. For example, the bio-medical unit 10 may transmit the sensed data at a specific time, to a specific bio-medical unit 10, to a specific external communication device, after a certain time period, when the data is sensed, and/or when the sensed data compares favorably to a threshold (e.g., a temperature trip point). Note that the communication protocol may be the same or different between bio-medical units 10 and/or between the bio-medical unit 10 and the external communication device.

Figure 26:
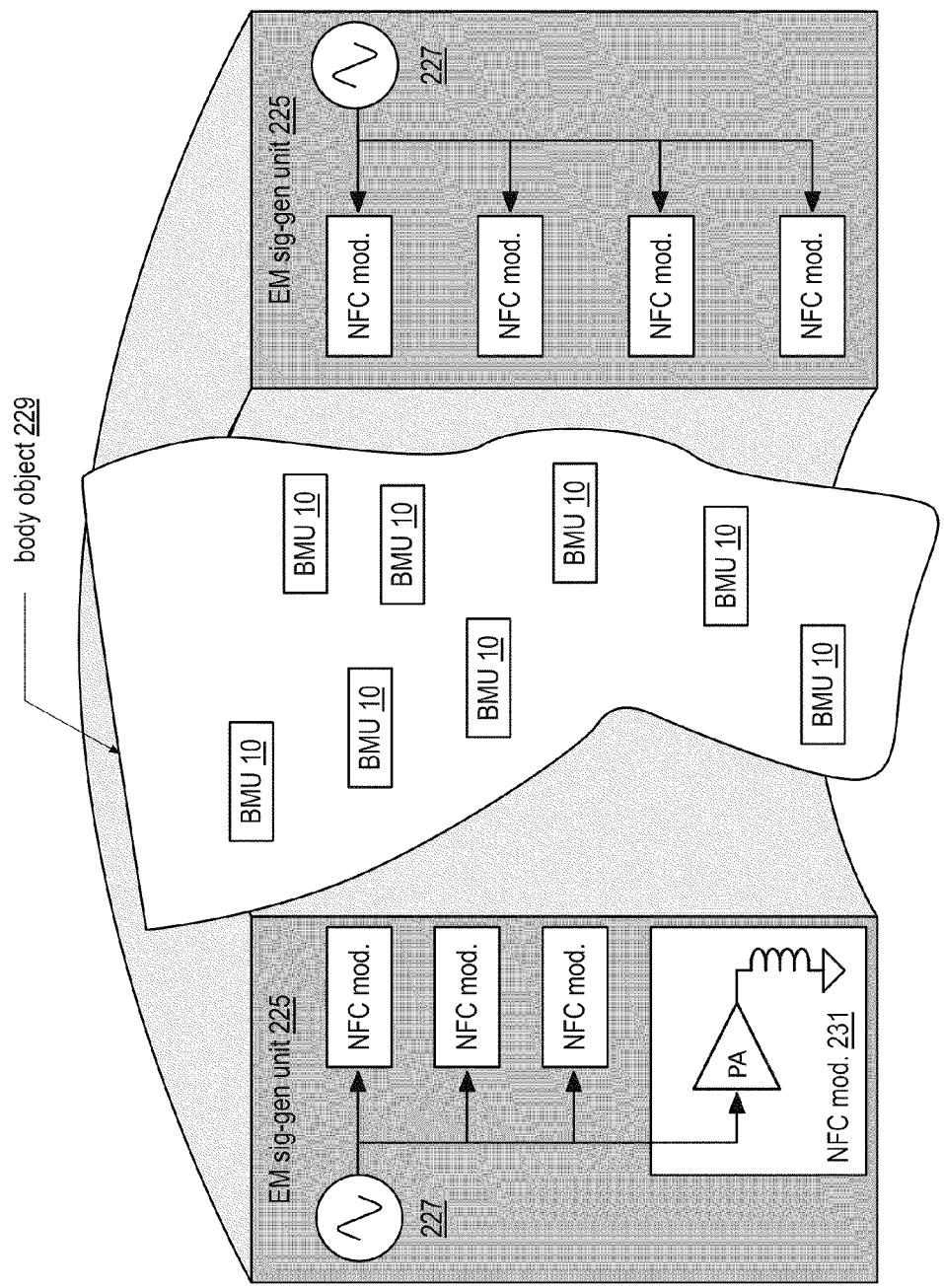
FIG. 26 is a diagram of an embodiment of a system including bio-medical units for physical therapy treatment in accordance with the present invention.

FIG. 26 is a diagram of an embodiment of a physical therapy (PT) system that includes bio-medical units (BMU) 10 and an electromagnetic (EM) signal generating unit 225. Each of the bio-medical units 10 includes a power harvesting module, a wireless communication module, a processing module, and a functional module as shown in one or more preceding and/or subsequent figures. The EM signal generating unit 225 includes at least one signal generating module 227 and a plurality of near field communication (NFC) modules 231. An NFC module 231 may include a power amplifier (PA) and at least one coil.

The EM signal generating unit 225 encircles, partially encircles, overlays, and/or is otherwise proximally located to a body object 229 (e.g., knee, elbow, foot, ankle, calf, thigh, core, shoulder, etc.). For instance, the EM signal generating unit 225 may include a wearable housing that fits over the body object (e.g., a sleeve, a knee brace, an adjustable cuff, etc.) or may be a separate piece of equipment that the body object is place in or near to. In addition to supporting the components of the electromagnetic signal generating unit 225, the wearable housing and/or other piece of equipment may support one or more bio-medical units 10 further facilitate physical therapy of the body object 229.

In an example of operation, when the EM signal generating unit 225 is enabled, it provides an electromagnetic (EM) signal to the bio-medical units (BMU) 10, which are associated with the body part (e.g., on the skin, implanted under the skin, implanted in a muscle, embedded in an artificial body part, embedded in sutures, in the wearable housing, etc.). In particular, the signal generating module 227 (e.g., a phase locked loop, a crystal oscillator, a clock circuit, a digital frequency synthesizer, etc.) generates one or more signals (e.g., oscillation, clock signal, etc.). As an example, the signal generating module 227 generates a sinusoidal signal having a selected frequency and amplitude. As another example, the signal generating module 227 generates a sinusoidal signal having a varying frequency and/or varying amplitude. As yet another example, the signal generating module 227 generates sinusoidal signal that is gated on and off.

One or of more of the NFC modules receives the signal and converts it into a component of the electromagnetic (EM) signal. For instance, several NFC modules convert the signal into EM signal components having different gating on/off times, different frequencies, different amplitudes, etc., such that, in air, the EM signal components combine to form a varying EM signal.

The power harvesting module of a BMU 10 generates a supply voltage from the electromagnetic signal as previously discussed. The supply voltage is used to power the wireless communication module, the processing module, and the functional module. When powered, the wireless communication module converts a received wireless communication into a physical therapy command. The wireless communication may be received from a wireless communication device (e.g., a cell phone, a computer, the EM signal generating unit 225, etc.), which is controlling the physical therapy on the body part.

The processing module interprets the physical therapy command to determine a physical therapy function. For example, the physical therapy function may be an electronic stimulation function, a monitoring function, and/or an electromyography function. The electric stimulation may be used to promote healing, reduce pain, promote blood flow, reduce swelling, etc., which may be administered by a BMU of FIGS. 45, 46, and/or 55. The monitoring function may include one or more of monitoring correct form of a physical therapy movement, monitoring program compliance (e.g., track sets, reps of movements, daily performance of movements, duration of PT session, duration of each movement, etc.), monitoring effort level (e.g., monitor muscle contraction, monitor muscle expansion, heart rate, blood-oxygen level, monitor electrical patterns of muscle neurotransmitters, etc.), and monitoring pain level (e.g., monitor electrical patterns of pain neurotransmitters, etc.).

The functional module of the bio-medical unit 10 performs the physical therapy function. When the physical therapy function is a monitoring function, the functional module generates physical therapy data in response to performing the physical therapy function. For example, if the physical therapy function is to monitor a physical therapy movement, the functional module senses movement (e.g., with respect to a fixed reference point) of the body object such that the actual movement can be compared to a desired movement. If the actual movement is not as desired, feedback and/or corrective measures can be provided to the physical therapy patient. For example, a message may be sent to the patient's cell phone indicating the improver form and a method for correcting it. As another example, an electrical stimulus may be activated within the BMU to provide feedback regarding improper movement, to enhance movement, to reduce pain, etc.

When physical therapy data is generated, the processing module generates a physical therapy response based on physical therapy data. The communication module converts the physical therapy response into a transmit wireless communication that is transmitted to the wireless communication device and/or to the EM signal generating unit 225.

Figure 27:
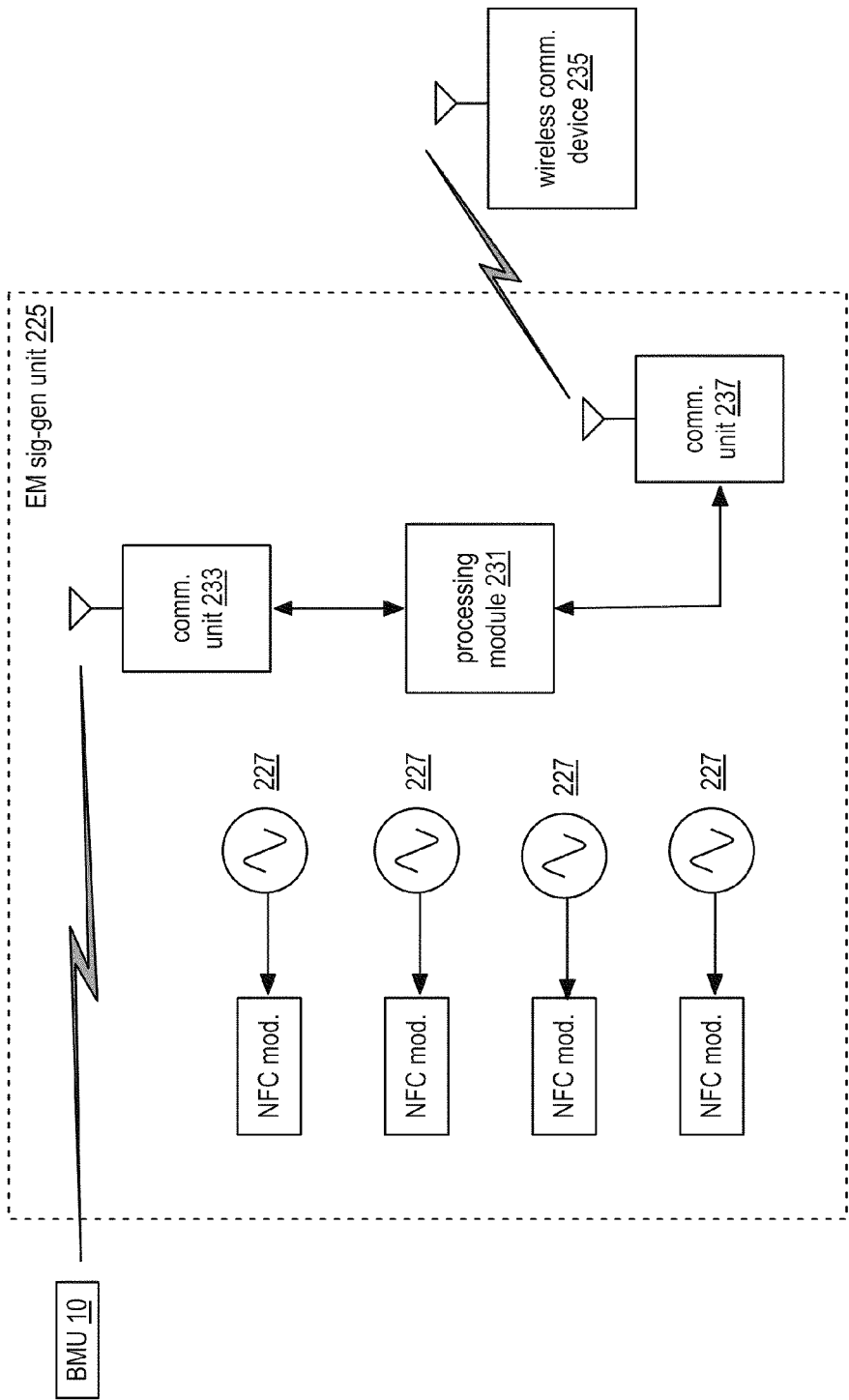
FIG. 27 is a diagram of an embodiment of an electromagnetic signal generating unit in accordance with the present invention.

FIG. 27 is a diagram of an embodiment of an electromagnetic (EM) signal generating unit 225 that includes at least one signal generating unit 227, at least one near field communication (NFC) module, a processing module 231, and at least one communication module 233. In an example, the EM signal generating unit 225 includes a plurality of signal generating units 227, a corresponding number of NFC modules, and two communication units 233 and 237: where one communication unit 233 communicates with bio-medical units (BMU) 10 and the other communication unit 237 communicates with a wireless communication device 235 (e.g., a cell phone, a computer, medical equipment, etc.).

In an example of operation, the processing module 231 enables the signal generating units 227 in a pattern such that each pairing of a signal generating unit and an NFC module generates a component of a varying electromagnetic field. For instance, each pairing may be enabled at a different frequency, at a different power level, for a different duration, etc., at the same frequency, at the same power level, for the same duration, etc. and/or a combination thereof. In this manner, the processing module 231 can enable various electromagnetic signals to power the BMUs 10.

In addition, the processing module executes a physical therapy program to produce one or more physical therapy commands. The physical therapy program may be stored within memory of the EM signal generating unit 225 or the processing module may receive, via the communication unit 237, the physical therapy program from the wireless communication device 235. In either case, the physical therapy program contains a set of instructions to monitor a body object's movements, efforts, and/or pain levels through a series of physical therapy exercises and/or treatments; to track compliance with performance of the physical therapy exercises and/or treatments; to provide electric stimulation to facilitate the physical therapy treatments; and/or to facilitate an electromyography.

For each physical therapy (PT) function to be performed by one or more bio-medical units (BMU) 10, the processing module 231 transmits, via the communication unit 231 or at least one of the NFC modules, the PT function to the BMU(s) 10. One or more of the BMUs 10 provides a PT response via the communication unit 231 or at least one of the NFC modules, which is, in turn, received by the processing module. The processing module 231 gathers the responses from the BMUs and processes them to produce PT data (e.g., program compliance data, monitoring data, effort level data, pain level data, etc.).

Figure 28:
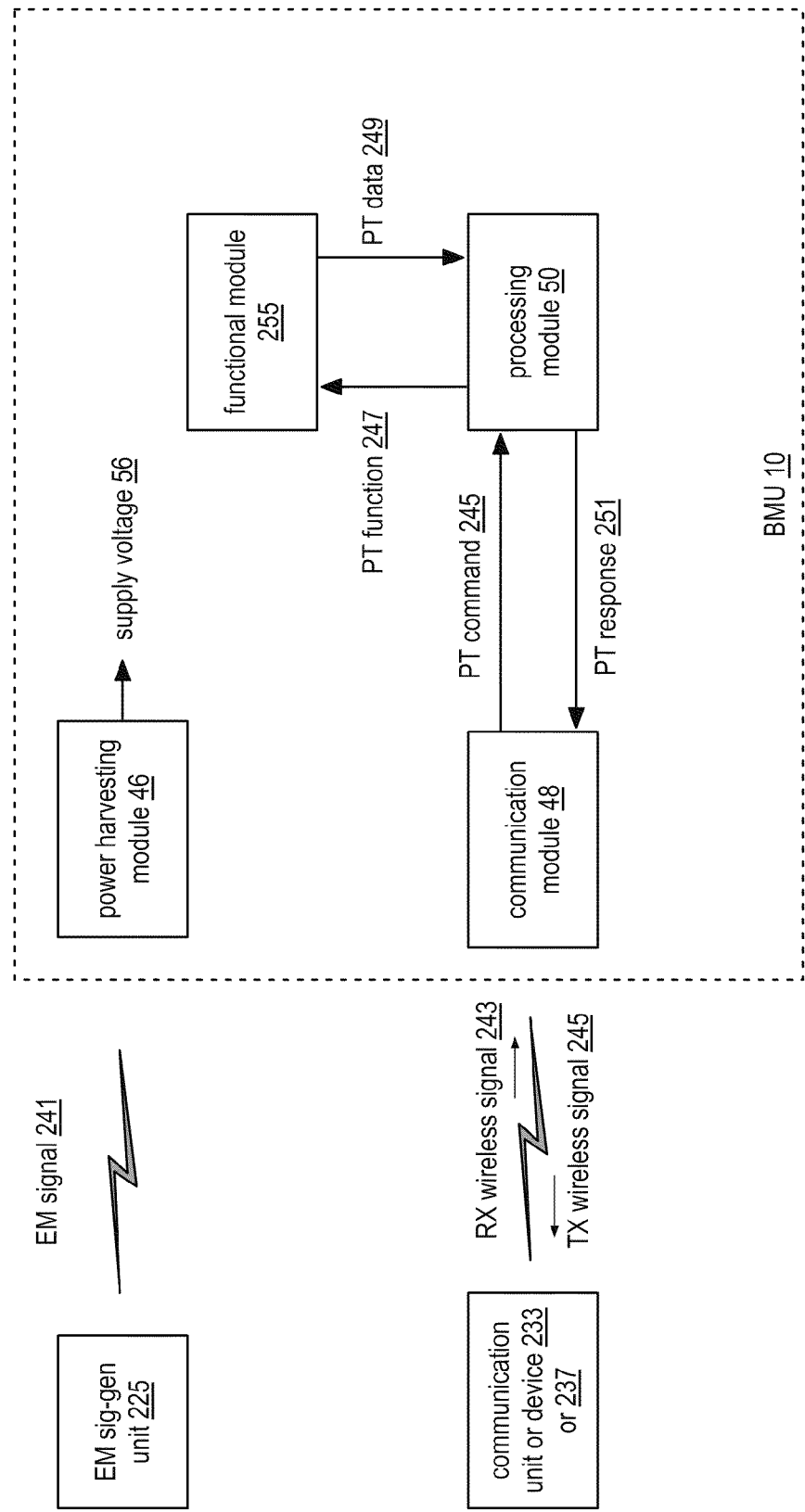
FIG. 28 is a diagram of another embodiment of a bio-medical unit in accordance with the present invention.

FIG. 28 is a diagram of another embodiment of a bio-medical unit (BMU) 10 that includes a power harvesting module 46, a communication module 48, a processing module 50, and a functional module 255. The power harvesting module 46 generates a supply voltage 56 from an electromagnetic signal 241 it receives from the EM signal generating unit 225. The supply voltage 56 powers the other modules of the BMU 10.

In an example of operation, the wireless communication module 48 converts a received wireless communication 243 into a physical therapy command 245. The processing module 50 interprets the physical therapy command 245 to determine a physical therapy function 247. The functional module 255 (e.g., any one of modules 98-114 of FIGS. 16, 45, 46) performs the physical therapy function and to generate physical therapy data 249 when the physical therapy function is a monitoring function.

The processing module 50 generates a physical therapy response 251 based on physical therapy data 249. The wireless communication module 48 converts the physical therapy response 251 into a transmit wireless communication 245, which is transmitted to a communication unit 233 of the EM signal generating unit 225 and/or to the wireless communication device 237.

Figure 29:
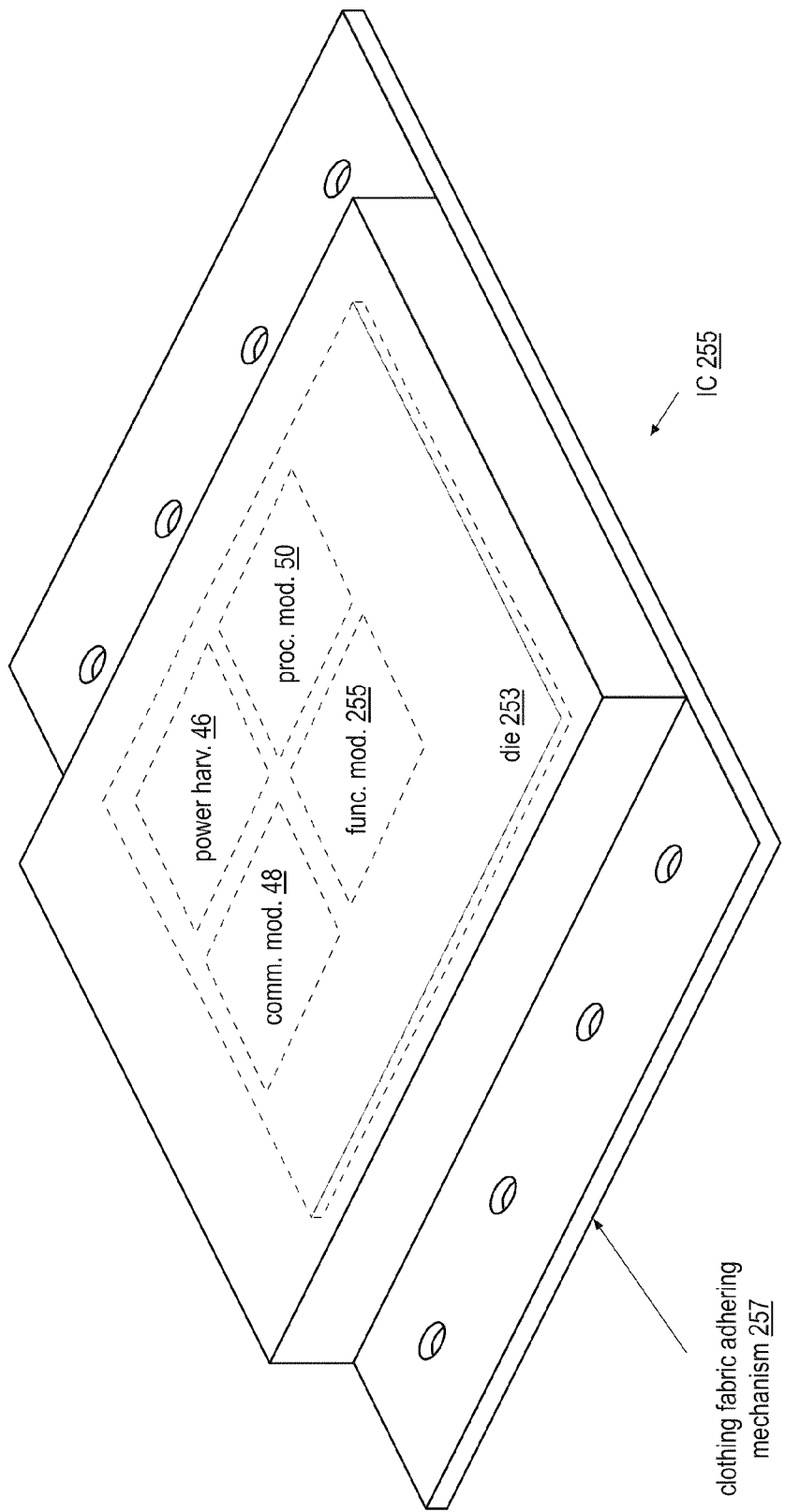
FIG. 29 is a diagram of an embodiment of an integrated circuit (IC) that includes a bio-medical unit in accordance with the present invention.

FIG. 29 is a diagram of an embodiment of an integrated circuit (IC) 255 that includes a die 253 and an IC package housing. The die 253 supports a bio-medical unit 10 that includes a power harvesting module 46, a communication module 48, a processing module 50, and at least one functional module 255. The IC package houses the die 253 and includes a clothing fabric adhering mechanism 257, which allows the IC 255 to be adhered to a clothing fabric. Note that the IC 255 may further include an encapsulant for encapsulating the IC package such that the IC is essentially hermetically sealed. Further note that the size of the IC 255 may be less than 1 millimeter by 1 millimeter.

The fabric adhering mechanism 257 may be implemented in a variety of ways. For example, the fabric adhering mechanism 257 may include one or more eyelets for facilitating sewing the IC into clothing fabric. As another example, the fabric adhering mechanism 257 may include one or more hooks for facilitating sewing the IC into clothing fabric. As yet another example, the fabric adhering mechanism 257 may include one or more notches for facilitating sewing the IC into clothing fabric. As a further example, the fabric adhering mechanism 257 may include a fabric adhesive for facilitating gluing the IC into clothing fabric.

Figure 30:
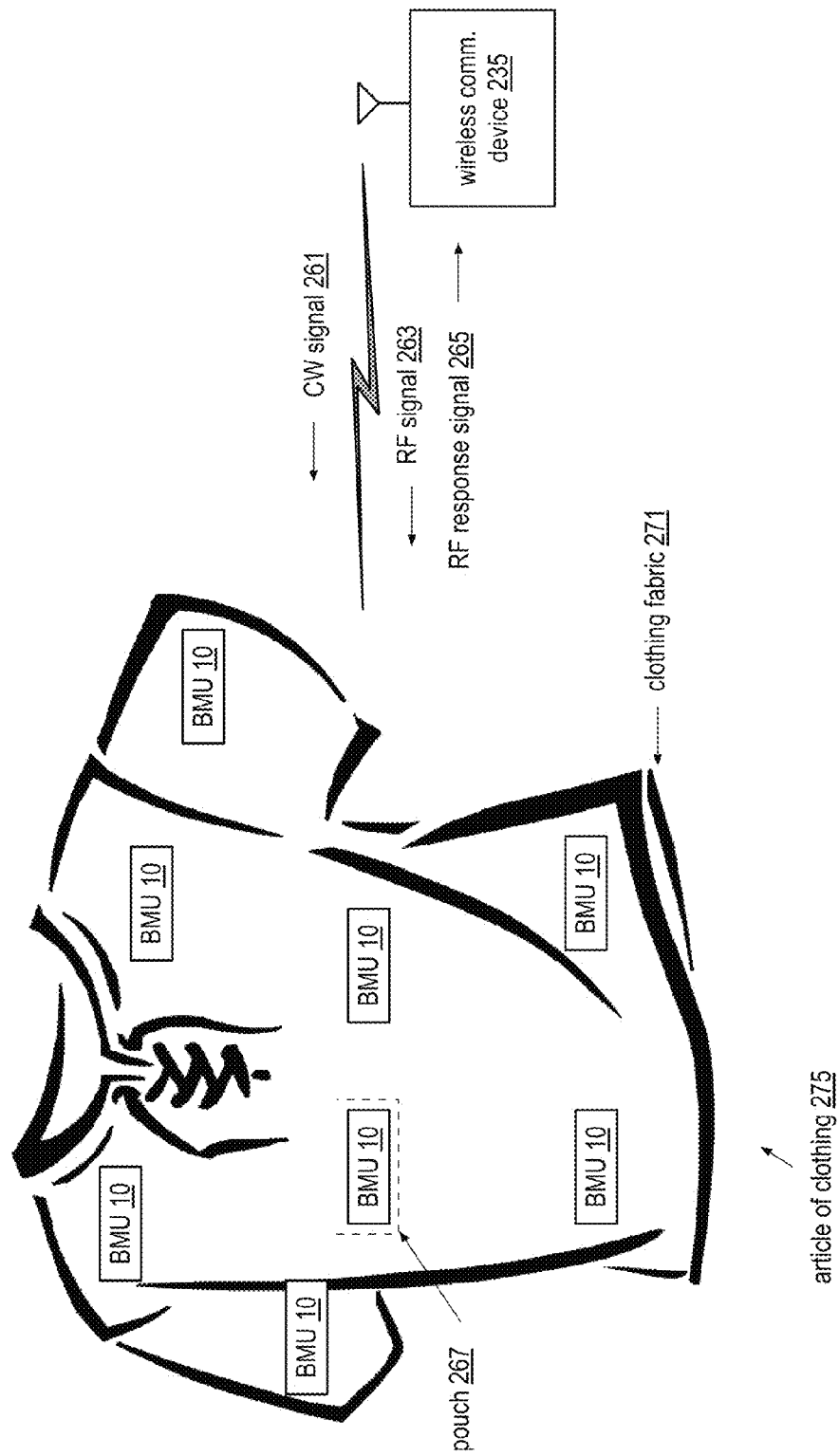
FIG. 30 is a diagram of an embodiment of an article of clothing that includes a plurality of bio-medical units in accordance with the present invention.

FIG. 30 is a diagram of an embodiment of an article of clothing 275 that includes a clothing fabric 271 (e.g., cotton, dry-fit material, polyester, etc.) and a plurality of bio-medical units (BMU) 275 integrated therein (e.g., in the seams of the article of clothing and/or in small pouches 267 of the article of clothing). Each of the BMUs 10 includes a power harvesting module 46, a communication module 48, a processing module 50, and at least one functional module 255. The BMUs 10 communicate with a wireless communication 235 via their respective communication units 28.

In an example of operation, a power harvesting module 46 of a BMU 10 converts at least one of body heat, body motion, an electromagnetic signal, light, and radio frequency (RF) signals into a supply voltage that powers the other modules of the BMU 10. The power harvesting module 46 may be implemented in a variety of ways, including combinations thereof.

For example, the power harvesting module 46 includes an electromagnetic signal to voltage conversion module, which may include an array of inductors and/or an array of Hall-effect devices as previously discussed with reference to one or more of FIGS. 11-15. As another example, the power harvesting module 46 includes an RF signal to voltage conversion module for converting a continuous wave (CW) signal 261 and/or an RF signal 263 into the supply voltage. As yet another example, the power harvesting module 46 includes a motion to voltage conversion module (e.g., piezoelectric devices as shown in one or more of FIGS. 11-15). As a further example, the power harvesting module 46 includes a light to voltage conversion module. As a still further example, the power harvesting module 46 includes a heat to voltage conversion module.

When powered, the communication module 48 is operable to convert an inbound wireless signal 263 into an inbound symbol stream. The processing module 50 converts the inbound symbol stream into a bio-medical function, which may be an image capture function, a movement capture function, a sound capture function, a topical treatment function, and/or an electronic stimulation function. The functional module 255 performs the bio-medical function and, when the bio-medical function is a monitoring function, generates a bio-medical response.

The processing module converts the bio-medical response into the outbound symbol stream. The communication module 48 converts the outbound symbol stream into an outbound wireless signal 265 that is transmitted to the wireless communication device 235.

Figures 31A, 31B:
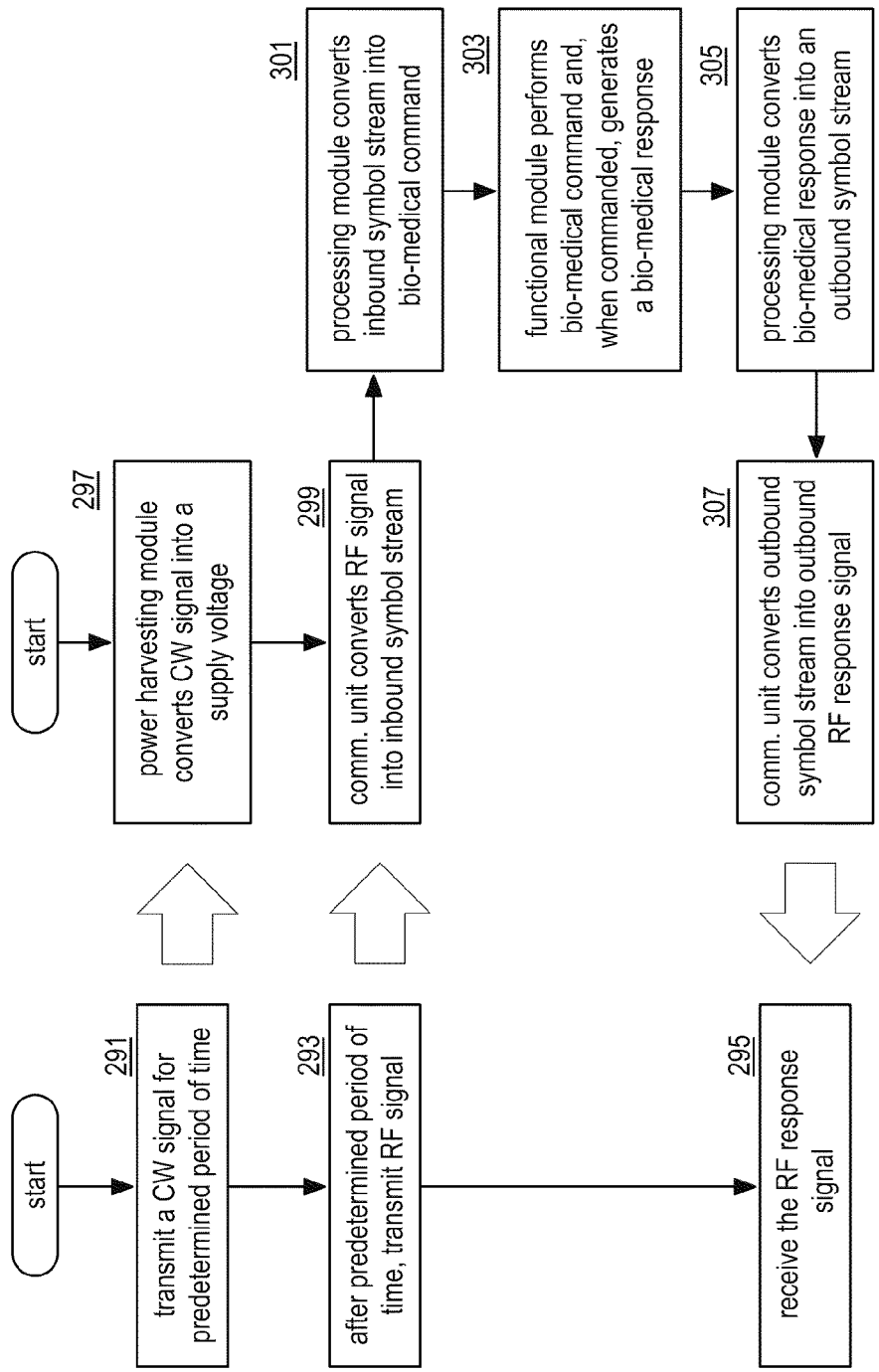
FIGS. 31a and 31b are logic diagrams of an embodiment of a method for communication with an article of clothing that includes a plurality of bio-medical units in accordance with the present invention.

FIGS. 31a and 31b are logic diagrams of an embodiment of a method for communication with an article of clothing that includes a plurality of bio-medical units. The method of FIG. 31a may be executed by a wireless communication device that includes a processing module and memory that stores the bio-medical application in a computer readable format and the method of FIG. 31b may be executed by one or more bio-medical units integrated into clothing fabric.

The method begins at step 291 where the wireless communication device transmits a continuous wave (CW) signal for predetermined period of time (e.g., a few milliseconds to 10s of seconds). At step 297, the power harvesting module of a bio-medical unit converts the CW signal into a supply voltage, which powers the other modules of the BMU.

The method continues at step 293 where, after expiration of the predetermined period of time, the wireless communication device transmits a radio frequency (RF) signal, which includes one or more bio-medical commands for one or more BMUs. The RF signal may further include a command to convert the RF signal into the supply voltage. At step 299, the communication unit of the bio-medical unit converts the RF signal into an inbound symbol stream. At step 301, a processing module of the bio-medical unit converts the inbound symbol stream into a bio-medical command. At step 303, a functional module of the bio-medical unit performs the bio-medical command and, when commanded, generates a bio-medical response. At step 305, the processing module converts the bio-medical response into an outbound symbol stream. At step 307, the communication unit converts the outbound symbol stream into an outbound RF response signal.

The method continues at step 295, where the wireless communication device receives the RF response signal. In one instance, the RF response signal includes a request for re-transmission of the CW signal (e.g., the BMU did not have sufficient power to complete the bio-medical function).

The wireless communication device may also further function to, after sending the RF signal, resume transmitting the CW signal. The wireless communication device then indicates a time window for when the bio-medical is to transmit the RF response signal. The wireless communication device stops transmitting the CW signal during the time window.

Figure 32:
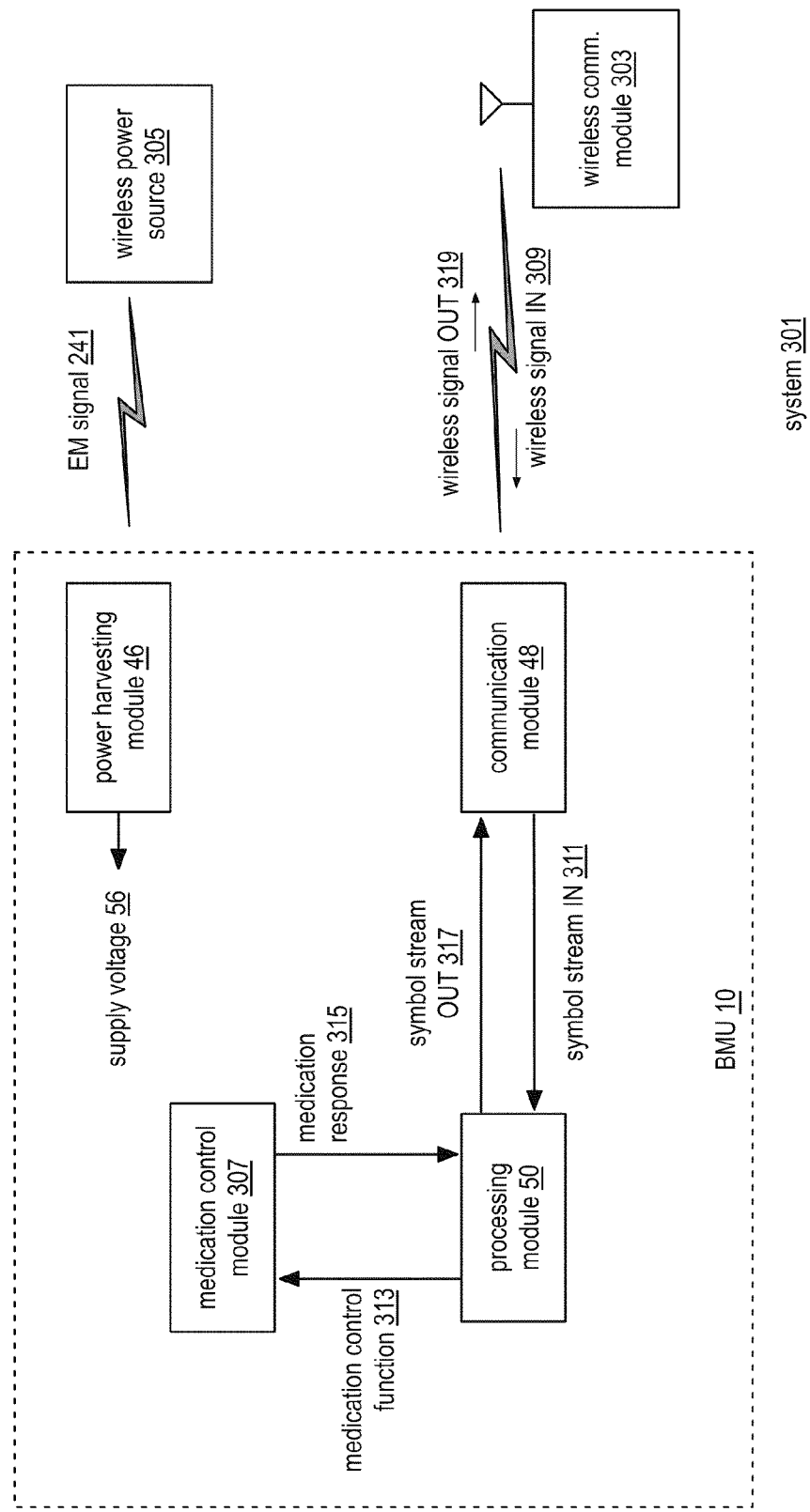
FIG. 32 is a diagram of an embodiment of a system including bio-medical units for medication control in accordance with the present invention.

FIG. 32 is a diagram of an embodiment of a system 301 for medication control that includes bio-medical units (BMU) 10, a wireless power source 305, and a wireless communication module 303. Each of the BMUs 10 includes a power harvesting module 46, a communication module 48, a processing module 50, and at least one medication control module 307. Note that a wireless communication device (e.g., 235) may include the wireless communication module and the wireless power source.

In an example of operation, the wireless power source 305 (e.g., an MRI unit, a portable MRI unit, an EM signal generating unit 225, or another device that generates a varying EM signal) generates an electromagnetic signal 241. The power harvesting module of a BMU converts the electromagnetic signal into a supply voltage, which powers the other modules of the BMU.

With the BMU 10 powered, the wireless communication module transmits an inbound wireless signal to the bio-medical unit, where the inbound wireless signal 309 has, embedded therein, a medication control function. The communication module 48 of the BMU converts the inbound wireless signal 309 into an inbound symbol stream 311. The processing module 50 converts the inbound symbol stream 311 into a medication control function 313 (e.g., sample a body component for presence and/or concentration of a medication, administer a medication, etc.).

The medication control module 307 (e.g., as shown in one or more of FIGS. 59-62) performs the medication control function 313 and generates a medication response 315 as a result of performing the medication control function. The processing module 50 converts the medication response 315 into the outbound symbol stream 317. The communication module 48 converts the outbound symbol stream 317 into an outbound wireless signal 319, which is transmitted to the wireless communication module 303.

In a more specific example, the medication control function includes an instruction to sample a body component (e.g., blood, blood component, bodily fluid, air intake, exhale, human waste, etc.) for the presence (e.g., to determine if the person is taking the drug) and/or concentration of a medication (e.g., to determine how much of the drug is being taken). In this example, the medication control module includes a probe mechanism, a testing module, and a cleaning mechanism. The probe mechanism (e.g., needle and pipette of FIG. 62) samples the body component. The testing module (e.g., MEMS sample analyzer of FIG. 62) tests the body component for the presence and/or concentration of the medication to produce the medication response. The cleaning mechanism (e.g., wave based MEMS cleaner of FIG. 62) cleans the probe mechanism and the testing module after testing the body component.

The wireless communication module 303 receives the medication response regarding the testing of the body component and interprets it to determine whether the medication is under-utilized, over-utilized, or appropriately utilized. When the medication is over-utilized, the wireless communication module determines an over-utilized response based on level of over-utilization. For example, if the medication is slightly over-used, the response may be to send a text message to the patient and/or the patient's doctor. As another example, if the medication was used to an overdose level, then the response may be to contact emergency medical services.

When the medication is under-utilized, the wireless communication module determines an under-utilized response based on level of under-utilization. For example, if the medication is slightly under-used, the response may be to send a text message to the patient and/or the patient's doctor. As another example, if the medication is not being used, the response may to test the patient's vital signs (e.g., if at undesired levels, contact emergency medical services), to send a text message to the patient and/or the patient's doctor, or other response.

In another more specific example, the medication control function includes an instruction to administer a medication. In this example, the medication control module includes a medication canister and a MEMS controlled release module as shown in one or more of FIGS. 59-61. The medication canister contains the medication and the micro electromechanical system (MEMS) controlled release module releases the medication in a controlled manner.

In another example of the operation, the bio-medical units 10 include BMUs for a specific task regarding medication control. For example, a first bio-medical unit monitors the presence and/or the concentration of a first medication in a body component; a second bio-medical unit monitors the presence and/or the concentration of a second medication in a body component (e.g., the same or different as checked for the first medication); a third bio-medical unit monitor a first type of bodily reaction to medication (e.g., change in body temperature, change in white and/or red blood cell count, etc.); and a fourth bio-medical unit monitors a second type of bodily reaction to medication. In this manner, when a patient is taking multiple medications, the bodies reactions can be monitored as well as when, how often, and how much of the medications the patient is taking.

Continuing with this example, the wireless communication module receives the medication response to include data regarding the at least one of presence and concentration of the first medication, data regarding the at least one of presence and concentration of the second medication, data regarding the first type of bodily reaction to medication, and data regarding the second type of bodily reaction to medication. The wireless communication module 303 interprets the medication response to determine whether an undesired medication reaction is occurring. When the undesired medication reaction is occurring, the wireless communication module determines a medication alert response (e.g., notify patient, notify patient's doctor, record in patient's records, contact emergency medical services, etc.) regarding the undesired medication reaction based on level of the undesired medication reaction.

FIGS. 33*a* and 33*b* are logic diagrams of an embodiment of a method for controlling and/or monitoring medication administration. The method of FIG. 33*a* may be executed by a wireless communication device that includes a processing module and memory that stores the bio-medical application in a computer readable format and the method of FIG. 33B may be executed by one or more bio-medical units integrated into clothing fabric. Note that the wireless communication device may generate an electromagnetic signal that wirelessly powers one or more of the bio-medical units.

The method begins at step 331 where the wireless communication device generates a medication control function. The method continues at step 333 where the wireless communication device converts the medication control function into a wireless control signal. The method continues at step 335 where the wireless communication device transmits the wireless control signal to one or more bio-medical units.

At step 341, the bio-medical unit recaptures the medication control function from the wireless control signal. At step 343, the bio-medical unit performs the medication control function. At step 345, the bio-medical unit generates the medication response in response to performing the medication control function. At step 347, the bio-medical unit converts the medication response into a wireless response signal.

The method continues at step 337 where the wireless communication device receives the wireless response signal. The method continues at step 339 where the wireless communication device recaptures the medication response from the wireless response signal.

As a specific example, when the medication control function includes an instruction to sample a body component for the presence and/or concentration of a medication, the wireless communication device recaptures, as the medication response, the presence and/or the concentration of the medication in a body component. The wireless communication device then interprets the medication response to determine whether the medication is under-utilized, over-utilized, or appropriately utilized. When the medication is over-utilized, the wireless communication device determines an over-utilized response based on level of over-utilization. When the medication is under-utilized, the wireless communication device determines an under-utilized response based on level of under-utilization.

As another specific example, the wireless communication device receives a plurality of wireless response signals and recaptures a plurality of medication responses from the wireless response signals. In particular, a first medication response corresponds to the presence and/or the concentration of a first medication in the body component; a second medication response corresponds to the presence and/or the concentration of a second medication in the body component; a third medication response corresponds to a first type of bodily reaction to medication; and a fourth medication response corresponds to a second type of bodily reaction to medication. The wireless communication device then interprets the medication responses to determine whether an undesired medication reaction is occurring. When the undesired medication reaction is occurring, the wireless communication device determines a medication alert response regarding the undesired medication reaction based on level of the undesired medication reaction.

Figure 34:
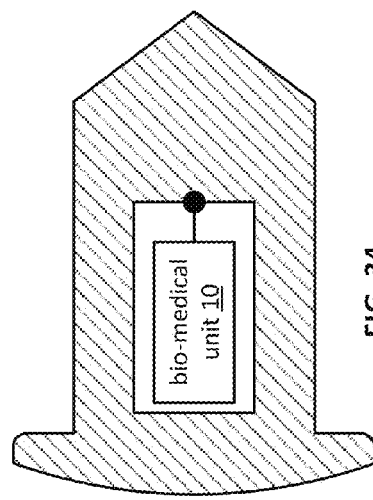
FIG. 34 is a diagram of an embodiment of a surgical fastener including a bio-medical unit in accordance with the present invention.

FIG. 34 is a mechanical diagram of an embodiment of an embedded bio-medical unit 10 in an artificial body part (e.g., a metal screw or plate), which includes a cavity as the bio-medical mounting mechanism. As shown, the bio-medical unit 10 is mounted within, or at least partially within, the cavity and the structure of the artificial body part provides the antenna and/or coil for the bio-medical unit 10. Note that a plurality of embedded bio-medical units 10 may be utilized for diagnostics and/or treatment of health issues. For example, the plurality of bio-medical units 10 may be embedded in a plurality of metal screws that are inserted in a bone to repair a break. The bio-medical units 10 may monitor the position of the bone to detect any undesired stress, cracks, breaks, and/or any other potential issues.

Figure 35:
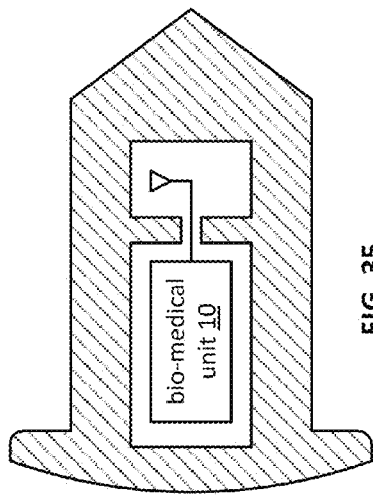
FIG. 35 is a diagram of another embodiment of a surgical fastener including a bio-medical unit in accordance with the present invention.

FIG. 35 is a mechanical diagram of another embodiment of an embedded bio-medical unit 10 in an artificial body part (e.g., a metal screw or plate), which includes multiple cavities as the bio-medical mounting mechanism. As shown, the bio-medical unit 10 is mounted within, or at least partially within, one cavity and the antenna and/or coil is mounted within, or at least partially within, another cavity. Note that a plurality of embedded bio-medical units 10 may be utilized for diagnostics and/or treatment of health issues. For example, the plurality of bio-medical units 10 may be embedded in a plurality of non-metal plates that are attached to a bone to repair a break. The bio-medical units 10 may monitor the position of the bone to detect any undesired stress, cracks, breaks, and/or any other potential issues.

Figure 36:
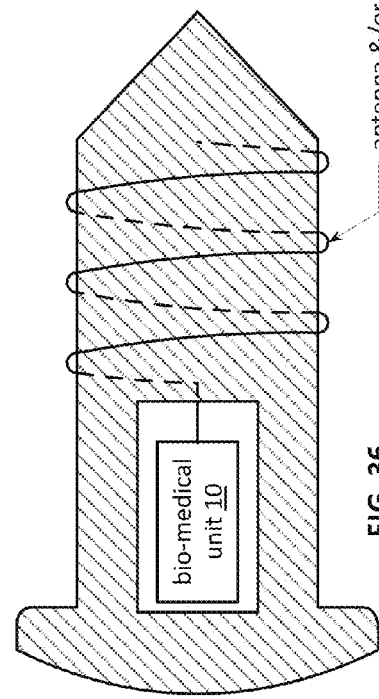
FIG. 36 is a diagram of another embodiment of a surgical fastener including a bio-medical unit in accordance with the present invention.

FIG. 36 is a mechanical diagram of an embedded bio-medical unit 10 in an artificial body part (e.g., a metal screw or plate), which includes a cavity as the bio-medical mounting mechanism. As shown, the bio-medical unit 10 is mounted within, or at least partially within, the cavity and the antenna and/or coil for the bio-medical unit 10 is contained, or functions as, the threads of a screw. Note that a plurality of embedded bio-medical units 10 may be utilized for diagnostics and/or treatment of health issues. For example, the plurality of bio-medical units 10 may be embedded in a plurality of non-metal screws that are attached to a bone to repair a break. The bio-medical units 10 may monitor the position of the bone to detect any undesired stress, cracks, breaks, and/or any other potential issues.

Figure 37:
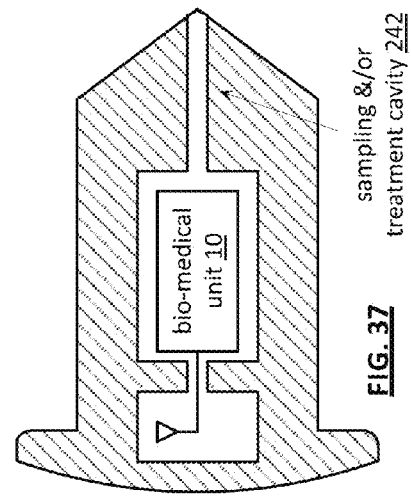
FIG. 37 is a diagram of another embodiment of a surgical fastener including a bio-medical unit in accordance with the present invention.

FIG. 37 is a mechanical diagram of another embodiment of an embedded bio-medical unit 10 in a solid object (e.g., a non-metal screw or plate). At least one cavity is provided in the solid object to contain the bio-medical unit 10 and an antenna. A duct extends from the outside surface of the solid object to the at least one cavity containing the bio-medical unit 10 to provide a sampling and/or treatment cavity 242. The bio-medical device functional module 54 may gather data and/or deliver a treatment (e.g., drugs) via the duct by coupling the bio-medical unit to the body. Note that a plurality of embedded bio-medical units 10 may be utilized for diagnostics and/or treatment of health issues. For example, the plurality of bio-medical units 10 may be embedded in a plurality of non-metal screws that are attached to a bone to repair a break. The bio-medical units 10 may administer a drug treatment from time to time (e.g., bone cancer drugs) via the sampling and/or treatment cavity 242.

Figure 38:
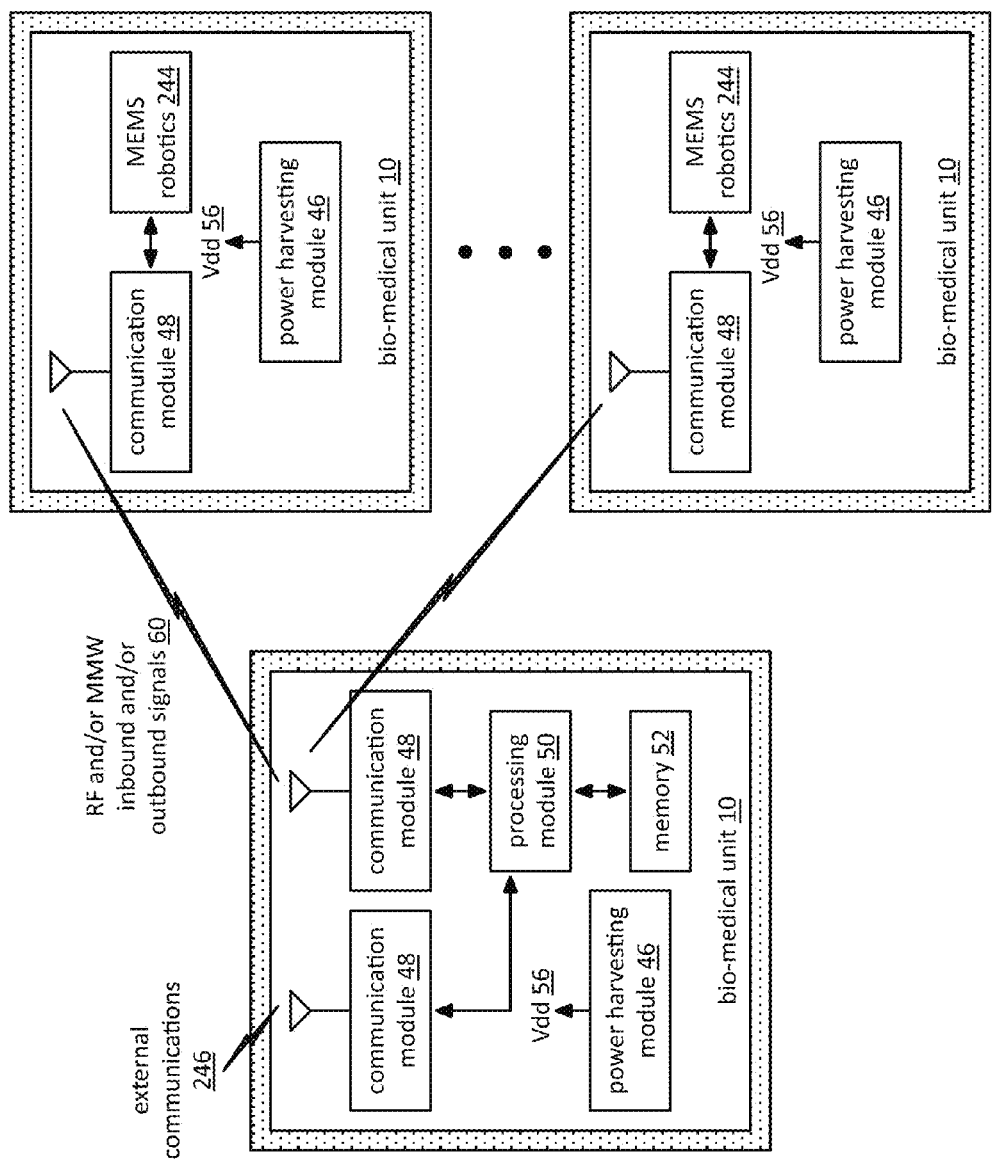
FIG. 38 is a diagram of an embodiment of a network of bio-medical units that include MEMS robotics in accordance with the present invention.

FIG. 38 is a schematic block diagram of an embodiment of a parent bio-medical unit (on the left) communicating with an external unit to coordinates the functions of one or more children bio-medical units 10 (on the right). The parent unit includes a communication module 48 for external communications, a communication module 48 for communication with the children units, the processing module 50, the memory 52, and the power harvesting module 46. Note that the parent unit may be implemented one or more chips and may in the body or one the body.

Each of the child units includes a communication module 48 for communication with the parent unit and/or other children units, a MEMS robotics 244, and the power harvesting module 46. The MEMS robotics 244 may include one or more of a MEMS technology saw, drill, spreader, needle, injection system, and actuator. The communication module 48 may support RF and/or MMW inbound and/or outbound signals 60 to the parent unit such that the parent unit may command the child units in accordance with external communications commands.

In an example of operation, the patent bio-medical unit receives a communication from the external source, where the communication indicates a particular function the child units are to perform. The parent unit processes the communication and relays relative portions to the child units in accordance with a control mode. Each of the child units receives their respective commands and performs the corresponding functions to achieve the desired function.

Figure 39:
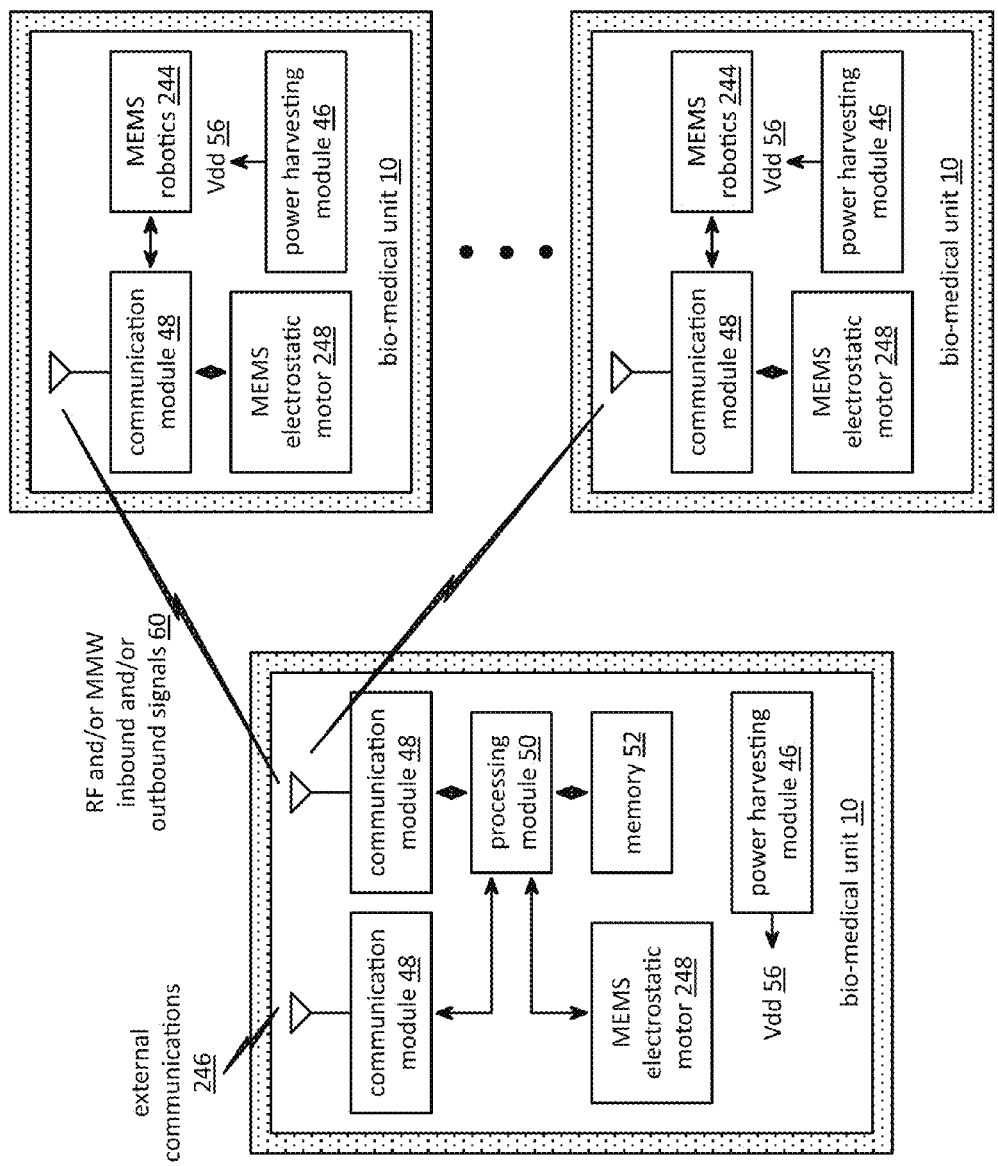
FIG. 39 is a diagram of another embodiment of a network of bio-medical units that include MEMS robotics in accordance with the present invention.

FIG. 39 is a schematic block diagram of another embodiment of a plurality of task coordinated bio-medical units 10 including a parent bio-medical unit 10 (on the left) and one or more children bio-medical units 10 (on the right). The parent unit may be implemented one or more chips and may in the body or one the body. The parent unit may harvest power in conjunction with the power booster 84.

The parent unit includes the communication module 48 for external communications, the communication module 48 for communication with the children units, the processing module 50, the memory 52, a MEMS electrostatic motor 248, and the power harvesting module 46. The child unit includes the communication module 48 for communication with the parent unit and/or other children units, a MEMS electrostatic motor 248, the MEMS robotics 244, and the power harvesting module 46. Note that the child unit has fewer components as compared to the parent unit and may be smaller facilitating more applications where smaller bio-medical units 10 enhances their effectiveness.

The MEMS robotics 244 may include one or more of a MEMS technology saw, drill, spreader, needle, injection system, and actuator. The MEMS electrostatic motor 248 may provide mechanical power for the MEMS robotics 244 and/or may provide movement propulsion for the child unit such that the child unit may be positioned to optimize effectiveness. The child units may operate in unison to affect a common task. For example, the plurality of child units may operate in unison to saw through a tissue area.

The child unit communication module 48 may support RF and/or MMW inbound and/or outbound signals 60 to the parent unit such that the parent unit may command the children units in accordance with external communications commands.

The child unit may determine a control mode and operate in accordance with the control mode. The child unit determines the control mode based on one or more of a command from a parent bio-medical unit, external communications, a preprogrammed list, and/or in response to sensor data. Note that the control mode may include autonomous, parent (bio-medical unit), server, and/or peer as previously discussed.

Figure 40:
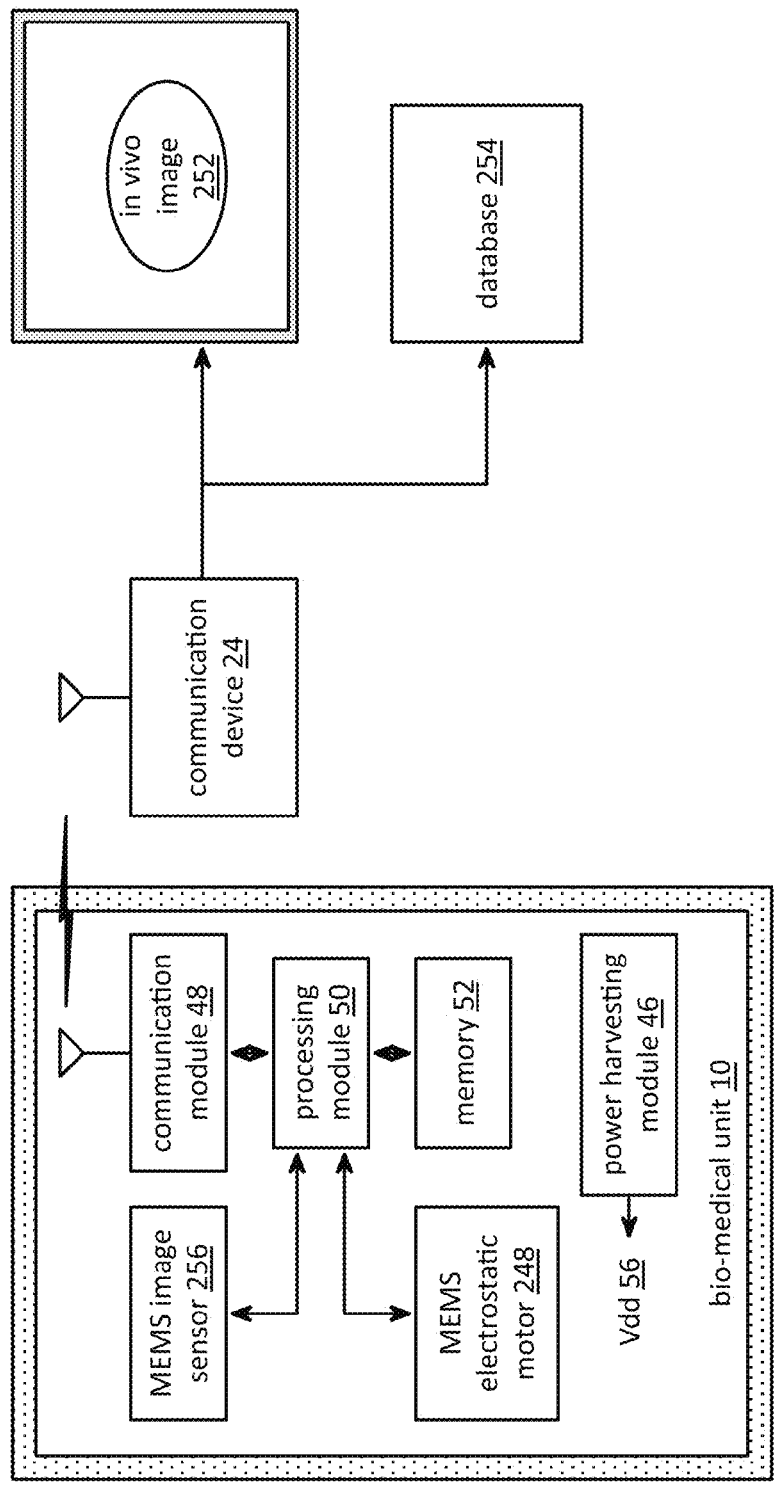
FIG. 40 is a diagram of an embodiment of a bio-medical unit collecting image data in accordance with the present invention.

FIG. 40 is a schematic block diagram of an embodiment of a bio-medical unit 10 based imaging system that includes the bio-medical unit 10, the communication device 24, a database 254, and an in vivo image unit 252. The bio-medical unit 10 may perform scans and provide the in vivo image unit 252 with processed image data for diagnostic visualization.

The bio-medical unit 10 includes a MEMS image sensor 256, the communication module 48 for external communications with the communication device, the processing module 50, the memory 52, the MEMS electrostatic motor 248, and the power harvesting module 46. In an embodiment the bio-medical unit 10 and communication device 24 communicate directly. In another embodiment, the bio-medical unit 10 and communication device 24 communicate through one or more intermediate networks (e.g., wireline, wireless, cellular, local area wireless, Bluetooth, etc.). The MEMS image sensor 256 may include one or more sensors scan types for optical signals, MMW signals, RF signals, EM signals, and/or sound signals.

The in vivo unit 252 may send a command to the bio-medical unit 10 via the communication device 24 to request scan data. The request may include the scan type. The in vivo unit 252 may receive the processed image data from the bio-medical unit 10, compare it to data in the database 254, process the data further, and provide image visualization.

Figure 41:
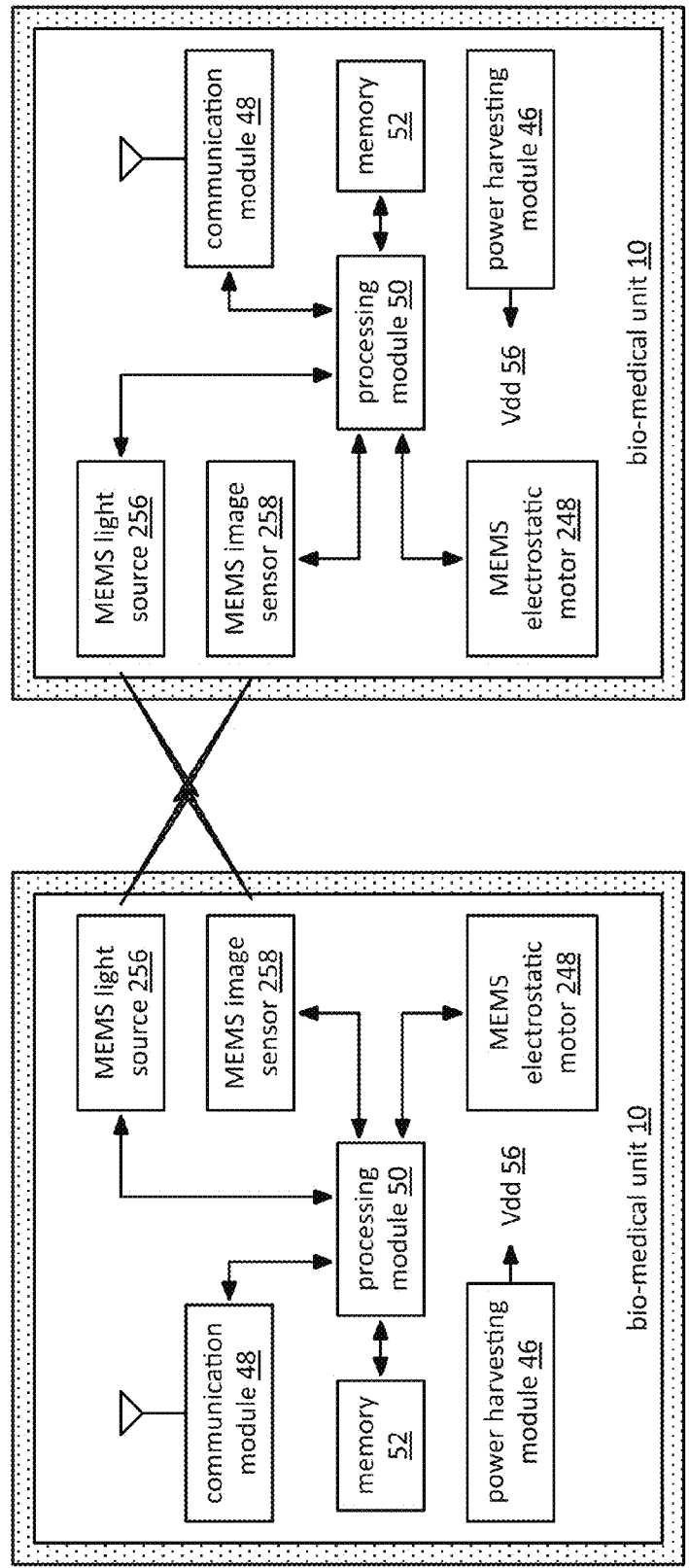
FIG. 41 is a diagram of another embodiment of a network of bio-medical units communicating via light signaling in accordance with the present invention.

FIG. 41 is a schematic block diagram of an embodiment of a communication and diagnostic bio-medical unit 10 pair where the pair utilize an optical communication medium between them to analyze material between them (e.g., tissue, blood flow, air flow, etc,) and to carry messages (e.g., status, commands, records, test results, scan data, processed scan data, etc.).

The bio-medical unit 10 includes a MEMS light source 256, a MEMS image sensor 258, the communication module 48 (e.g., for external communications with the communication device 24), the processing module 50, the memory 52, the MEMS electrostatic motor 248 (e.g., for propulsion and/or tasks), and the power harvesting module 46. The bio-medical unit 10 may also include the MEMS light source 256 to facilitate the performance of light source tasks. The MEMS image sensor 258 may be a camera, a light receiving diode, or infrared receiver. The MEMS light source 256 may emit visible light, infrared light, ultraviolet light, and may be capable of varying or sweeping the frequency across a wide band.

The processing module 50 may utilize the MEMS image sensor 258 and the MEMS light source 256 to communicate with the other bio-medical unit 10 using pulse code modulation, pulse position modulation, or any other modulation scheme suitable for light communications. The processing module 50 may multiplex messages utilizing frequency division, wavelength division, and/or time division multiplexing.

The bio-medical optical communications may facilitate communication with one or more other bio-medical units 10. In an embodiment, a star architecture is utilized where one bio-medical unit 10 at the center of the star communicates to a plurality of bio-medical units 10 around the center where each of the plurality of bio-medical units 10 only communicate with the bio-medical unit 10 at the center of the star. In an embodiment, a mesh architecture is utilized where each bio-medical unit 10 communicates as many of the plurality of other bio-medical units 10 as possible and where each of the plurality of bio-medical units 10 may relay messages from one unit to another unit through the mesh.

The processing module 50 may utilize the MEMS image sensor 258 and the MEMS light source 256 of one bio-medical unit 10 to reflect light signals off of matter in the body to determine the composition and position of the matter. In another embodiment, the processing module 50 may utilize the MEMS light source 256 of one bio-medical unit 10 and the MEMS image sensor 258 of a second bio-medical unit 10 to pass light signals through matter in the body to determine the composition and position of the matter. The processing module 50 may pulse the light on and off, sweep the light frequency, vary the amplitude and may use other perturbations to determine the matter composition and location.

Figure 42:
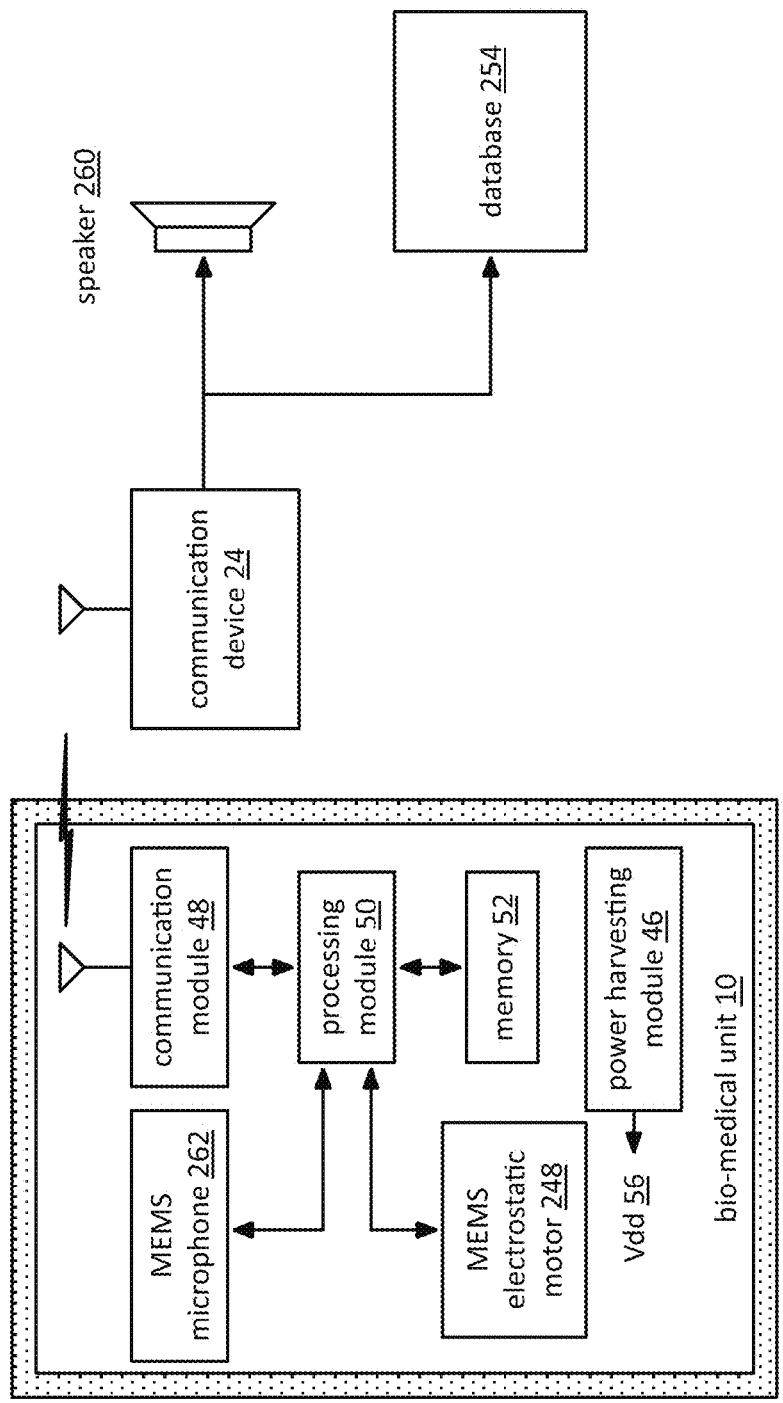
FIG. 42 is a diagram of an embodiment of a bio-medical unit collecting audio and/or ultrasound data in accordance with the present invention.

FIG. 42 is a schematic block diagram of an embodiment of a bio-medical unit 10 based sounding system that includes the bio-medical unit 10, the communication device 24, the database 254, and a speaker 260. The bio-medical unit 10 may perform scans and provide the speaker 260 with processed sounding data for diagnostic purposes via the communication device 24.

The bio-medical unit 10 includes a MEMS microphone 262, the communication module 48 for external communications with the communication device 24, the processing module 50, the memory 52, the MEMS electrostatic motor 248, and the power harvesting module 46. In an embodiment the bio-medical unit 10 and communication device 24 communicate directly. In another embodiment, the bio-medical unit 10 and communication device 24 communicate through one or more intermediate networks (e.g., wireline, wireless, cellular, local area wireless, Bluetooth, etc.) The MEMS microphone 262 may include one or more sensors to detect audible sound signals, sub-sonic sound signals, and/or ultrasonic sound signals.

The processing module 50 may produce the processed sounding data based in part on the received sound signals and in part on data in the database 254. The processing module 50 may retrieve data via the communication module 48 and communication device 24 link from the database 254 to assist in the processing of the signals (e.g., pattern matching, filter recommendations, sound field types). The processing module 50 may process the signals to detect objects, masses, air flow, liquid flow, tissue, distances, etc. The processing module 50 may provide the processed sounding data to the speaker 260 for audible interpretation. In another embodiment, the bio-medical unit 10 assists an ultrasound imaging system by relaying ultrasonic sounds from the MEMS microphone 262 to the ultrasound imaging system instead of to the speaker 260.

Figure 43:
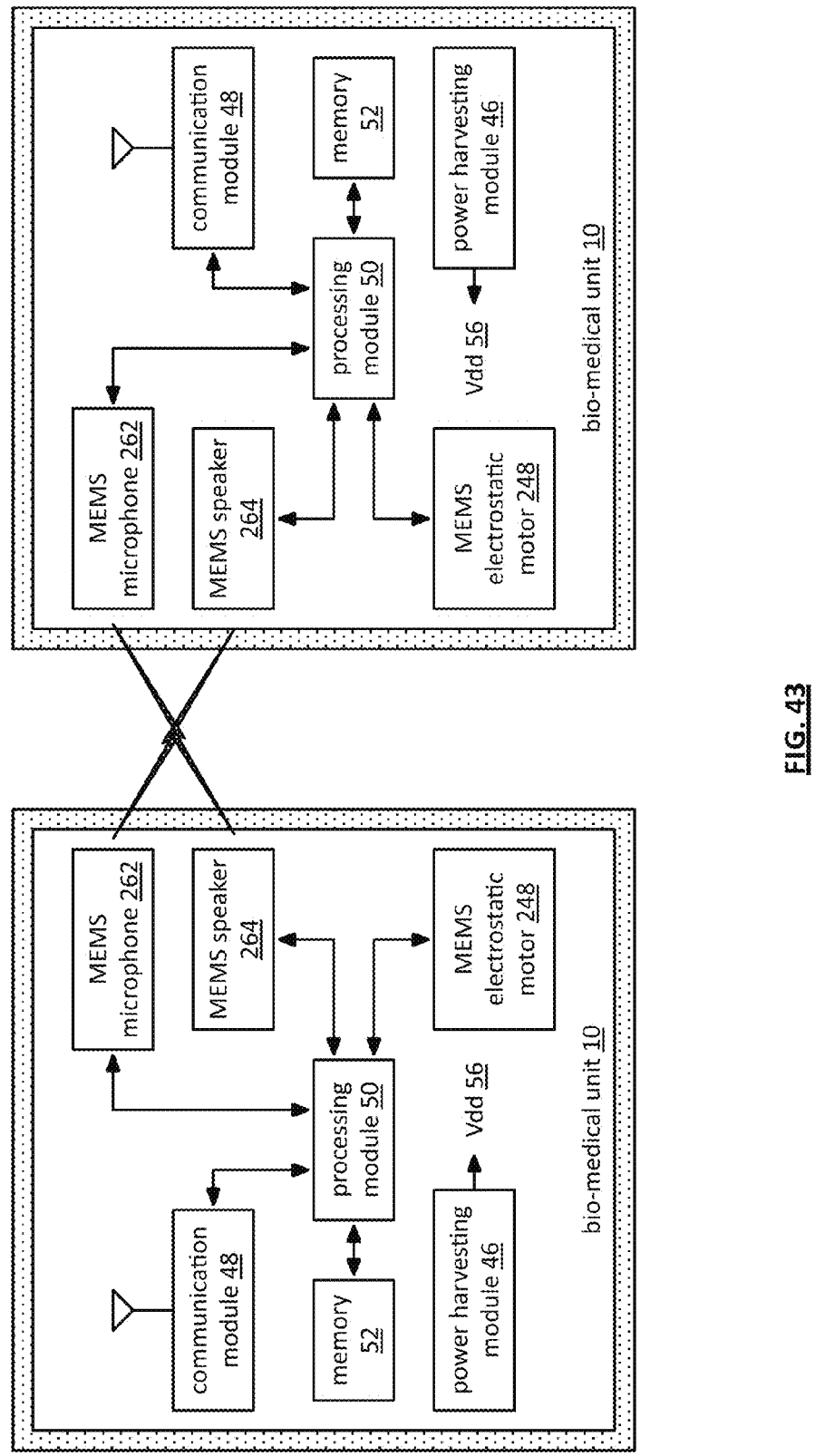
FIG. 43 is a diagram of another embodiment of a network of bio-medical units communicating via audio and/or ultrasound signaling in accordance with the present invention.

FIG. 43 is a schematic block diagram of another embodiment of a bio-medical unit 10 communication and diagnostic pair where the pair utilize an audible communication medium between them to analyze material between them (e.g., tissue, blood flow, air flow, etc,) and to carry messages (e.g., status, commands, records, test results, scan data, processed scan data, etc.). The bio-medical unit 10 includes the MEMS microphone 262, a MEMS speaker 264, the communication module 48 (e.g., for external communications with the communication device), the processing module 50, the memory 52, the MEMS electrostatic motor 248 (e.g., for propulsion and/or tasks), and the power harvesting module 46. The bio-medical unit 10 may also include the MEMS speaker 264 to facilitate performance of sound source tasks.

The MEMS microphone 262 and MEMS speaker 264 may utilize audible sound signals, sub-sonic sound signals, and/or ultrasonic sound signals and may be capable of varying or sweeping sound frequencies across a wide band. The processing module 50 may utilize the MEMS microphone 262 and MEMS speaker 264 to communicate with the other bio-medical unit 10 using pulse code modulation, pulse position modulation, amplitude modulation, frequency modulation, or any other modulation scheme suitable for sound communications. The processing module 50 may multiplex messages utilizing frequency division and/or time division multiplexing.

The bio-medical sound based communications may facilitate communication with one or more other bio-medical units 10. In an embodiment, a star architecture is utilized where one bio-medical unit 10 at the center of the star communicates to a plurality of bio-medical units 10 around the center where each of the plurality of bio-medical units 10 only communicate with the bio-medical unit 10 at the center of the star. In an embodiment, a mesh architecture is utilized where each bio-medical unit 10 communicates as many of the plurality of other bio-medical units 10 as possible and where each of the plurality of bio-medical units 10 may relay messages from one unit to another unit through the mesh.

The processing module 50 may utilize the MEMS microphone 262 and MEMS speaker 264 of one bio-medical unit 10 to reflect sound signals off of matter in the body to determine the composition and position of the matter. In another embodiment, the processing module 50 may utilize the MEMS microphone 262 of one bio-medical unit 10 and the MEMS speaker 264 of a second bio-medical unit 10 to pass sound signals through matter in the body to determine the composition and position of the matter. The processing module 50 may pulse the sound on and off, sweep the sound frequency, vary the amplitude and may use other perturbations to determine the matter composition and location.

Figure 44:
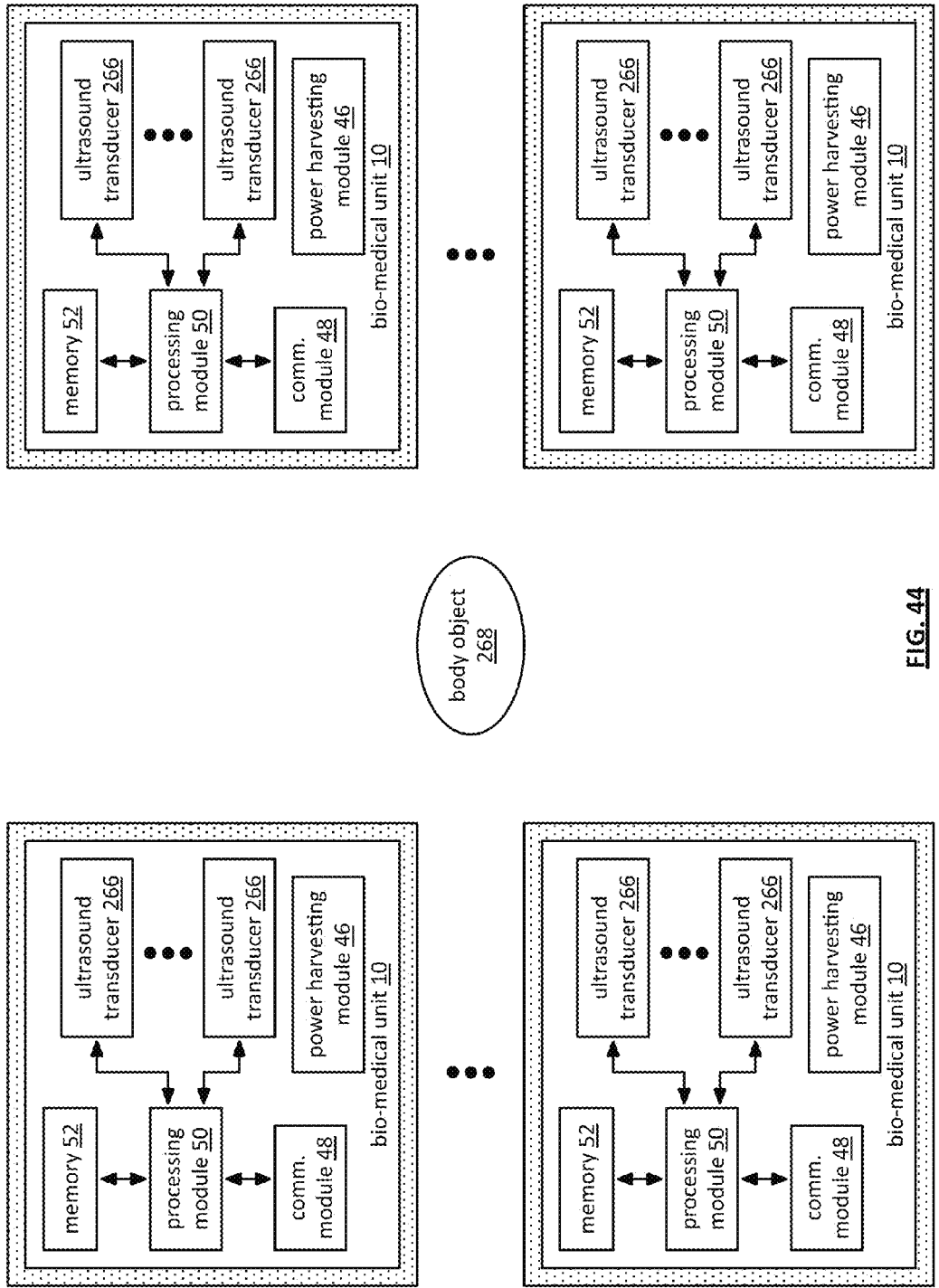
FIG. 44 is a diagram of an embodiment of a network of bio-medical units collecting ultrasound data in accordance with the present invention.

FIG. 44 is a schematic block diagram of an embodiment of a sound based imaging system including a plurality of bio-medical units 10 utilizing short range ultrasound signals in the 2-18 MHz range to facilitate imaging a body object 268. The bio-medical unit 10 includes at least one ultrasound transducer 266, the communication module 48 (e.g., for external communications with the communication device and for communications with other bio-medical units), the processing module 50, the memory 52, and the power harvesting module 46. The ultrasound transducer 266 may be implemented utilizing MEMS technology.

The processing module 50 controls the ultrasonic transducer 266 to produce ultrasonic signals and receive resulting reflections from the body object 268. The processing module 50 may coordinate with the processing module 50 of at least one other bio-medical unit 10 to produce ultrasonic signal beams (e.g., constructive simultaneous phased transmissions directed in one direction) and receive resulting reflections from the body object. The processing module 50 may perform the coordination and/or the plurality of processing modules 50 may perform the coordination. In embodiment, the plurality of processing modules 50 receives coordination information via the communication module 48 from at least one other bio-medical unit 10. In another embodiment, the plurality of processing modules 50 receives coordination information via the communication module 48 from an external communication device.

The processing module produces processed ultrasonic signals based on the received ultrasonic reflections from the body object 268. For example, the processed ultrasonic signals may represent a sonogram of the body part. The processing module 50 may send the processed ultrasonic signals to the external communication device and/or to one or more of the plurality of bio-medical units 10.

Figure 45:
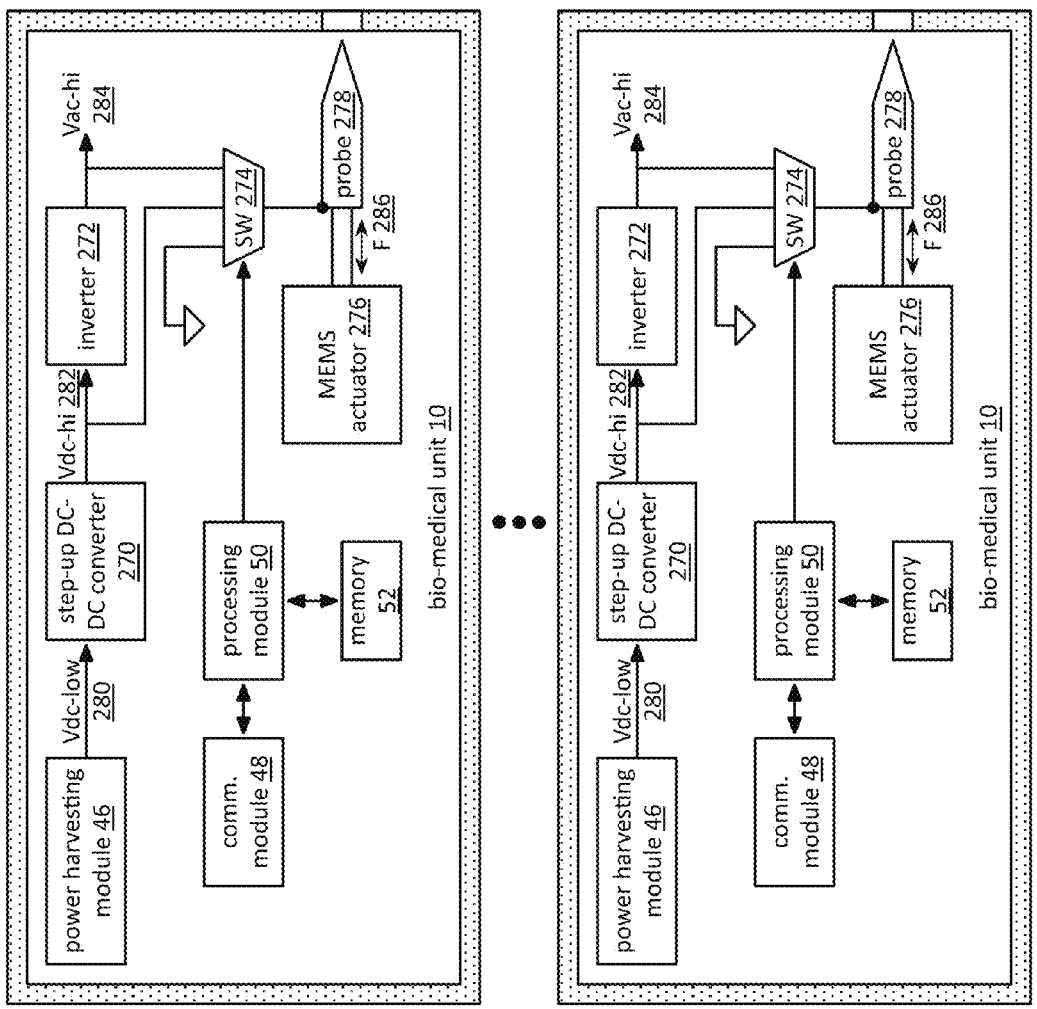
FIG. 45 is a diagram of an embodiment of a network of bio-medical units for facilitating electrical stimulus treatment in accordance with the present invention.

FIG. 45 is a schematic block diagram of an embodiment of an electric stimulation system that includes one or more bio-medical units 10 capable of delivering an electric stimulation current (i.e., an electrotherapy signal). Each of the bio-medical unit 10 includes a step-up DC-DC converter 270, an inverter 272, a switch 274, a probe 278, a nanotechnology or MEMS actuator 276, the communication module 48 (e.g., for external communications with the communication device and for communications with other bio-medical units), the processing module 50, the memory 52, and the power harvesting module 46.

In an example of operation, the processing module 50 receives a message via the communication 48 that causes the processing module 50 to generate a high voltage stimuli command as the command message. The pain management functional module (e.g., the MEMS actuator 276, the switch 274, and/or the probe 278) receives the high voltage stimuli command and, in response thereto, establishes a common ground with another bio-medical unit (e.g., couple via a probe or other electrical means). The pain management functional module then produces a high voltage in accordance with the high voltage stimuli command.

For instance, the step-up DC-DC converter 270 converts a lower DC voltage 280 output of the power harvesting module 46 to a higher DC voltage 282. The inverter transforms the higher DC voltage 282 to a higher AC voltage 284. The switch 274, based on the command message, selects one of at least a ground potential, the higher DC voltage 282, or the higher AC voltage 284 to apply to the probe 278. The probe 278 applies the selected voltage potential to an object adjacent to the bio-medical unit 10 (e.g., a body point such as an acupuncture point, a nerve, a muscle, etc.) when the probe 278 is mechanically extended beyond the outer encasement of the bio-medical unit 10. For example, the processing module 50 may control the MEMS actuator 276 to move the probe 278 into position via force 286 to deliver the selected voltage potential or to retract the probe 278 when it is not in use. In another example, the probe 278 is in contact with the body without mechanical movement. Note that the processing module 50 may control the MEMS actuator 276 to move the probe 278 into position to deliver a ground potential voltage potential to simulate an acupuncture application.

In another example of operation, the power harvesting module converts an electromagnetic signal into a supply voltage, which powers the processing module and the pain management functional module. The processing module determines a body point for application of pain treatment and a pain treatment duration. For example, the processing module determines the body point to correspond to a ligament with in a person's knee. In addition, the processing module determines the pain treatment duration to be 15 minutes. The processing module that generates a control signal regarding the body point and the pain treatment duration and provides the control signal to the pain management functional module.

In one instance, the communication module 48 receives a communication from an external communication device 24 regarding the pain treatment. For example, the communication module receives a wireless communication signal from an external communication device 24 and converts it into a baseband or near-baseband signal. The processing module converts the baseband or near-baseband signal into a pain treatment command. From the pain treatment command, the processing module determines at least one of the body point and the treatment duration.

The pain management functional module receives the control signal and, in response thereto, generates an electrotherapy signal, which is directed toward the body point. For example, the pain management functional module includes an actuator module 276, a needle probe 278, and a high-voltage generator (e.g., 270 and 272, which will be described in greater detail with reference to FIG. 24). In response to the control signal, the actuator module 276 applies a force 286 upon the needle probe 278 such that the needle probe is positioned proximal to the body point. When in that position, the high-voltage generator produces the electrotherapy signal that is applied to the body point via the needle probe 278. While not shown in FIG. 23, the bio-medical unit may further include a cleaning module that is operable to clean the needle probe.

In general, electro-therapy, as applied by the bio medical unit 10, may be used for such medical treatment as deep brain stimulation for treating neurological diseases, to speed up wound healing, to improve bone healing, to provide pain management, to improve joint range of motion, to treat neuromuscular dysfunction, to improve motor control, to retard muscle atrophy, to improve local blood flow, to improve tissue repair by enhancing microcirculation and protein synthesis, to restore integrity of connective and dermal tissue, to function as a pharmacological agent, improve continence, and/or to relax muscle spasms.

Figure 46:
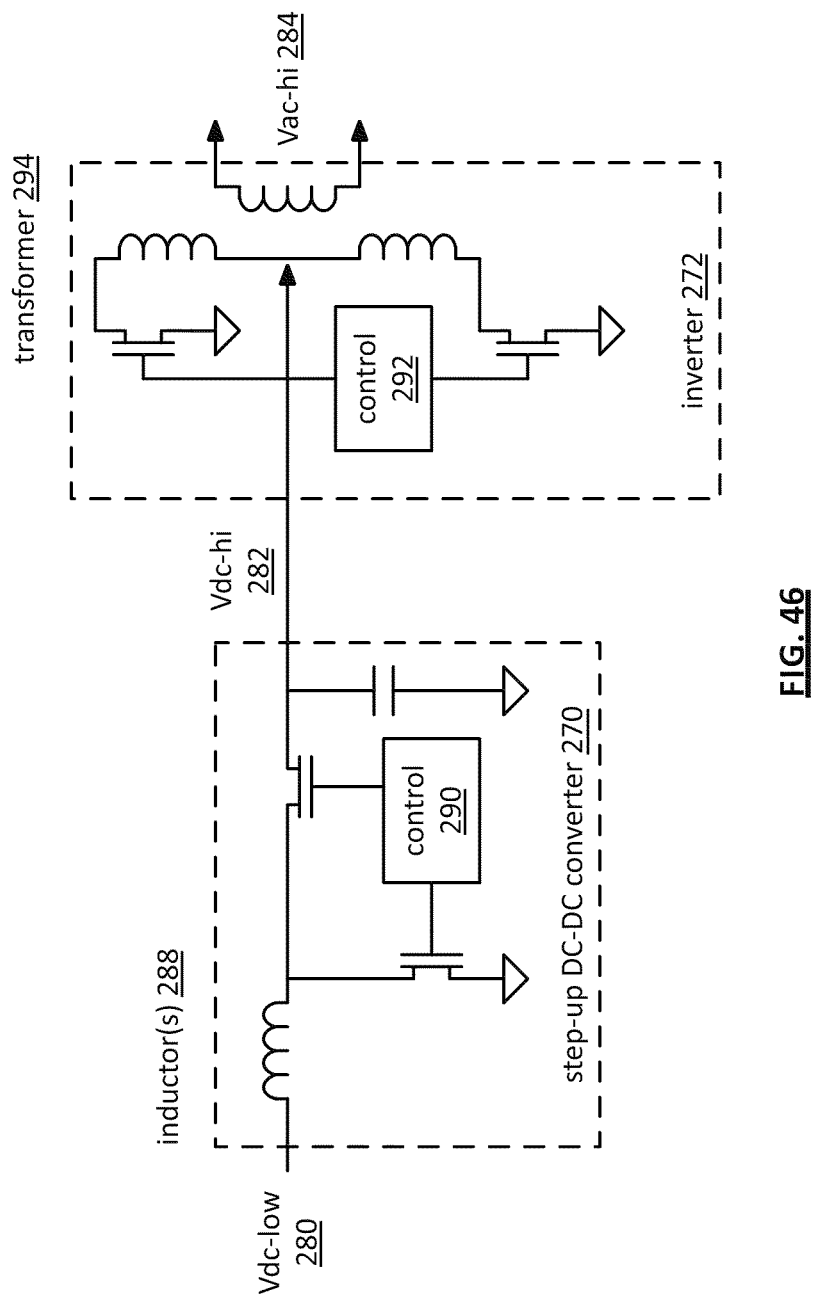
FIG. 46 is a diagram of an embodiment of power conversion modules in a bio-medical unit of FIG. 45 in accordance with the present invention.

FIG. 46 is a schematic diagram of an embodiment of a voltage conversion circuit including a step-up DC-DC converter 270 and an inverter 272. The step-up DC-DC converter 270 includes an input inductor 288, a pair of switching transistors, a smoothing capacitor, and a control circuit 290. The inductor 288 may be implemented as one or more air core inductors 288. The control circuit 290 operates the switching transistors to interact with the inductor 288 and capacitor to provide the higher DC voltage 282 potential at the output.

The inverter 272 includes a transformer 294, a pair of switching transistors, and a control circuit 292. The transformer 294 may be implemented as a 1:1 air core transformer 294 (or other turn ratios) with three single turn coils on different layers with the output between the input coil layers. The control circuit 292 operates the switching transistors to interact with the inductance of the transformer 294 to provide an alternating current at the input of the transformer 294 to produce the higher AC voltage 284 potential at the output.

FIG. 47 is a schematic block diagram of an embodiment of a communication module 48 of a bio-medical unit coupled to one or more antenna assemblies 94. The communication module 48 includes a MMW transmitter 132, a MMW receiver 136, and a local oscillator generator 298 (LOGEN) and is coupled to the processing module 50. While not shown in the present figure, the bio-medical unit includes at least one power harvesting module that converts an electromagnetic signal into one or more supply voltages. The one or more supply voltages power the other components of the bio-medical unit. Note that the bio-medical unit and the antenna assemblies 94 may be implemented on one or more integrated circuit (IC) dies within a common housing.

The one or more antenna assemblies 94 may include a common transmit and receive antenna; a separate transmit antenna and a separate receive antenna; a common array of antennas; and/or an array of transmit antennas and an array of receive antennas. The one or more antenna assemblies 94 may further include a transmission line, an impedance matching circuit, and/or a transmit/receive switch, duplexer, and/or isolator. Each of the antennas of the one or more antenna assemblies 94 may be a leaky antenna as shown in FIG. 48 (discussed below) and may be implemented using MEMS and/or nano technology 296.

In an example of operation, the bi-medical unit is exposed to an electromagnetic signal as previously discussed. The power harvesting module generates a supply voltage from the electromagnetic signal, where the supply voltage powers the communication module 48 and the processing module 50. When powered, the processing module may receive a command regarding a bio-medical function via the communication module. A communication device external to the host body or another bio-medical unit may initiate the command, which is received as an inbound (or downstream) RF or MMW signal by the communication module.

In response to receiving the command, the processing module interprets it to determine whether the bio-medical function includes a radio frequency transmission (e.g., for cancer treatment, imaging, pain blocking, etc.). When the bio-medical function includes a radio frequency transmission, the processing module determines a desired radiation pattern for the antenna assembly. For example, the desired radiation pattern may have a primary lobe perpendicular to the surface of the antenna, a primary lobe at an angle from perpendicular to the surface, beamformed, etc. Various radiation patterns are shown in FIGS. 49 and 50.

Having determined the desired radiation pattern, the processing module then determines an operating frequency based on the desired radiation pattern. For example, the processing module may use a look up table to determine the operating frequency for a particular desired radiation pattern, which are determined based on the properties of the antenna(s). Once the operating frequency is established, the antenna assembly will transmit outbound RF and/or MMW signals and receive inbound RF and/or MMW signals in accordance with the desired radiation pattern.

As a more specific example, after establishing the operating frequency, the processing module generates a continuous wave treatment signal in accordance with the bio-medical function (e.g., for pain blocking, for cancer treatment, etc.). In addition, the processing module generates a transmit local oscillation control signal in accordance with the bio-medical function.

The local oscillation generator 298 receives the transmit local oscillation control signal and generates, in accordance therewith, a transmit local oscillation. The transmitter section receives the continuous wave treatment signal (which may be a DC signal, a fixed frequency AC signal with a constant or varying amplitude, or a varying frequency AC with a constant or varying amplitude) and the transmit local oscillation. The transmitter section mixes the continuous wave treatment signal and the transmit local oscillation to produce a radio frequency (RF) continuous wave (CW) signal and outputs it to the antenna assembly, which transmits the RF CW signal in accordance with the radiation pattern.

As another more specific example, after establishing the operating frequency, the processing module generates a pulse treatment signal in accordance with the bio-medical function (e.g., for pain blocking, for cancer treatment, etc.). In addition, the processing module generates a transmit local oscillation control signal in accordance with the bio-medical function.

The local oscillation generator 298 receives the transmit local oscillation control signal and generates, in accordance therewith, a transmit local oscillation. The transmitter section receives the pulse treatment signal (which may be a pulse train having a constant amplitude and a constant frequency, a pulse train having a constant amplitude and varying frequency, a pulse train having a varying amplitude and a constant frequency) and the transmit local oscillation. The transmitter section mixes the pulse treatment signal and the transmit local oscillation to produce a radio frequency (RF) pulse signal and outputs it to the antenna assembly, which transmits the RF pulse signal in accordance with the radiation pattern.

As another more specific example, the processing module determines that the bio-medical function includes a radio frequency transmission for generating an image of a body object. In this instance, the processing module determines a varying operating frequency such that the radiation pattern of the antenna assembly varies to produce a varying radiation pattern. In addition, the processing module generates a varying transmit local oscillation control signal, which it provides to the local oscillation generator.

The transmitter section generates outbound radio frequency (RF) and/or MMW signals that have varying frequencies and outputs them to the antenna assembly. With the frequencies of the outbound RF signals, the radiation pattern of the antenna assembly will vary. As such, a radar-sweeping pattern is generated.

The receiver section 136 receives a representation of the outbound RF signal (e.g., reflection, refraction, and/or a determined absorption). The receive section converts the representation of the outbound RF signal into an inbound symbol stream. The processing module generates a radar image of a body object based on the outbound RF signal and the representation of the outbound RF signal.

In addition to providing RF transmissions to support a bio-medical function, the bio-medical unit may also communicate with an external communication device and/or with another bio-medical unit within the host body. For instance, the processing module determines a second radiation pattern for communication with a communication device external to the host body using a second operating frequency, wherein the antenna assembly has the second radiation pattern for the communication at the second operating frequency. Such communications may be concurrent with the supporting of the bio-medical function or in a time division multiplexed manner.

As another example of operation, or in furtherance of the preceding example, the antenna assembly includes adjustable physical characteristics such that the radiation pattern can be adjusted. For instance, an antenna of the antenna assembly includes a first conductive layer and a second conductive layer. The second conductive layer is substantially parallel to the first conductive layer and is separated by a distance from the first conductive layer. The second conductive layer includes a plurality of substantially equally spaced non-conductive areas corresponding to a particular range of frequencies to facilitate the radiation pattern for the particular range of frequencies. To varying the radiation patterns, the distance between the first and second conductive layers may be varied, the geometry of the non-conductive areas may be varied, and/or the spacing between the non-conductive areas may be varied.

Continuing with this example, the processing module receives a command regarding a bio-medical function via the communication module and interprets it. When the bio-medical function includes a radio frequency transmission, the processing module determines antenna parameters for the antenna assembly (e.g., for desired radiation patterns, determine distance between conductive layers, geometry of the non-conductive areas, and/or spacing between the non-conductive layers). The processing module then generates an antenna control signal based on the antenna parameters, which it provides to the antenna assembly.

FIG. 48 is a schematic block diagram of an embodiment of a leaky antenna 94 that includes a channel and/or waveguide having a first conductive layer and a second conductive layer. The layers are separated by a distance (d), which may be fixed or variable. The second conductive layer includes a series of openings (e.g., non-conductive areas) to facilitate the radiation of an electromagnetic signal 300 that is traveling down the waveguide. The geometry and/or spacing between the openings may be fixed or variable.

The leaky antenna pattern (e.g., direction) is a function of at least the size of the openings, the distance between openings, and the frequency of operation. For example, the distance between openings is set to about one wavelength of the nominal center frequency of operation. With the physical dimensions static, the leaky antenna pattern may be adjusted with changes to frequency of operation (e.g., above and below the center frequency).

FIG. 49 is a diagram of an antenna pattern at a first frequency of operation where the antenna pattern 302 may be substantially in the 90° direction with respect to the length wise direction of the leaky antenna waveguide. In this example, the distance between the openings of the leaky antenna 94 is substantially the same as the length of the wavelength of the frequency of operation.

FIG. 50 is a diagram of an antenna pattern at a second frequency of operation where the antenna pattern 304 may be substantially off of the 90° direction with respect to the length wise direction of the leaky antenna waveguide. In this example, the distance between the openings of the leaky antenna 94 is different than the length of the wavelength of the frequency of operation.

Figure 51:
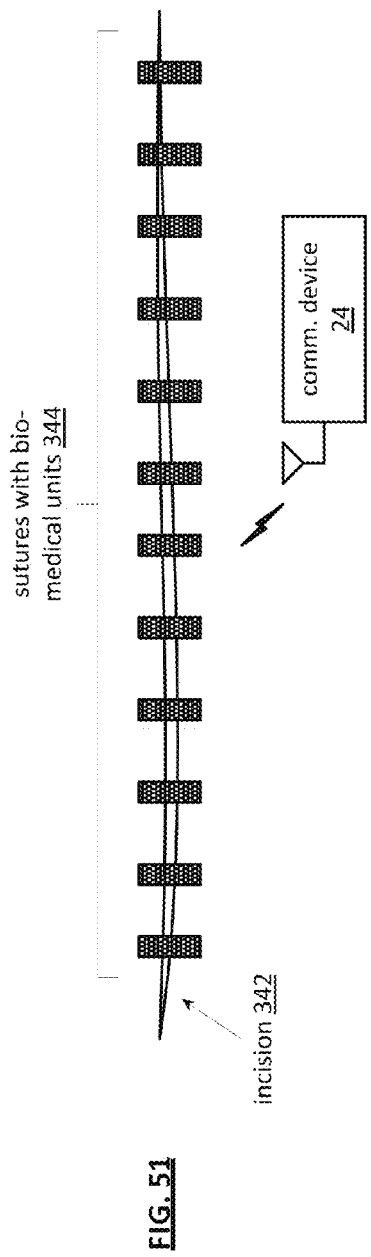
FIG. 51 is a diagram of an embodiment of a network of bio-medical units within sutures in accordance with the present invention.

FIG. 51 is a schematic block diagram of an embodiment of a system of suture bio-medical units 344 where a plurality of bio-medical units 344 are positioning along an incision 342 suture line to diagnose and treat the healing process. The bio-medical units 344 may be attached to or embedded in the suture materials including staples, glue, tape, thread, wire, etc. The suture material may be metal or non-metal.

The bio-medical units 344 may communicate with each other and/or with a communication device 24 to communicate status information and/or commands and/or to coordinate performance of functions. For instance, the bio-medical unit 344 may perform diagnostics including monitoring temperature, taking images, pinging the incision with ultrasound, pinging the incision with MMW radar to produce diagnostic information. The bio-medical unit 344 may produce diagnostic results based on the diagnostic information. The diagnostic results may include indications or probabilities of high temperature, infection, behind the expected healing schedule, and/or ahead of the expected healing schedule.

The bio-medical unit 344 may send the diagnostic results and/or diagnostic information to other bio-medical units 10, 344 and/or to the communication device 24 for further processing or commands. The bio-medical unit 344 may determine to treat the healing process. The treatments may include administering medication, applying laser treatment, applying ultrasound treatment, grasping, sawing, drilling, and/or providing an electronic stimulus. The determination may be based on one of more of a predetermination, a command, and/or an adaptive algorithm (e.g., to heal the incision faster).

Figure 52:
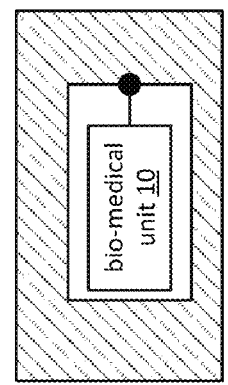
FIG. 52 is a diagram of an embodiment of a suture including a bio-medical unit in accordance with the present invention.

FIG. 52 is a mechanical diagram of another embodiment of an embedded bio-medical unit 10 in a solid object (e.g., a metal suture). A cavity is provided in the solid object to contain the bio-medical unit 10. The communication module 48 antenna port of the bio-medical unit 10 may be coupled to the solid object such that the solid object provides an antenna and/or coil function. The communication module 48 may utilize the solid object as the antenna for MMW communication, RF communication, and/or EM signaling. The bio-medical unit 10 may communicate sensed data produced from the functional module 54. Note that a plurality of embedded bio-medical units 10 may be utilized for diagnostics and/or treatment of health issues. For example, the plurality of bio-medical units 10 may be embedded in a plurality of metal sutures that are to affect the healing of an incision. The bio-medical units 10 may monitor the healing process to detect any undesired issues.

Figure 53:
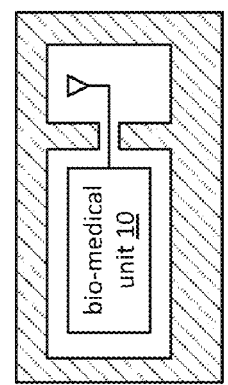
FIG. 53 is a diagram of another embodiment of a suture including a bio-medical unit in accordance with the present invention.

FIG. 53 is a mechanical diagram of another embodiment of an embedded bio-medical unit 10 in a solid object (e.g., a non-metal suture). At least one cavity is provided in the solid object to contain the bio-medical unit 10 and an antenna. The communication module 48 antenna is contained in at least one solid object cavity such that the antenna may receive and send MMW communication, RF communication, and/or EM signaling. The bio-medical unit 10 may communicate sensed data produced from the functional module. Note that a plurality of embedded bio-medical units 10 may be utilized for diagnostics and/or treatment of health issues. For example, the plurality of bio-medical units 10 may be embedded in a plurality of metal sutures that are to affect the healing of an incision. The bio-medical units 10 may monitor the healing process to detect any undesired issues.

Figure 54:
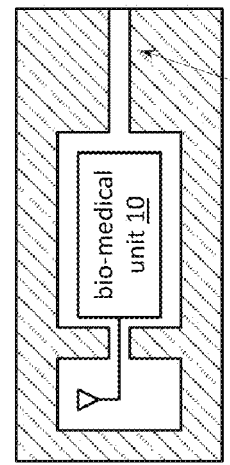
FIG. 54 is a diagram of another embodiment of a suture including a bio-medical unit in accordance with the present invention.

FIG. 54 is a mechanical diagram of another embodiment of an embedded bio-medical unit 10 in a solid object (e.g., a non-metal suture). At least one cavity is provided in the solid object to contain the bio-medical unit 10 and an antenna. A sampling and/or treatment cavity 242 extends from the outside surface of the solid object to the at least one cavity containing the bio-medical unit 10. The bio-medical device 10 functional module 54 may gather data and/or deliver a treatment (e.g., drugs) via the sampling and/or treatment cavity 242 by coupling the bio-medical unit 10 to the body.

The communication module 48 antenna is contained in at least one solid object cavity such that the antenna may receive and send MMW communication, RF communication, and/or EM signaling. The bio-medical unit 10 may communicate sensed data produced from the functional module 54. Note that a plurality of embedded bio-medical units 10 may be utilized for diagnostics and/or treatment of health issues. For example, the plurality of bio-medical units 10 may be embedded in a plurality of metal sutures that are to affect the healing of an incision. The bio-medical units 10 may monitor the healing process to detect any undesired issues. The bio-medical units 10 may administer a drug treatment from time to time (e.g., infection fighting drugs) in response to the undesired issues. In another embodiment, the bio-medical unit 10 may administer an electric potential to mediate pain.

Figure 55:
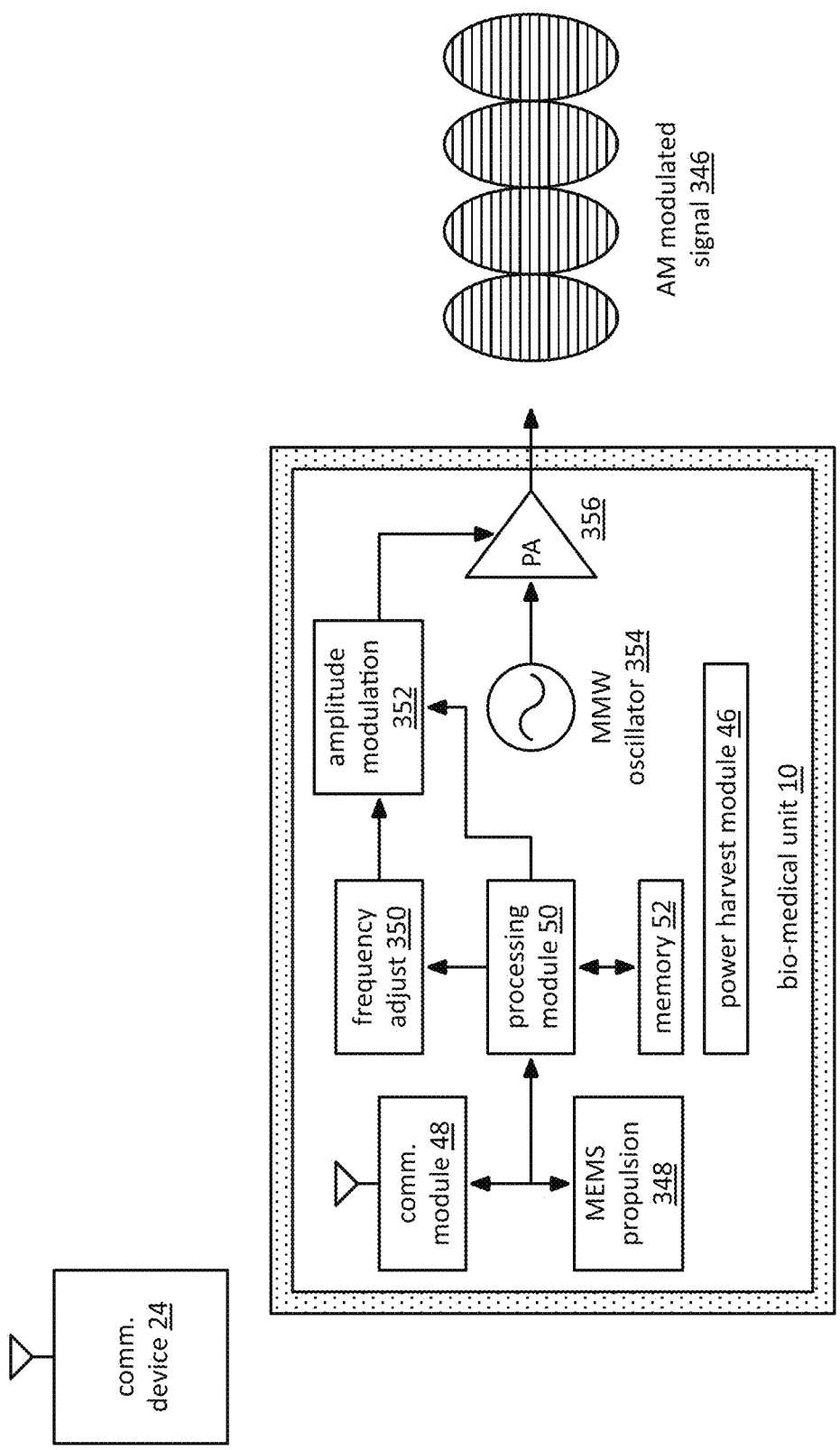
FIG. 55 is a diagram of an embodiment of a bio-medical unit facilitating pain blocking in accordance with the present invention.

FIG. 55 is a schematic block diagram of an embodiment of a pain blocking bio-medical unit 10 to provide an amplitude modulated (AM) signal 346 to facilitate gate control of pain. The bio-medical unit 10 includes the communication module 48 (e.g., for external communications with the communication device and for communications with other bio-medical units), a MEMS propulsion 348, the processing module 50, the memory 52, the power harvesting module 46, a frequency adjust 350, an amplitude modulation 352, a MMW oscillator 354, and a power amplifier 356 (PA).

The bio-medical unit 10 may communicate with other bio-medical units 10 and/or with the communication device 24 to communicate status information and/or commands. The bio-medical unit 10 may receive a command from the communication device 24 to reposition, adjust the MMW frequency, and transmit MMW signals to mediate pain. In another embodiment, the communication device 24 may send a command to a plurality of bio-medical units 10 to coordinate the formation of a beam to better pinpoint the pain mediation.

The processing module 50 may control the MEMS propulsion 348 to reposition the bio-medical unit 10. The processing module 50 may determine how to control the frequency adjust 350 and amplitude modulation 352 to affect the pain based on a command, a predetermination, and/or an adaptive algorithm (e.g., that detects local pain). The processing module 50 controls the frequency adjust 350 and amplitude modulation 352 in accordance with the determination such that the MMW oscillator 354 fed PA 356 generates an amplitude modulated signal 346.

Figure 56:
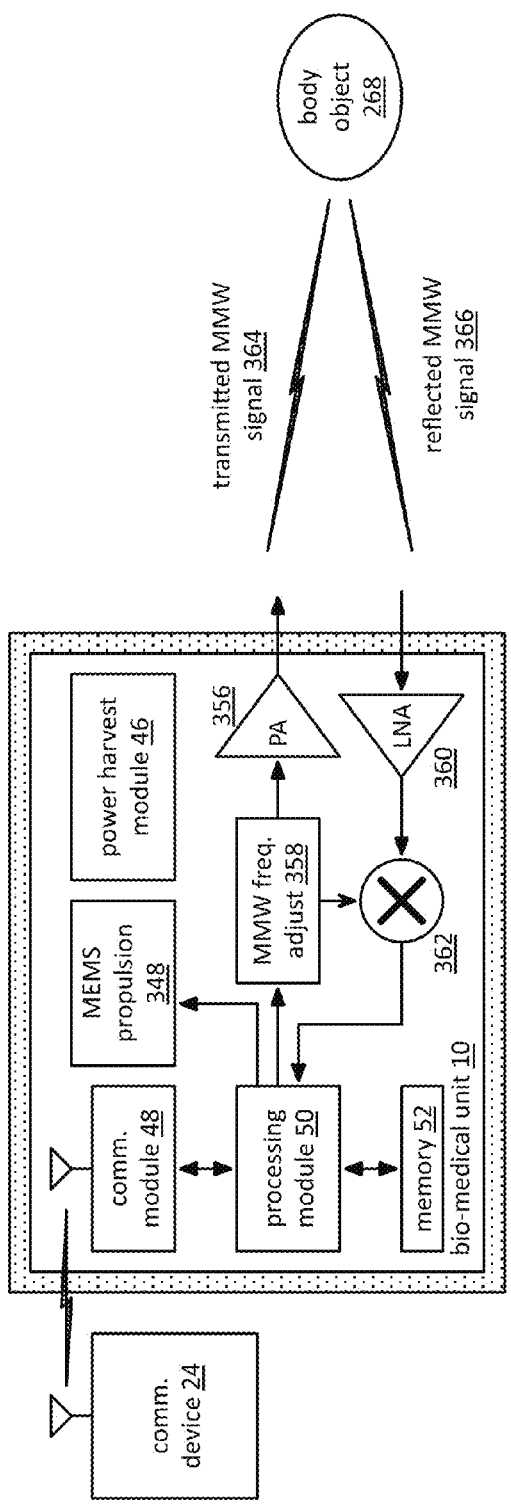
FIG. 56 is a diagram of an embodiment of a bio-medical unit determining relative distance using Doppler shifting in accordance with the present invention.

FIG. 56 is a schematic block diagram of an embodiment of a Doppler radar bio-medical unit to provide a distancing radar function to determine the location of a body object 268. The bio-medical unit 10 includes the communication module 48 (e.g., for external communications with the communication device and for communications with other bio-medical units), the MEMS propulsion 348, the processing module 50, the memory 52, the power harvesting module 46, a MMW frequency adjust 358, a mixer 362, a low noise amplifier 360 (LNA), and a power amplifier 356 (PA). The bio-medical unit 10 may communicate with other bio-medical units 10 and/or with a communication device 24 to communicate status information and/or commands.

The bio-medical unit 10 may send a transmitted MMW signal 364 to the body object 268 and receive a reflected MMW signal 366 from the body object. 268. Some of the transmitted MMW signal energy is absorbed, reflected in other directions, and/or transmitted to other directions. The bio-medical unit 10 forms a Doppler radar sequence by varying the frequency of the transmitted MMW signal 364 over a series of transmission steps. The bio-medical unit 10 may determine the distance and location information based on the reflected MMW signal 366 in response to the Doppler radar.

The bio-medical unit 10 may receive a command from the communication device 24 to reposition, adjust the MMW frequency, and transmit MMW signals to perform the Doppler radar function. In another embodiment, the communication device 24 may send a command to a plurality of bio-medical units 10 to coordinate the formation of a beam to better pinpoint the body object. In yet another embodiment, the communication device 24 may send a command to a plurality of bio-medical units 10 to coordinate the Doppler radar function from two, three or more bio-medical units 10 to triangulate the body object location based on the distance information.

The processing module 50 may control the MEMS propulsion 348 to reposition the bio-medical unit 10. The processing module 50 may determine how to control the MMW frequency adjust 358 to affect the distance information detection based on a command, a predetermination, and/or an adaptive algorithm (e.g., that detects course distance ranges at first and fine tunes the accuracy over time). The processing module 50 controls the MMW frequency adjust 358 in accordance with the determination such that the PA 356 generates the desired transmitted MMW signal 364. The LNA 360 amplifies the reflected MMW signal 366 and the mixer 362 down converts the signal such that the processing module 50 receives and processes the signal.

Figure 57:
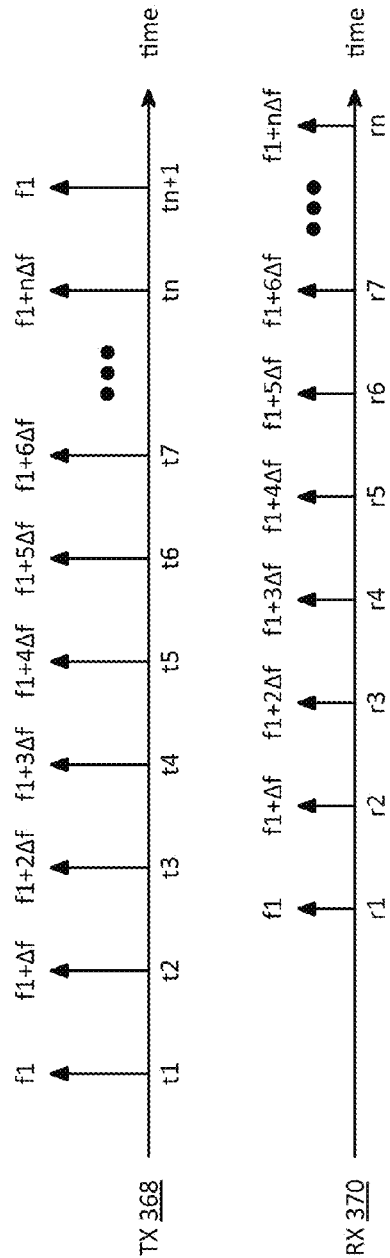
FIG. 57 is a diagram of an example of determining relative distance using Doppler shifting in accordance with the present invention.

FIG. 57 is a timing diagram of an embodiment of a Doppler radar sequence where a transmit (TX) series 368 of MMW transmissions for the transmit sequence of transmitted MMW signals 364 and a receive (RX) series of MMW receptions for the receive sequence of reflected MMW signals 366. The transmit sequence may modulo cycle through frequencies that are $\Delta f$ apart (e.g., f1, f1+2 $\Delta f$, f1+2 $\Delta f$, ... ) spaced apart in time at intervals t1, t2, t3, etc.

The receive sequence 370 provides the reflection signals in the same order of the transmit sequence 368 with small differences in time (e.g., at r1, r2, r3, ... ) and frequency. The processing module 50 determines distance information based on the small differences in time and frequency between the receive sequence 370 and the originally transmitted sequence 368.

Figure 58:
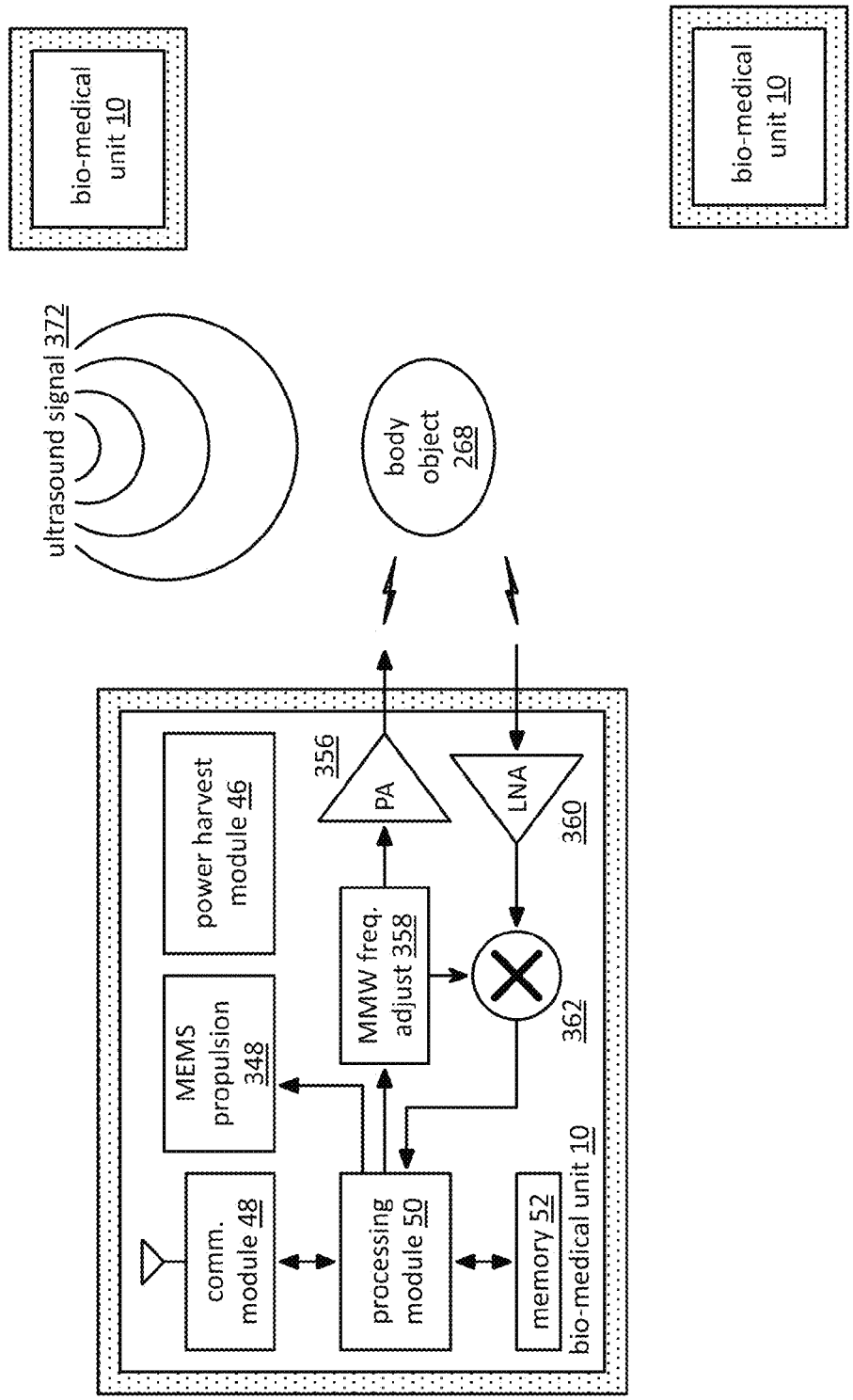
FIG. 58 is a diagram of an example of determining vibrations using Doppler shifting and ultrasound in accordance with the present invention.

FIG. 58 is a schematic block diagram of another embodiment of a Doppler radar bio-medical unit 10 to provide a distancing radar function to determine the density of a body object 268 when the body object 268 vibrates from an ultrasound signal 372. At least one other bio-medical unit 10 may provide the ultrasound signal.

The bio-medical unit 10 includes the communication module 48 (e.g., for external communications with the communication device and for communications with other bio-medical units), the MEMS propulsion 348, the processing module 50, the memory 52, the power harvesting module 46, a MMW frequency adjust 358, a mixer 362, a low noise amplifier 360 (LNA), and a power amplifier 356 (PA). The bio-medical unit 10 may communicate with other bio-medical units 10 and/or with a communication device 24 to communicate status information and/or commands. For example, the bio-medical unit 10 may coordinate with at least one other bio-medical unit 10 to provide the ultrasound signal 372.

The bio-medical unit 10 may send a transmitted MMW signal 364 to the body object and receive a reflected MMW signal 366 from the body object. Some of the transmitted MMW signal energy is absorbed by the body object, reflected in other directions, and/or transmitted to other directions.

Note that the reflections may vary as a function of the ultrasound signal where the reflected signals vary according to the density of the body object.

The bio-medical unit 10 forms a Doppler radar sequence by varying the frequency of the transmitted MMW signal 364 over a series of transmission steps. The bio-medical unit 10 may determine the distance and density based on the reflected MMW signal 366 in response to the Doppler radar.

The bio-medical unit 10 may receive a command from the communication device 24 to reposition, adjust the MMW frequency, and transmit MMW signals 364 to perform the Doppler radar function. In another embodiment, the communication device 24 may send a command to a plurality of bio-medical units 10 to coordinate the formation of a beam to better pinpoint the body object 268 and determine the density. In yet another embodiment, the communication device 24 may send a command to a plurality of bio-medical units 10 to coordinate the Doppler radar function from two, three or more bio-medical units 10 to triangulate the body object 268 location based on the distance information.

The processing module 50 may control the MEMS propulsion 348 to reposition the bio-medical unit 10. The processing module 50 may determine how to control the MMW frequency adjust 358 to affect the distance and density information detection based on a command, a predetermination, and/or an adaptive algorithm (e.g., that detects course distance ranges at first and fine tunes the accuracy over time). The processing module 50 controls the MMW frequency adjust 358 in accordance with the determination such that the PA 356 generates the desired transmitted MMW signal 364. The LNA 360 amplifies the reflected MMW signal 366 and the mixer 362 down converts the signal such that the processing module 50 receives and processes the signal.

Figure 59:
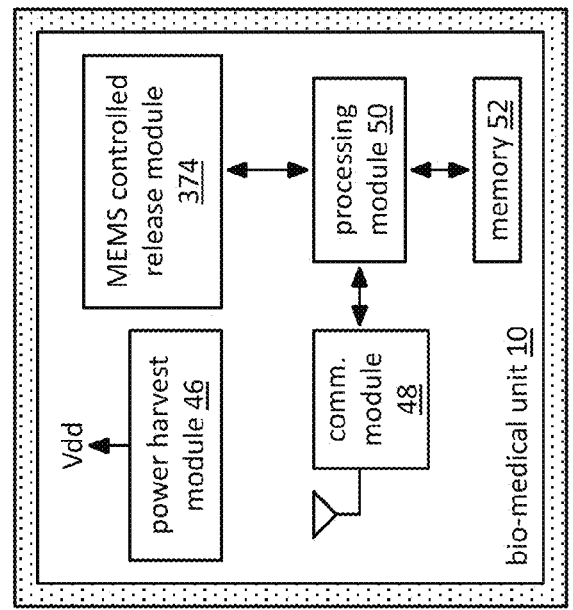
FIG. 59 is a diagram of an embodiment of a bio-medical unit including a controlled release module in accordance with the present invention.

FIG. 59 is a schematic block diagram of an embodiment of a controlled release bio-medical unit 10 that administers potentially complex medications. The bio-medical unit 10 includes a MEMS controlled release module 374, the communication module 50 (e.g., for external communications with the communication device and for communications with other bio-medical units), the processing module 50, the memory 52, and the power harvesting module 46.

The bio-medical unit 10 may communicate with other bio-medical units 10 and/or with a communication device 24 to communicate status information and/or commands. For example, the bio-medical unit 10 may coordinate with at least one other bio-medical unit 10 to provide the administration of medications. The processing module 50 may determine when and how to administer the medication based on a command, a predetermination, and/or an adaptive algorithm (e.g., that detects local pain).

The MEMS controlled release module 374 may contain materials that comprise medications and a unit ID to identify the materials. The processing module 50 may control the MEMS controlled release module 374 to mix particular materials to produce a desired medication in accordance with the unit ID, and the determination of the when and how to administer the medication.

Figure 60:
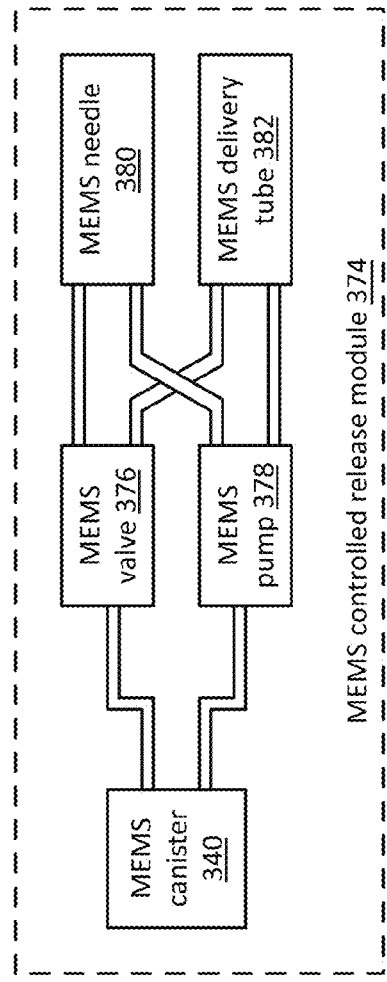
FIG. 60 is a diagram of an embodiment of a controlled release module in accordance with the present invention.

FIG. 60 is a schematic block diagram of an embodiment of a MEMS controlled release module 374 that controls the formation and delivery of medications created with materials previously stored in the MEMS controlled release module 374. The MEMS controlled release module 374 may include a MEMS canister 340, a MEMS valve 376, a MEMS pump 378, a MEMS needle 380, MEMS delivery tube 382, and pathways between the elements. The MEMS canister 340 holds one or more materials. The MEMS valve 376 may control the flow of a material. The MEMS pump 378 may actively move a material. The MEMS needle 380 may facilitate injection of the medication. The MEMS delivery tube 382 may facilitate delivery of the medication.

The MEMS controlled release module 374 may receive requests and/or commands from the processing module 50 including request for unit ID, commands to mix 10% material A and 90% material B, a command to inject the needle, and/or a command to administer the mixture through a MEMS needle 380 and/or MEMS delivery tube 382.

Figure 61:
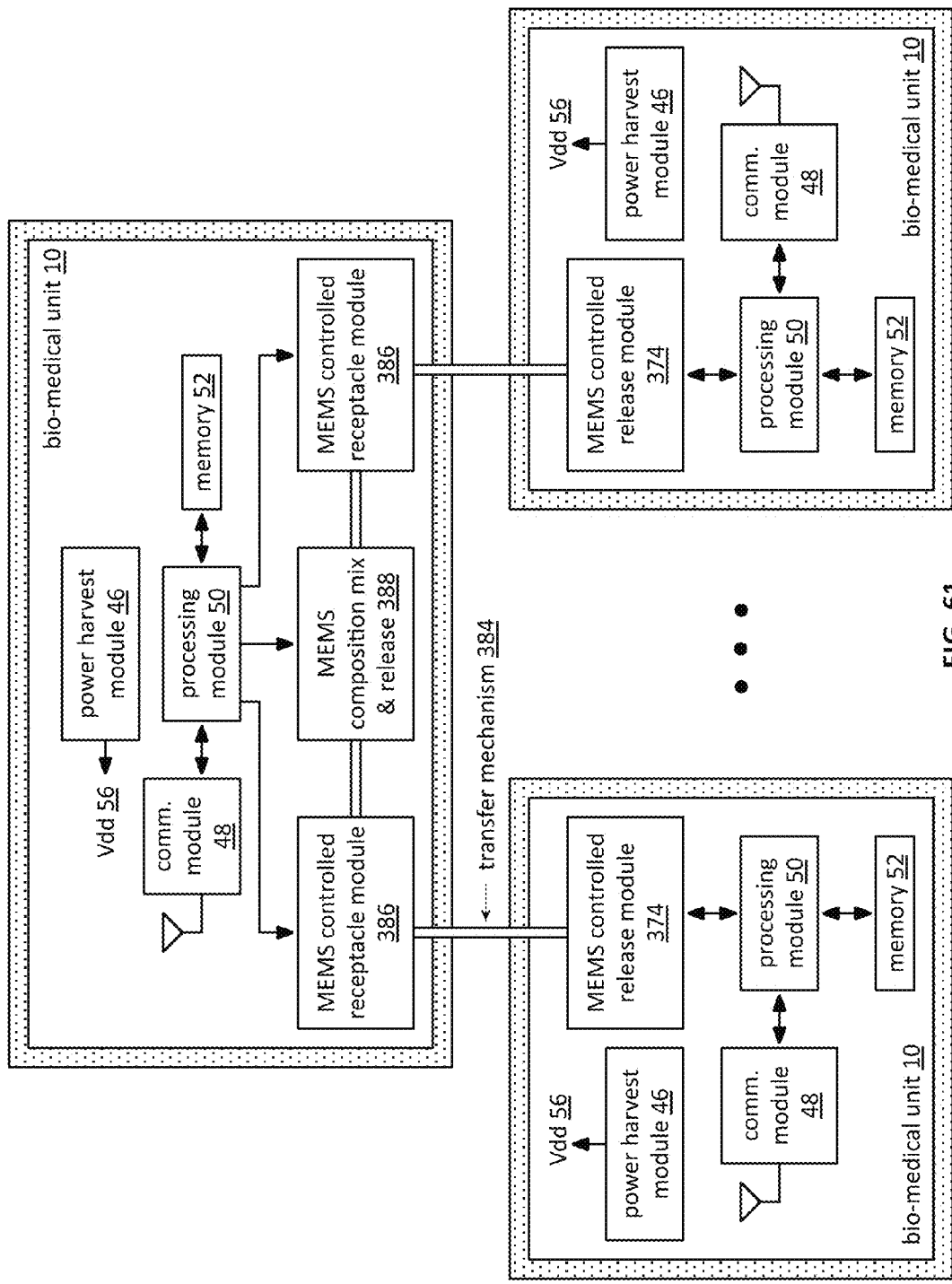
FIG. 61 is a diagram of an embodiment of a system of bio-medical units for controlled release of a medication in accordance with the present invention.

FIG. 61 is a schematic block diagram of an embodiment of a controlled release bio-medical unit 10 system that administers potentially complex medications. A plurality of bio-medical units 10 transfers (e.g., from at least one unit to another), mixes, and administers the medications.

A first type of bio-medical unit 10 includes a MEMS controlled release module 374, the communication module 48 (e.g., for external communications with the communication device and for communications with other bio-medical units), the processing module 50, the memory 52, and the power harvesting module 46. The first type of bio-medical unit 10 substantially provides the medication ingredients to a second type of bio-medical unit 10.

The second type of bio-medical unit 10 includes at least one MEMS controlled receptacle module 386, a MEMS composition mix and release 388, the communication module 48 (e.g., for external communications with the communication device and for communications with other bio-medical units), the processing module 50, the memory 52, and the power harvesting module 46. The second type of bio-medical unit 10 substantially mixes the final medication and administers the medication.

The first and second types of bio-medical unit 10 may communicate with other bio-medical units 10 and/or with a communication device 24 to communicate status information and/or commands. For example, the second type bio-medical unit 10 may coordinate with at least one first type of bio-medical unit 10 to provide the administration of medications.

The processing module 50 of the second type of bio-medical unit 10 may determine when and how to administer the medication based on a command, a predetermination, and/or an adaptive algorithm (e.g., that detects local pain). The processing module 50 of the second type of bio-medical unit 10 may determine which of the plurality of the first type of bio-medical units 10 contain the required materials based on a unit ID status update, a command, and/or a predetermination.

The processing module 50 of the second type of bio-medical unit 10 may send a command to the plurality of the first type of bio-medical units 10 to dock with the second type of bio-medical unit 10 and transfer the required materials to the MEMS controlled receptacle module 386 of the second type of bio-medical unit 10. The processing module 50 of the second type of bio-medical unit 10 may control the MEMS composition mix and release 388 to mix the required materials from the plurality of first type of bio-medical units 10. The processing module 50 of the second type of bio-medical unit 10 may control the MEMS composition mix and release 388 to release the mixture in accordance with the determination of the when and how to administer the medication.

Figure 62:
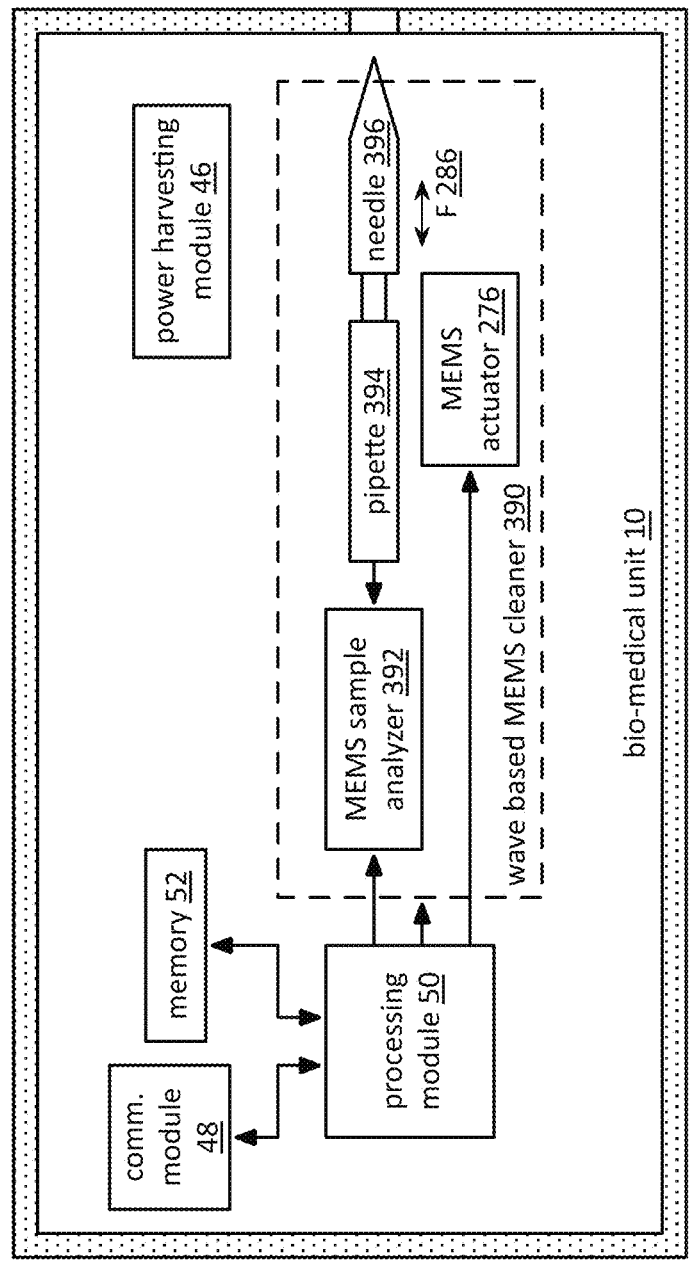
FIG. 62 is a diagram of an embodiment of a bio-medical unit including sampling modules in accordance with the present invention.

FIG. 62 is a schematic block diagram of an embodiment of a self-cleaning sampling bio-medical unit 10 where a wave based MEMS cleaner 390 facilitates cleaning of a sampling sub-system. The bio-medical unit 10 includes the wave based MEMS cleaner 390 for a MEMS sample analyzer 392, a pipette 394, a needle 396, and a MEMS actuator 276. The bio-medical unit 10 also includes the communication module 48 (e.g., for external communications with the communication device and for communications with other bio-medical units), the processing module 50, the memory 52, and the power harvesting module 46.

The processing module 50 may determine when to perform a sampling and cleaning of the sampling sub-system based on a command, a predetermination, and/or an adaptive algorithm (e.g., based on a sample history). The processing module 50 may precede each sampling with a cleaning, follow each sampling with a cleaning, or some combination of both.

The processing module 50 may command the wave based MEMS cleaner 390 to clean the components of the sampling sub-system. The wave based MEMS cleaner 390 may perform the cleaning with one or methods including heating, vibrating, RF energy, laser light, and/or sound waves. In another embodiment, the bio-medical unit 10 includes a MEMS canister 340 with a cleaning agent that is released during the cleaning sequence and expelled through the needle 396.

The processing module 50 may command the MEMS actuator 276 to apply force 286 to move the needle 396 into the sampling position where the needle 396 is exposed to the outside of the bio-medical unit 10 (e.g., extends into the body). The pipette 394 moves the sample from the needle 396 to the MEMS sample analyzer 392.

The MEMS sample analyzer 392 provides the processing module 50 with sample information, which may include blood analysis, pH analysis, temperature, oxygen level, other gas levels, toxin analysis, medication analysis, and/or chemical analysis. The processing module 50 may process the sample information to produce processed sample information. The processing module 50 may send the processed sample information to another bio-medical unit 10 or to a communication unit 24 for further processing.

Figure 63:
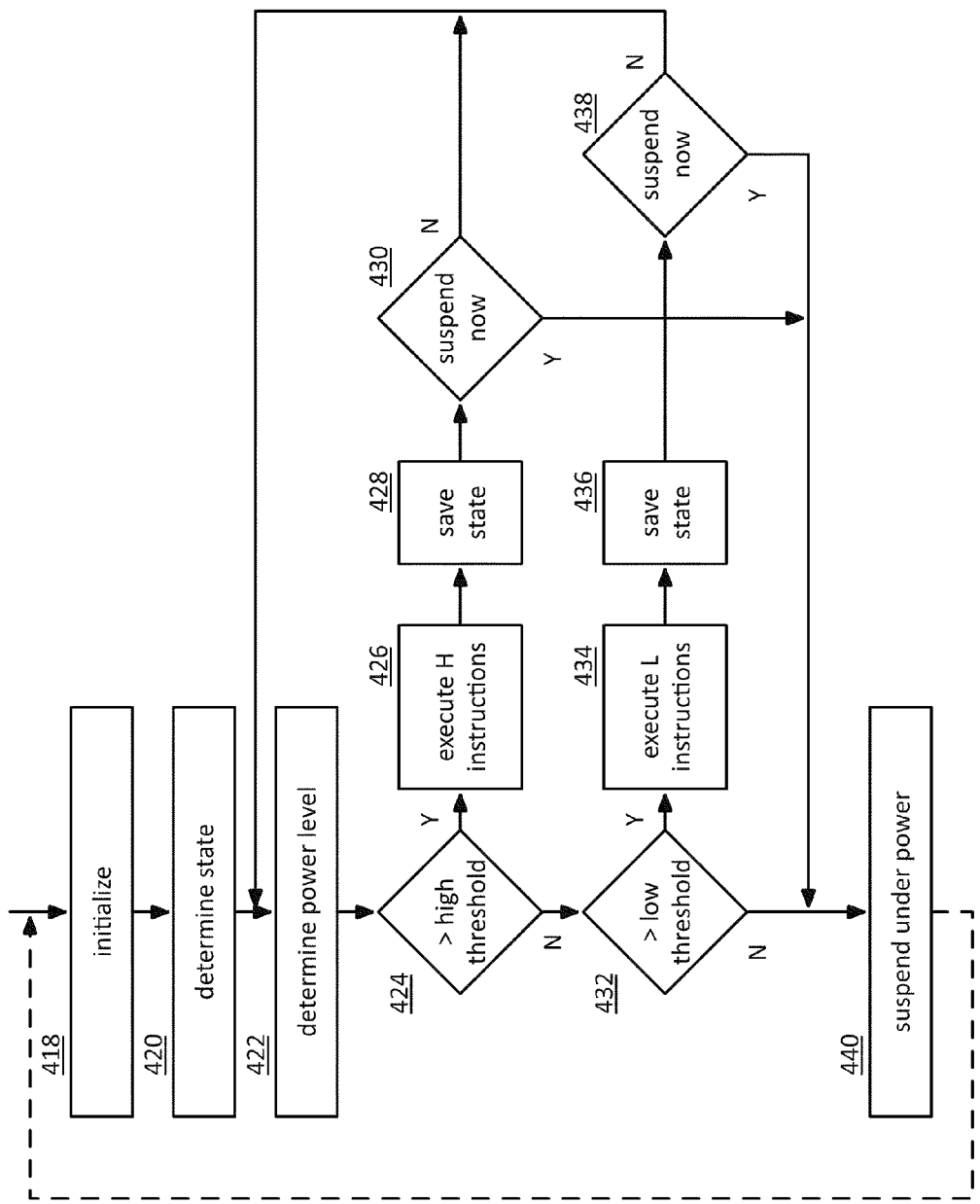
FIG. 63 is a logic diagram of an embodiment of a method for bio-medical unit communications in accordance with the invention.

FIG. 63 is a flowchart of an embodiment of a method for controlling power harvesting within a bio-medical unit 10. The method begins at step 418 wherein the processing module 50 of the bio-medical unit 10 initializes (e.g., when it is supplied power and wakes up) itself. For example, the processing module 50 executes an initialization boot sequence stored in the memory 52. The initialization boot sequence includes operational instructions that cause the processing module to initialize its registers to accept further instructions. The initialization boot sequence may further include operational instructions to initialize one or more of the communication module 48, the functional module(s) 54 initialized, etc.

The method continues at step 420 where the processing module 50 determines the state of the bio-medical unit (e.g., actively involved in a task, inactive, data gathering, performing a function, etc.). Such a determination may be based on one or more of previous state(s) (e.g., when the processing module was stopped prior to losing power), an input from the functional module 54, a list of steps or elements of a task, the current step of a MRI sequence, and/or new tasks received via the communication module 48.

The method continues at step 422 where the processing module 50 determines the bio-medical unit power level, which may be done by measuring the power harvesting module 46 output Vdd 56. Note that voltage is one proxy for the power level and that other proxies may be utilized including estimation of milliWatt-hours available, a time of operation before loss of operating power estimate, a number of CPU instructions estimate, a number of task elements, a number of tasks estimate, and/or another other estimator to assist in determining how much the bio-medical unit 10 can accomplish prior to losing power. Further note that the processing module 50 may save historic records of power utilization in the memory 52 to assist in subsequent determinations of the power level.

The method continues at step 424 where the processing module 50 compares the power level to the high threshold (e.g., a first available power level that allows for a certain level of processing). If yes, the method continues to step 426 where the processing module 50 enables the execution of H number of instructions. The processing module 50 may utilize a predetermined static value of the H instructions or a dynamic value that changes as a result of the historic records. For example, the historic records may indicate that there was an average of 20% more power capacity left over after the last ten times of instruction execution upon initialization. The processing module 50 may adjust the value of H upward such that the on-going left over power is less than 20% in order to more fully utilize the available power each time the bio-medical unit 10 has power.

The method continues at step 428 where the processing module 50 saves the state in the memory 52 upon completion of the execution of the H instructions such that the processing module 50 can start in a state in accordance with this state upon the next initialization. The method then continues at step 430 where the processing module 50 determines whether it will suspend operations based on one or more of a re-determined power level (e.g., power left after executing the instructions), a predetermined list, a task priority, a task state, a priority indicator, a command, a message, and/or a functional module input. If not, the method repeats at step 422. If yes, the method branches to step 440 where the processing module 50 suspends operations of the bio-medical unit.

If, at step 424, the power level is not greater than the high threshold, the method continues at step 432 where the processing module 50 determines whether the power level compares favorably to a low threshold. If not, the method continues a step 440 where the processing module 50 suspends operations of the bio-medical unit.

If the comparison at step 432 was favorable, the method continues at step 434 where the processing module 50 executes L instructions. The processing module 50 may utilize a predetermined static value of the L instructions or a dynamic value that changes as a result of the historic records as discussed previously. For example, the historic records may indicate that there was an average of 10% more power capacity left over after the last ten times of instruction execution upon initialization. The processing module 50 may adjust the value of L downward such that the on-going left over power is less than 10% in order to more fully utilize the available power each time the bio-medical unit 10 has power.

The method continues at step 436 where the processing module 50 saves the state in the memory 52 upon completion of the execution of the L instructions such that the processing module 50 can start in a state in accordance with this state upon the next initialization. The method then continues at step 438 where the processing module 50 determines whether it will suspend operations based on one or more of a re-determined power level (e.g., power left after executing the instructions), a predetermined list, a task priority, a task state, a priority indicator, a command, a message, and/or a functional module input. If yes, the method branches to step 440. If not, the method repeats at step 422.

Figure 64:
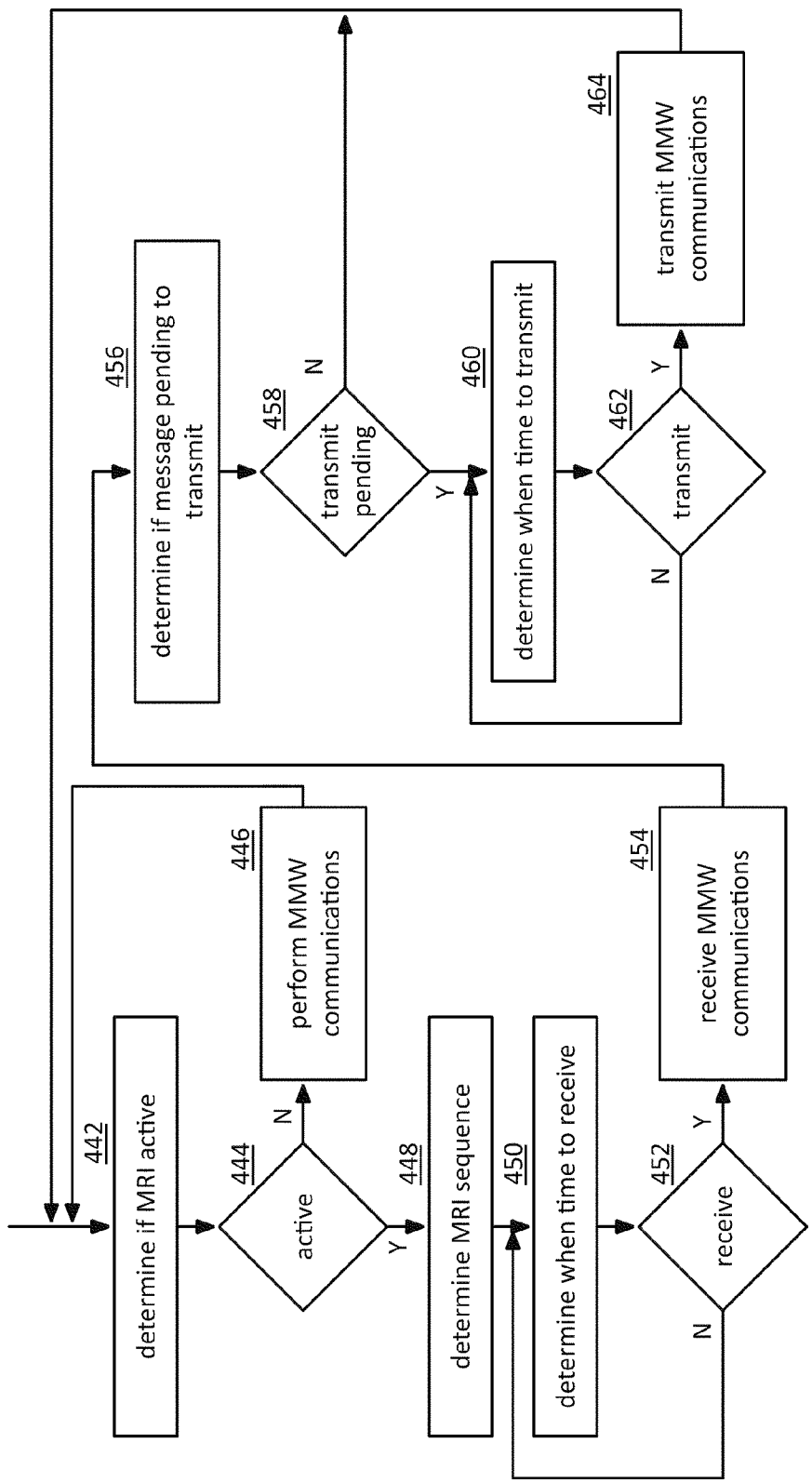
FIG. 64 is a logic diagram of an embodiment of a method for MMW communications within a MRI sequence in accordance with the invention.

FIG. 64 is a flowchart illustrating MMW communications within a MRI sequence where the processing module 50 determines MMW communications in accordance with an MRI sequence. The method begins at step 442 where the processing module 50 determines whether the MRI is active based on receiving MRI EM signals. At step 444, the method branches to step 446 or step 448. When the MRI is active, the method continues at step 446 where the processing module 50 performs MMW communications as previously discussed.

The method continues at step 448 where the processing module 50 determines the MRI sequence based on received MRI EM signals (e.g., gradient pulses and/or MRI RF pulses as shown in one or more of the preceding figures). The method continues at step 450 where the processing module 50 determines whether it is time to perform receive MMW communication in accordance with the MRI sequence. For example, the MMW transceiver 138 may receive MMW inbound signals 148 between any of the MRI sequence steps. As another example, the MMW transceiver 138 may receive MMW inbound signals 148 between specific predetermined steps of the MRI sequence.

At step 452 the method branches back to step 450 or to step 454. When it is time to receive, the method continues at step 454 where the processing module 50 coordinates the MMW transceiver 138 receiving the MMW inbound signals, which may include one or more of a status request, a records request, a sensor data request, a processed data request, a position request, a command, and/or a request for MRI echo signal data. The method then continues at step 456 where the processing module 50 determines whether there is at least one message pending to transmit (e.g., in a transmit queue). At step 458 the method branches back to step 442 or to step 460.

At step 460, the processing module 50 determines when it is time to transmit a MMW communication in accordance with the MRI sequence. For example, the MMW transceiver 138 may transmit MMW outbound signals 150 between any of the MRI sequence steps. As another example, the MMW transceiver 138 may transmit MMW outbound signals 150 between specific predetermined steps of the MRI sequence.

At step 462, the method branches to back step 456 or to step 464. The method continues at step 464 where the processing module 50 coordinates the MMW transceiver 138 transmitting the MMW outbound signals 150, which may include one or more of a status request response, a records request response, a sensor data request response, a processed data request response, a position request response, a command response, and/or a request for MRI echo signal data response. The method then branches back to step 442.

Figure 65:
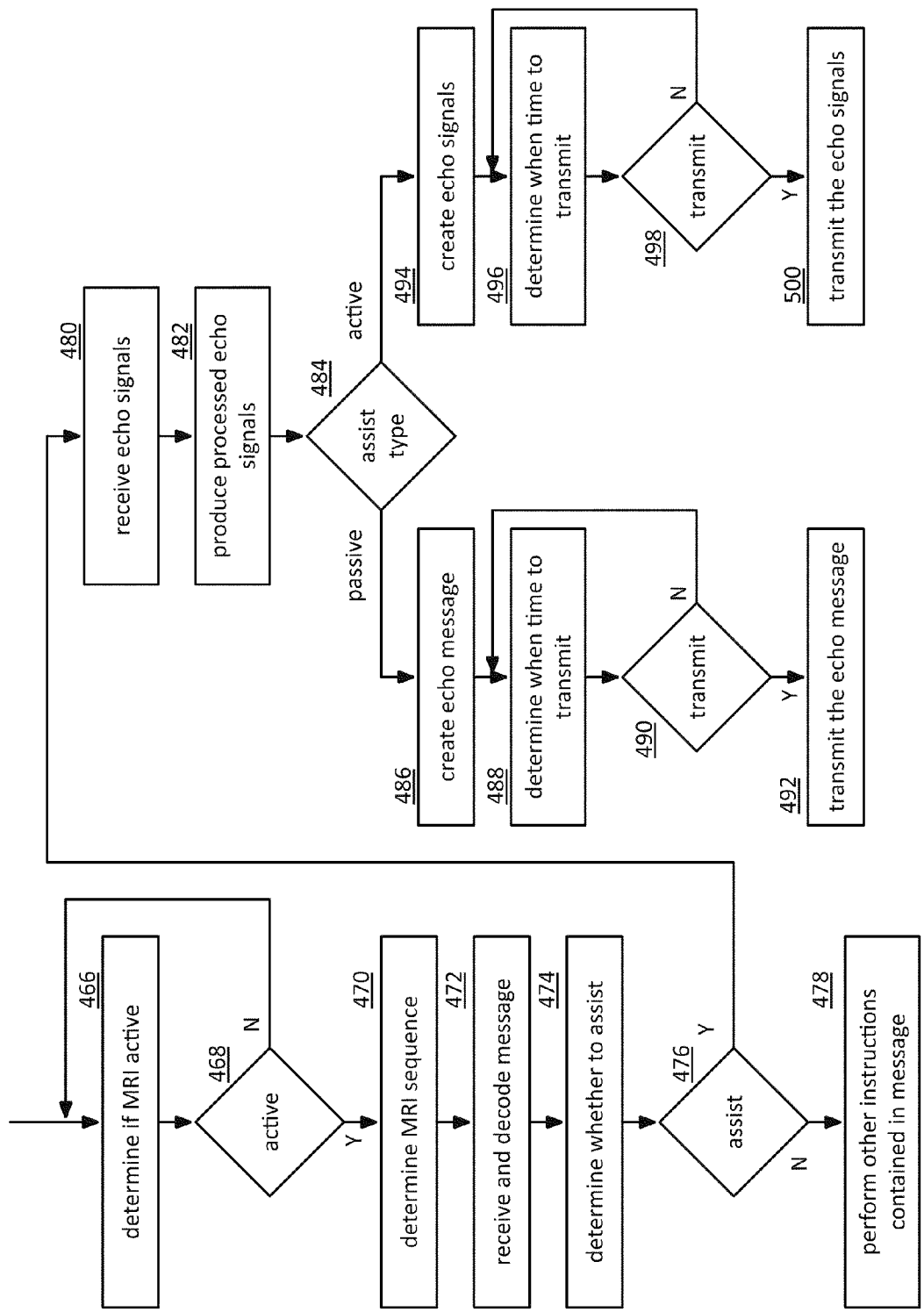
FIG. 65 is a logic diagram of an embodiment of a method for processing of MRI signals in accordance with the present invention.

FIG. 65 is a flowchart illustrating the processing of MRI signals where the processing module 50 of the bio-medical unit 10 may assist the MRI in the reception and processing of MRI EM signals 146. The method begins at step 466 where the processing module 50 determines if the MRI is active based on receiving MRI EM signals 146. The method branches back to step 466 when the processing module 50 determines that the MRI is not active. For example, the MRI sequence may not start until the processing module 50 communicates to the MRI unit that it is available to assist. The method continues to step 470 when the processing module 50 determines that the MRI is active.

At step 470, the processing module 50 determines the MRI sequence based on received MRI EM signals 146 (e.g., gradient pulses and/or MRI RF pulses). At step 472, the processing module receives EM signals 146 and/or MMW communication 532 in accordance with the MRI sequence and decodes a message. For example, the MMW transceiver 138 may receive MMW inbound signals 148 between any of the MRI sequence steps. As another example, the MMW transceiver 138 may receive MMW inbound signals 148 between specific predetermined steps of the MRI sequence. In yet another example, the processing module 50 may receive EM signals 146 at any point of the MRI sequence such that the EM signals 146 contain a message for the processing module 50.

At step 474, the processing module 50 determines whether to assist in the MRI sequence based in part on the decoded message. The determination may be based on a comparison of the assist request to the capabilities of the bio-medical unit 10. At step 476, the method branches to step 480 when the processing module 50 determines to assist in the MRI sequence. The method continues at step 478 where the processing module 50 performs other instructions contained in the message and the method ends.

At step 480, the processing module 50 begins the assist steps by receiving echo signals 530 during the MRI sequence. Note the echo signals 530 may comprise EM RF signals across a wide frequency band as reflected off of tissue during the MRI sequence. At step 482, the processing module 50 processes the received echo signals 530 to produce processed echo signals. Note that this may be a portion of the overall processing required to lead to the desired MRI imaging.

At step 484, the processing module 50 determines the assist type based on the decoded message from the MRI unit. The assist type may be at least passive or active where the passive type collects echo signal 530 information and sends it to the MRI unit via MMW outbound signals 150 and the active type collects echo signal information and re-generates a form of the echo signals 530 and sends the re-generated echo signals to the MRI unit via outbound modulated EM signals (e.g., the MRI unit interprets the re-generated echo signals as echo signals to improve the overall system gain and sensitivity).

The method branches to step 494 when the processing module 50 determines the assist type to be active. The method continues to step 486 when the processing module 50 determines the assist type to be passive. At step 486, the processing module 50 creates an echo message based on the processed echo signals where the echo message contains information about the echo signals 530.

At step 488, the processing module 50 determines when it is time to transmit the echo message encoded as MMW outbound signals 150 via MMW communication in accordance with the MRI sequence. For example, the MMW transceiver 138 may transmit MMW outbound signals 150 between any of the MRI sequence steps. In another example, the MMW transceiver 138 may transmit MMW outbound signals 150 between specific predetermined steps of the MRI sequence.

At step 490, the method branches back to step 488 when the processing module 50 determines that it is not time to transmit the echo message. At step 490, the method continues to step 492 where the processing module 50 transmits the echo message encoded as MMW outbound signals 150.

At step 494, the processing module 50 creates echo signals based on the processed echo signals. At step 496, the processing module 50 determines when it is time to transmit the echo signals as outbound modulated EM signals 180 in accordance with the MRI sequence. At step 498, the method branches back to step 496 when the processing module 50 determines that it is not time to transmit the echo signals. At step 498, the method continues to step 500 where the processing module 50 transmits the echo signals encoded as outbound modulated EM signals 180. Note that the transmitted echo signals emulate the received echo signals 530 with improvements to overcome low MRI power levels and/or low MRI receiver sensitivity.

Figure 66:
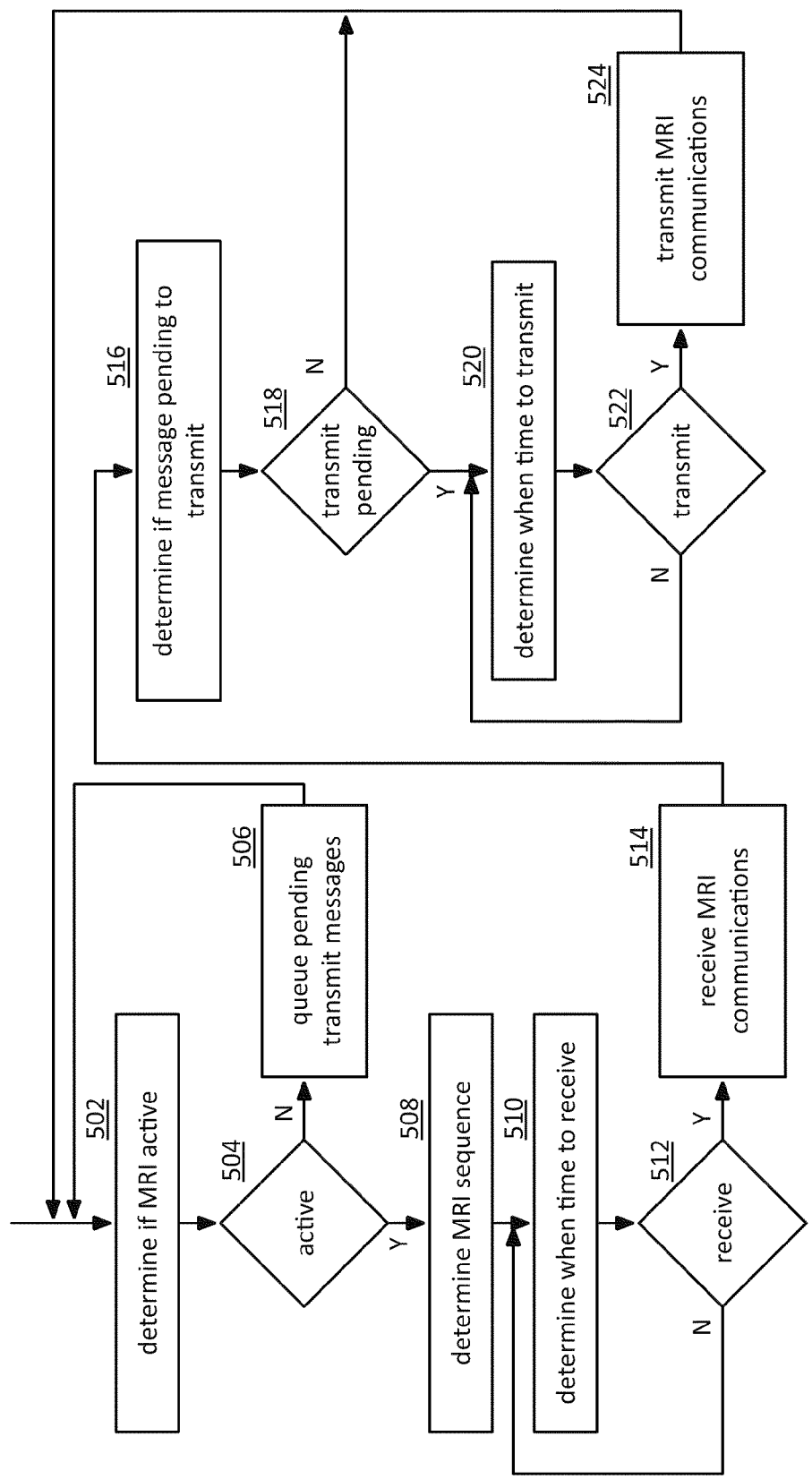
FIG. 66 is a logic diagram of an embodiment of a method for communication utilizing MRI signals in accordance with the present invention.

FIG. 66 is a flowchart illustrating communication utilizing MRI signals where the processing module 50 determines MMW signaling in accordance with an MRI sequence. The method begins at step 502 where the processing module 50 determines if the MRI is active based on receiving MRI EM signals 146. At step 504, the method branches to step 508 when the processing module 50 determines that the MRI is active. At step 504, the method continues to step 506 when the processing module 50 determines that the MRI is not active. At step 506, the processing module 50 queues pending transmit messages. The method branches to step 502.

At step 508, the processing module 50 determines the MRI sequence based on received MRI EM signals 146 (e.g., gradient pulses and/or MRI RF pulses). At step 510, the processing module 50 determines when it is time to perform receive communication in accordance with the MRI sequence. For example, the EM transceiver 174 may receive inbound modulated EM signals 146 containing message information from any of the MRI sequence steps.

At step 512, the method branches back to step 510 when the processing module 50 determines that it is not time to perform receive communication. At step 512, the method continues to step 514 where the processing module 50 directs the EM transceiver 174 to receive the inbound modulated EM signals. The processing module 50 may decode messages from the inbound modulated EM signals 146 such that the messages include one or more of a echo signal collection assist request, a status request, a records request, a sensor data request, a processed data request, a position request, a command, and/or a request for MRI echo signal data. Note that the message may be decoded from the inbound modulated EM signals 146 in one or more ways including detection of the ordering of the magnetic gradient pulses, counting the number of gradient pulses, the slice pulse orderings, detecting small differences in the timing of the pulses, and/or demodulation of the MRI RF pulse.

At step 516 the processing module 50 determines if there is at least one message pending to transmit (e.g., in a transmit queue). At step 518, the method branches back to step 502 when the processing module 50 determines that there is not at least one message pending to transmit. At step 518, the method continues to step 520 where the processing module 50 determines when it is time to perform transmit communication in accordance with the MRI sequence. For example, the EM transceiver 174 may transmit outbound modulated EM signals 180 between any of the MRI sequence steps. In another example, the EM transceiver 174 may transmit the outbound modulated EM signals 180 between specific predetermined steps of the MRI sequence. In yet another example, the EM transceiver 174 may transmit the outbound modulated EM signals 180 in parallel with specific predetermined steps of the MRI sequence, but may utilize a different set of frequencies unique to the EM transceiver 174.

At step 522, the method branches back to step 520 when the processing module 50 determines that it is not time to perform transmit communication. At step 522, the method continues to step 524 where the processing module 50 directs the EM transceiver 174 to prepare the outbound modulated EM signals 180 based on the at least one message pending to transmit. The processing module 50 may encode messages into the outbound modulated EM signals 180 such that the messages include one or more of a status request response, a records request response, a sensor data request response, a processed data request response, a position request response, a command response, and/or a request for MRI echo signal data response. The method branches back to step 502.

Figure 67:
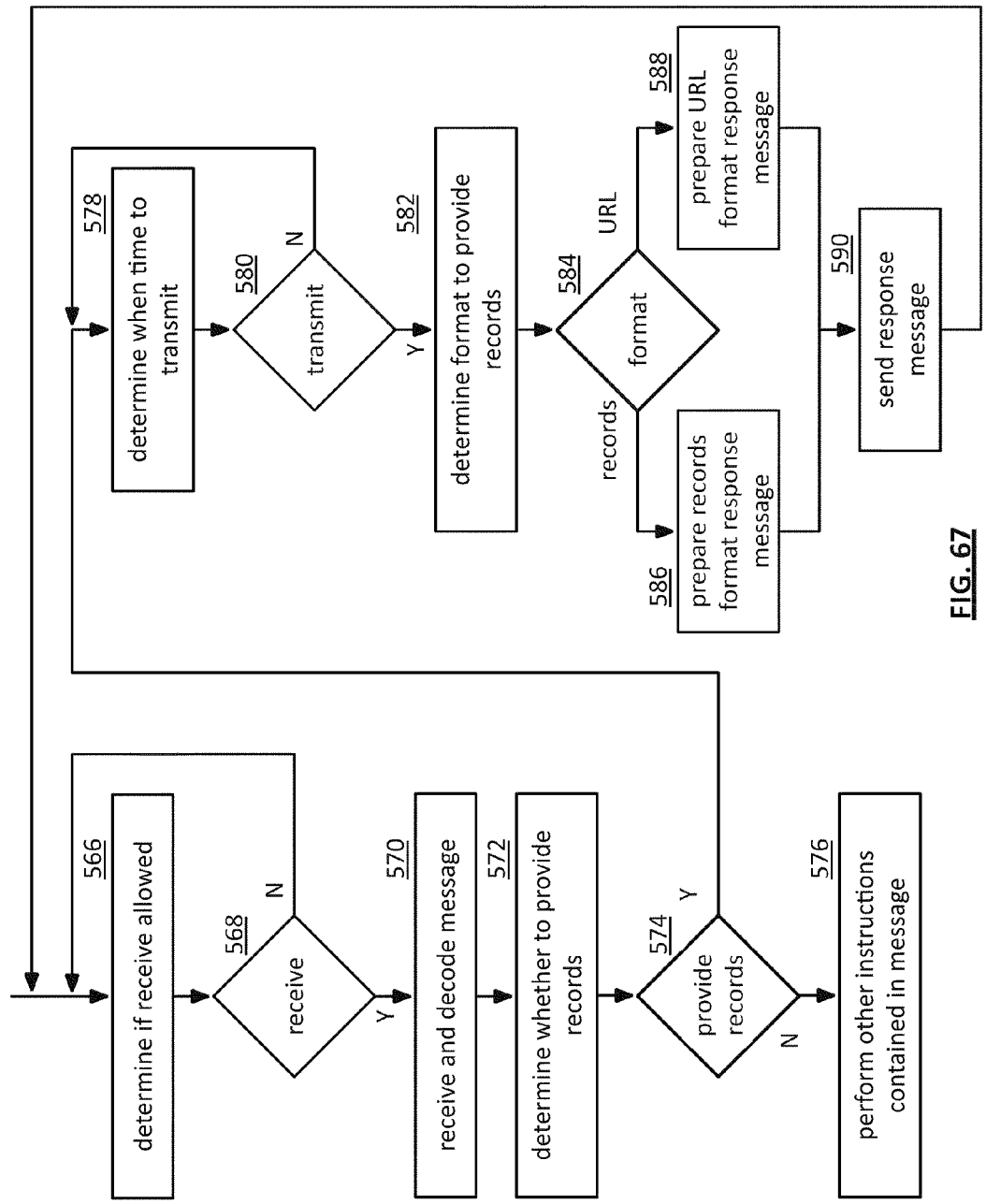
FIG. 67 is a logic diagram of another embodiment of a method for bio-medical unit communications in accordance with the invention.

FIG. 67 is a flowchart illustrating the communication of records where the processing module 50 of the bio-medical unit 10 determines to provide medical records. The method begins at step 566 where the processing module 50 determines if receiving MMW communication is allowed. The determination may be based on one or more of a timer, a command, available power, a priority indicator, and/or interference indicator. For example, the MMW transceiver 138 may receive MMW inbound signals 148 for a 500 millisecond window every 3 minutes.

At step 568, the method branches back to step 566 when the processing module 50 determines that receiving MMW communication is not allowed. At step 568, the method continues to step 570 where the processing module 50 directs the MMW transceiver 138 to receive MMW inbound signals 148. The processing module 50 may decode messages from the MMW inbound signals 148 such that the decoded message include one or more of a status request, a records request, a sensor data request, a processed data request, a position request, a command, and/or a request for MRI echo signal data.

At step 572, the processing module 50 determines whether to provide records in response to the records request based in part on the decoded message. The determination may be based on a comparison of the records request to the capabilities of the bio-medical unit 10. Note that records may include patient history, medications, alerts, allergies, personal information, contact information, age, weight, test results, etc.

At step 576, the method branches to step 578 when the processing module 50 determines to provide records. At step 576, the method continues to step 576 when the processing module 50 determines to not provide records. At step 576, the processing module 50 performs other instructions contained in the message. The method ends.

At step 578, the processing module 50 determines when it is time to transmit. The determination may be based on a timer, a command, available power, a priority indicator, a timeslot, and/or interference indicator. At step 580, the method branches back to step 578 when the processing module 50 determines it is not time to transmit. At step 580, the method continues to step 582 when the processing module 50 determines it is time to transmit.

At step 582, the processing module 50 determines the format to provide records. The format determination may be based on one or more of a memory lookup, a command, available power, the type of records requested, an access ID of the requester, a priority indicator, a level of detail indicator, and/or a freshness indicator. Note that the format may include records format as stored in the bio-medical unit memory (e.g., all or a portion of the records) or a uniform resource locator (URL) to link to another memory in one or more of the service provider's computer, the database, and/or the server.

At step 584, the method branches to step 588 when the processing module 50 determines the format to provide records is the URL format. At step 584, the method continues to step 586 where the processing module 50 prepares the records format response message based on records information retrieved from the bio-medical unit memory 52. The method branches to step 590.

At step 588, the processing module prepares the URL format response message based on retrieving the URL from the bio-medical unit memory 52. At step 590, the processing module 50 transmits the response message encoded as MMW outbound signals 150. For example, the bio-medical unit 10 transmits the response message via a second wireless communications medium including one or more of infrared signals, ultrasonic signals, visible light signals, audible sound signals, and/or EM signals via one or more of the functional modules.

Figure 68:
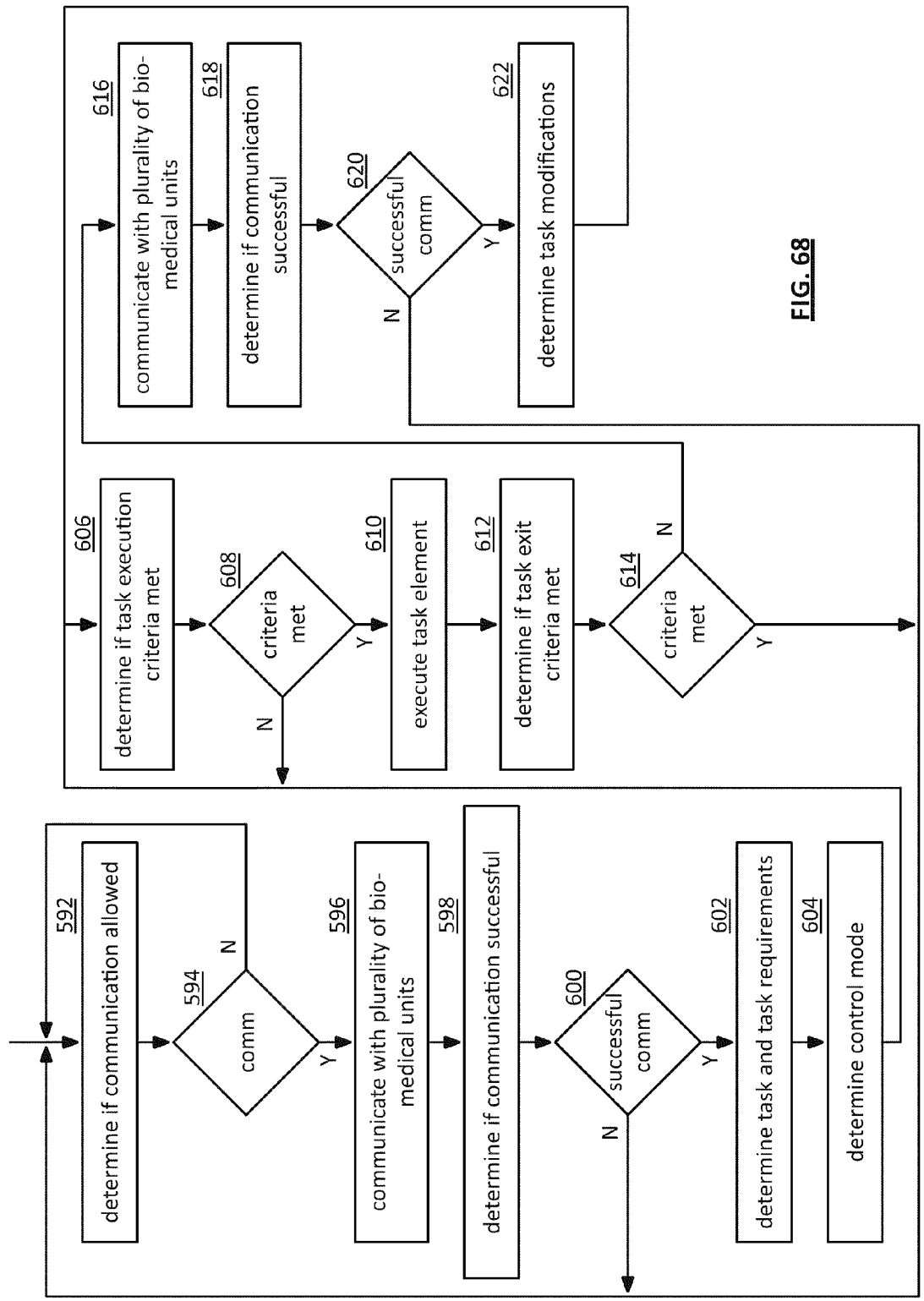
FIG. 68 is a logic diagram of an embodiment of a method for coordination of bio-medical unit task execution in accordance with the present invention.

FIG. 68 is a flowchart illustrating the coordination of bio-medical unit task execution where the processing module 50 determines and executes tasks with at least one other bio-medical unit 10. The method begins at step 592 where the processing module 50 determines if communication is allowed. The determination may be based on one or more of a timer, a command, available power, a priority indicator, an MRI sequence, and/or interference indicator.

At step 594, the method branches back to step 592 when the processing module 50 determines that communication is not allowed. At step 594, the method continues to step 596 when the processing module 50 determines that communication is allowed. At step 596, the processing module 50 directs the communication module 48 to communicate with a plurality of bio-medical units 10 utilizing RF and/or MMW inbound and/or outbound signals. The processing module 50 may decode messages from the RF and/or MMW inbound and/or outbound signals inbound signals. At step 598, the processing module 50 determines if communications with the plurality of bio-medical units 10 is successful based in part on the decoded messages.

At step 600, the method branches back to step 592 when the processing module determines that communications with the plurality of bio-medical units 10 is not successful. Note that forming a network with the other bio-medical units 10 may be required to enable joint actions. At step 600, the method continues to step 602 when the processing module 50 determines that communications with the plurality of bio-medical units 10 is successful.

At step 602, the processing module 50 determines the task and task requirements. The task determination may be based on one or more of a command from a parent bio-medical unit 10, external communications, a preprogrammed list, and/or in response to sensor data. The task requirements determination may be based on one or more of the task, a command from a parent bio-medical unit 10, external communications, a preprogrammed list, and/or in response to sensor data. Note that the task may include actions including one or more of drilling, moving, sawing, jumping, spreading, sensing, lighting, pinging, testing, and/or administering medication.

At step 604, the processing module 50 determines the control mode based on one or more of a command from a parent bio-medical unit 10, external communications, a preprogrammed list, and/or in response to sensor data. Note that the control mode may include autonomous, parent (bio-medical unit), server, and/or peer.

At step 606, the processing module 50 determines if task execution criteria are met based on sensor data, communication with other bio-medical units 10, a command, a status indicator, a safety indicator, a stop indicator, and/or location information. Note that the task execution criteria may include one or more of safety checks, position information of the bio-medical unit 10, position information of other bio-medical units 10, and/or sensor data thresholds.

At step 608, the method branches back to step 606 when the processing module 50 determines that the task execution criteria are not met. At step 608, the method continues to step 610 when the processing module 50 determines that the task execution criteria are met. At step 610, the processing module 50 executes a task element. A task element may include a portion or step of the overall task. For example, move one centimeter of a task to move three centimeters.

At step 612, the processing module 50 determines if task exit criteria are met based on a task element checklist status, sensor data, communication with other bio-medical units 10, a command, a status indicator, a safety indicator, a stop indicator, and/or location information. Note that the task exit criteria define successful completion of the task.

At step 614, the method branches back to step 592 when the processing module 50 determines that the task exit criteria are met. In other words, the plurality of bio-medical units 10 is done with the current task and is ready for the next task. At step 614, the method continues to step 616 when the processing module 50 determines that the task exit criteria are not met.

At step 616, the processing module 50 directs the communication module 48 to communicate with the plurality of bio-medical units 10 utilizing RF and/or MMW inbound and/or outbound. The processing module 50 may decode messages from the RF and/or MMW inbound and/or outbound signals inbound signals. Note that the messages may include information in regards to task modifications (e.g., course corrections). At step 618, the processing module 50 determines if communications with the plurality of bio-medical units 10 is successful based in part on the decoded messages.

At step 620, the method branches back to step 592 when the processing module determines that communications with the plurality of bio-medical units is not successful (e.g., to potentially restart). Note that maintaining the network with the other bio-medical unit may be required to enable joint actions. At step 620, the method continues to step 622 when the processing module determines that communications with the plurality of bio-medical units is successful.

At step 622, the processing module 50 determines task modifications. The task modifications may be based on one or more of a command from a parent bio-medical unit 10, and/or external communications. The task modifications determination may be based on one or more of the task, a command from a parent bio-medical unit 10, external communications, a preprogrammed list, and/or in response to sensor data. The method branches back to step 606 to attempt to complete the current task.

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, component values, integrated circuit process variations, temperature variations, rise and fall times, and/or thermal noise. Such relativity between items ranges from a difference of a few percent to magnitude differences. As may also be used herein, the term(s) "coupled to" and/or "coupling" and/or includes direct coupling between items and/or indirect coupling between items via an intervening item (e.g., an item includes, but is not limited to, a component, an element, a circuit, and/or a module) where, for indirect coupling, the intervening item does not modify the information of a signal but may adjust its current level, voltage level, and/or power level. As may further be used herein, inferred coupling (i.e., where one element is coupled to another element by inference) includes direct and indirect coupling between two items in the same manner as "coupled to". As may even further be used herein, the term "operable to" indicates that an item includes one or more of power connections, input(s), output (s), etc., to perform one or more its corresponding functions and may further include inferred coupling to one or more other items. As may still further be used herein, the term "associated with", includes direct and/or indirect coupling of separate items and/or one item being embedded within another item. As may be used herein, the term "compares favorably", indicates that a comparison between two or more items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1.

The present invention has also been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claimed invention.

The present invention has been described above with the aid of functional building blocks illustrating the performance of certain significant functions. The boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality. To the extent used, the flow diagram block boundaries and sequence could have been defined otherwise and still perform the certain significant functionality. Such alternate definitions of both functional building blocks and flow diagram blocks and sequences are thus within the scope and spirit of the claimed invention. One of average skill in the art will also recognize that the functional building blocks, and other illustrative blocks, modules and components herein, can be implemented as illustrated or by discrete components, application specific integrated circuits, processors executing appropriate software and the like or any combination thereof.

What is claimed is:

1. A system comprises:
    a plurality of bio-medical units configured to associate with a body object, wherein a bio-medical unit of the plurality of bio-medical units includes:
        a power harvesting module configured to generate a supply voltage from an electromagnetic signal;
        a wireless communication module powered via the supply voltage and configured to:
            convert a received wireless communication into a physical therapy command; and
            convert a physical therapy response into a transmit wireless communication;
        a processing module powered via the supply voltage and configured to:
            interpret the physical therapy command to determine a physical therapy function; and
            generate the physical therapy response based on physical therapy data;
        a functional module powered via the supply voltage and configured to:
            perform the physical therapy function; and
            when the physical therapy function is a monitoring function, generate the physical therapy data; and
    an electromagnetic signal generating unit that includes:
        at least one signal generating module configured to generate one or more signals; and
        a plurality of near field communication (NFC) modules, wherein an NFC module of the plurality of NFC modules is configured to convert at least one of the one or more signals into a component of the electromagnetic signal.

2. The system of claim 1, wherein the physical therapy function further comprises at least one of:
    an electric stimulation function;
    the monitoring function that includes at least one of:
        monitoring correct form of a physical therapy movement;
        monitoring program compliance;
        monitoring effort level;
        monitoring pain level; and
    an electromyography function.

3. The system of claim 1, wherein the electromagnetic signal generating unit further comprises:
    a communication module configured to communicate the received wireless communication and the transmit wireless communication with the plurality of bio-medical units.

4. The system of claim 3, wherein the electromagnetic signal generating unit further comprises:
    a processing module configured to:
        execute a physical therapy program to produce the physical therapy command; and
        generate an electromagnetic signal pattern configured to enable the plurality of NFC modules to produce the electromagnetic signal.

5. The system of claim 4, wherein the electromagnetic signal generating unit further comprises:
    a second communication module operable to:
        receive operational instructions regarding the physical therapy program from a wireless communication device; and
        transmit feedback regarding execution of the physical therapy program to the wireless communication device.

6. The system of claim 1 further comprises:
    wearable housing configured to be placed on exterior of body over the body object, wherein the wearable housing supports at least one of the electromagnetic signal generating unit and at least some of the plurality of bio-medical units.

7. The system of claim 1, wherein the electromagnetic signal generating unit further comprises:
    a processing module operable to:
        convert the physical therapy command into an outbound symbol stream; and
        convert an inbound system stream into the physical therapy response; and
    the NFC module is further configured to:
        convert the outbound symbol stream into an outbound wireless signal, which is received by communication module of the bio-medical unit as the received wireless communication; and
        convert an inbound wireless signal into the inbound wireless signal, wherein the inbound signal corresponds to the transmit wireless communication.

8. The system of claim 1, wherein the at least one signal generating module comprises:
    a plurality of signal generating modules operably coupled to the plurality of NFC modules.

9. An electromagnetic signal generating unit comprises:
    at least one signal generating module configured to generate one or more signals; and
    a plurality of near field communication (NFC) modules, wherein an NFC module of the plurality of NFC modules is configured to convert at least one of the one or more signals into a component of an electromagnetic signal that is used to wirelessly power one or more bio-medical units.

10. The electromagnetic signal generating unit of claim 9 further comprises:
    a communication module configured to communicate an inbound wireless communication and an outbound wireless communication with the one or more bio-medical units.

11. The electromagnetic signal generating unit of claim 10 further comprises:
a processing module configured to:
execute a physical therapy program to produce a physical therapy command;
generate an electromagnetic signal pattern configured to enable the plurality of NFC modules to produce the electromagnetic signal.

12. The electromagnetic signal generating unit of claim 11 further comprises:
a second communication module configured to:
receive operational instructions regarding the physical therapy program from a wireless communication device; and
transmit feedback regarding execution of the physical therapy program to the wireless communication device.

13. The electromagnetic signal generating unit of claim 9 further comprises:
wearable housing configured to be placed on exterior of body over a body object, wherein the wearable housing supports the electromagnetic signal generating unit.

14. The electromagnetic signal generating unit of claim 9 further comprises:
a processing module configured to:
convert a physical therapy command into an outbound symbol stream; and
convert an inbound system stream into a physical therapy response; and
the NFC module is further configured to:
convert the outbound symbol stream into an outbound wireless signal, which is received by a communication module of the one or more bio-medical units; and
convert an inbound wireless signal into the inbound wireless signal, wherein the inbound signal corresponds to the wireless communication received from the one or more bio-medical units.

15. The electromagnetic signal generating unit of claim 9 further comprises:
a plurality of signal generating modules operably coupled to the plurality of NFC modules.

16. A circuit comprises:
a signal generating unit operable to generate one or more signals;
a near field communication (NFC) module configured to generate a component of an electromagnetic signal based on at least one of the one or more signals, wherein the component wirelessly powers one or more bio-medical units; and
a processing module configured to:
convert a physical therapy command into an outbound symbol stream; and
convert an inbound system stream into a physical therapy response, wherein the circuit is operable to:
convert the outbound symbol stream into an outbound wireless signal configured to be transmitted to the one or more bio-medical units; and
convert an inbound wireless signal into the inbound wireless signal, wherein the inbound wireless signal is received from at least one of the one or more bio-medical units.

17. The circuit of claim 16, wherein the NFC module is further operable to:
convert the outbound symbol stream into the outbound wireless signal configured to be transmitted to the one or more bio-medical units; and
convert the inbound wireless signal into the inbound wireless signal, wherein the inbound wireless signal is received from at least one of the one or more bio-medical units.

18. The circuit of claim 16 further comprises:
a radio frequency (RF) communication module configured to:
convert the outbound symbol stream into the outbound wireless signal configured to be transmitted to the one or more bio-medical units; and
convert the inbound wireless signal into the inbound wireless signal, wherein the inbound wireless signal is received from at least one of the one or more bio-medical units.

19. The circuit of claim 16 further comprises:
a communication module configured to:
receive operational instructions regarding a physical therapy program from a wireless communication device; and
transmit feedback regarding execution of the physical therapy program to the wireless communication device.

20. The circuit of claim 16, wherein the physical therapy command comprises at least one of:
an electric stimulation command; and
a monitoring command that includes at least one of:
monitoring correct form of a physical therapy movement;
monitoring program compliance;
monitoring effort level;
monitoring pain level; and
an electromyography function.

* * * * *